US012042479B2

(12) United States Patent
Hossain

(10) Patent No.: US 12,042,479 B2
(45) Date of Patent: Jul. 23, 2024

(54) USE OF TOPICAL FORMULATIONS OF CANNABINOIDS IN THE TREATMENT OF EPIDERMOLYSIS BULLOSA AND RELATED CONNECTIVE TISSUE DISORDERS

(71) Applicant: INMED PHARMACEUTICALS INC., Vancouver (CA)

(72) Inventor: Sazzad Hossain, Richmond (CA)

(73) Assignee: INMED PHARMACEUTICALS INC.

( * ) Notice: Subject to any disclaimer, the term of this patent is extended or adjusted under 35 U.S.C. 154(b) by 425 days.

(21) Appl. No.: 16/098,324

(22) PCT Filed: May 4, 2017

(86) PCT No.: PCT/CA2017/050546
§ 371 (c)(1),
(2) Date: Nov. 1, 2018

(87) PCT Pub. No.: WO2017/190249
PCT Pub. Date: Nov. 9, 2017

(65) Prior Publication Data
US 2019/0142788 A1 May 16, 2019

Related U.S. Application Data

(60) Provisional application No. 62/331,633, filed on May 4, 2016.

(51) Int. Cl.
| A61K 31/352 | (2006.01) |
| A61K 9/00 | (2006.01) |
| A61K 31/045 | (2006.01) |
| A61K 31/05 | (2006.01) |
| A61K 45/06 | (2006.01) |
| A61P 17/00 | (2006.01) |

(52) U.S. Cl.
CPC .......... *A61K 31/352* (2013.01); *A61K 9/0014* (2013.01); *A61K 31/045* (2013.01); *A61K 31/05* (2013.01); *A61K 45/06* (2013.01); *A61P 17/00* (2018.01)

(58) Field of Classification Search
CPC .... A61K 31/352; A61K 31/05; A61K 9/0014; A61P 17/00
See application file for complete search history.

(56) References Cited

U.S. PATENT DOCUMENTS

| 6,284,788 | B1 | 9/2001 | Mittendorf et al. |
| 6,573,292 | B1 | 6/2003 | Nardella |
| 6,825,209 | B2 | 11/2004 | Thomas et al. |
| 6,921,722 | B2 | 7/2005 | Ogure et al. |
| 7,109,216 | B2 | 9/2006 | Kruse et al. |
| 7,294,645 | B2 | 11/2007 | Barth et al. |
| 7,314,886 | B2 | 1/2008 | Chao et al. |
| 7,446,122 | B2 | 11/2008 | Chao et al. |
| 7,504,522 | B2 | 3/2009 | Davidson et al. |
| 7,700,634 | B2 | 4/2010 | Adam-Worrall et al. |
| 8,778,950 | B2 | 7/2014 | Jones et al. |
| 9,133,128 | B2 | 9/2015 | Fulp et al. |
| 9,173,867 | B2 | 11/2015 | Travis |
| 9,284,303 | B2 | 3/2016 | Gijsen et al. |
| 9,376,367 | B2 | 6/2016 | Herkenroth et al. |
| 9,394,267 | B2 | 7/2016 | Attala et al. |
| 2005/0266061 | A1 | 12/2005 | Stinchcomb et al. |
| 2010/0035978 | A1 | 2/2010 | Guy |
| 2010/0273895 | A1 | 4/2010 | Stinchcomb et al. |
| 2015/0126595 | A1* | 5/2015 | Smith ............... A61K 31/01 514/454 |
| 2015/0297556 | A1 | 10/2015 | Smith |
| 2016/0303039 | A1 | 10/2016 | Smith |

FOREIGN PATENT DOCUMENTS

| EP | 1588697 A1 | 10/2005 |
| EP | 1645270 B1 | 4/2006 |
| WO | WO 2005/120478 A1 | 12/2005 |
| WO | WO 2006/111424 A1 | 10/2006 |
| WO | WO 2007/001891 A1 | 1/2007 |
| WO | WO 2007/148094 A1 | 12/2007 |
| WO | WO 2010/013240 A1 | 2/2010 |
| WO | WO 2010/126501 A1 | 11/2010 |
| WO | WO 2012/160358 A1 | 11/2012 |
| WO | WO 2015/068052 A2 | 5/2015 |
| WO | WO 2016/090287 A2 | 6/2016 |
| WO | WO 2017/055846 A1 | 4/2017 |

(Continued)

OTHER PUBLICATIONS

Stinchcomb et al. Journal of Pharmacy and Pharmacology 2004, 56, 291-297.*
Coulombe et al. The Journal of Clinical Investigation 2009, 119 (7), 1784-1793.*
InMed Pharmaceuticals "InMed Expands Pipeline with Initiation of Program Targeting Epidermolysis bullosa simplex (EBS)", Feb. 3, 2015.*
Amaya et al., "Induction of CB1 cannabinoid receptor by inflammation in primary afferent neurons facilitates antihyperalgesic effect of peripheral CB1 agonist", Pain, vol. 124(1-2), pp. 175-183 (2006).
Annoymous, "CBD For Skin Conditions—Cannabidiol Salve, Balms, Creams", buycbdoilonline, Jun. 13, 2014, pp. 1-8; (URL:http://www.buycbdoilonline. Info/2014/06/cbd-skin-conditions), Retrieved from the Internet on Jan. 31, 2019.

(Continued)

*Primary Examiner* — Irina Neagu
(74) *Attorney, Agent, or Firm* — Todd Lorenz

(57) ABSTRACT

Mutations in keratin genes or the genes that regulate keratin expression can result in epithelial cells lacking sufficient structural integrity. The resulting disruption of connective tissue gives rise to inherited disorders such epidermolysis bullosa. It has been found that various cannabinoids (including mixtures of cannabidiols and cannabinol) upregulate expression of various keratins such that loss of function in other keratin genes may be compensated for. By way of this upregulation, these cannabinoids can be used to treat epidermolysis bullosa and other connective tissue disorders arising from intermediate filament dysfunction.

19 Claims, 27 Drawing Sheets

(56) References Cited

FOREIGN PATENT DOCUMENTS

| WO | WO 2017/158539 A1 | 9/2017 |
|---|---|---|
| WO | WO 2017/190249 A1 | 11/2017 |

OTHER PUBLICATIONS

Appendino G et al. "Antibacterial cannabinoids from Cannabis sativa: a structure-activity study", J Nat Prod., 71:1427-1430 (2008).
Booker et al., "Evaluation of Prevalent Phytocannabinoids in the Acetic Acid Model of Visceral Nociception", Drug Alcohol Depend, vol. 105(1-2), pp. 42-47 (2009).
Bose et al., "Two Mechanisms Regulate Keratin K15 Expression In Keratinocytes: Role of PKC/AP-1 and FOXM1 Mediated Signalling", PLoS One, vol. 7(6):e38599 (2012).
Boukamp et al., "Normal keratinization in a spontaneously immortalized aneuploidy human keratinocyte cell line", J. of Cell Biology, vol. 106, pp. 761-771 (1988).
Chen et al., "Organ-level quorum sensing directs regeneration in hair stem cell populations", Cell, vol. 161(2), pp. 277-290 (2015).
Cosmetic Bench Reference 1996, Cosmetics & Toiletries, published by Allured Publishing Corporation, pp. 1.19-1.22 (1996).
Dvorak et al., "Histamine induced responses are attenuated by cannabinoid receptor agonist in human skin", Inflamm. Res., vol. 52, pp. 238-245 (2003).
Feng et al., "Antagonism of cannabinoid receptor 2 pathway suppresses IL-6-induced immunoglobulin IgM secretion", BMC Pharmacol Toxicol, 15:30 (2014).
Formukong et al., "Analgesic and Antiinflammatory Activity of Constituents of *Cannabis sativa* L.", Inflammation, vol. 12, pp. 361-371 (1988).
Gaffal et al., "Anti-inflammatory activity of topical THC in DNFB-mediated mouse allergic contact dermatitis independent of CB1 and CB2 receptors", Allergy, 68(8):994-1000 (2013).
Gardner et al., "Autocrine and paracrine regulation of lymphocyte CB2 receptor expression by TGF-beta", Biochem Biophys Res Commun., 290(1):91-6 (2002).
Hatzfeld, M & Franke, WW, "Pair Formation and Promiscuity of Cytokeratins: Formation in Vitro of Heterotypic Complexes and Intermediate-sized Filaments by Homologous and Heterologous Recombinations of Purified Polypeptides", J Cell Biol, vol. 101, pp. 1826-1841 (1985).
InMed Pharmaceuticals, "InMed provides update on progress of its development program for epidermolysis bullosa", Nov. 4, 2015, retrieved from https://www.inmedpharma.com/news-media/news/2015/inmed-provides-updated-on-progress-of-its-development-program-for-epidermolysis-bullosa/.
Kozela E et al., "Cannabinoids decrease the th17 inflammatory autoimmune phenotype", J Neuroimmune Pharmacol., 8(5):1265-76 (2013).
Lettner et al., "MMP-9 and CXCL8/IL-8 Are Potential Therapeutic Targets in Epidermolysis Bullosa Simplex", PLoS One, 8(7):e703 (2013).
Lloyd et al. "The Basal Keratin Network of Stratified Squamous Epithelia: Defining K15 Function in the Absence of K14", J Cell Biol., 129: 1329-1344 (1995).
Lodzki et al., "Canabidiol-transdermal delivery and anti-inflammatory effect in a murine model", Journal of Controlled Release, vol. 93, pp. 377-387 (2003).
Mazzalupo et al., "Role for Keratins 6 and 17 During Wound Closure in Embryonic Mouse Skin", Dev Dyn. 226(2): 356-65 (2003).
Paladini et al., "Onset of re-epithelialization after skin injury correlates with a reorganization of keratin filaments in wound edge keratinocytes: defining a potential role for keratin 16", Journal of cell biology, 132:381-397 (1996).
Pini et al., "The role of cannabinoids in inflammatory modulation of allergic respiratory disorders, inflammatory pain and ischemic stroke", Curr Drug Targets, 13(7):984-93 (2012).

Pucci et al., "Epigenetic control of skin differentiation genese by phytocannabinoids", British Journal of Pharmacology, vol. 170, No. 3, pp. 581-591 (2013).
Radoja et al., Thyroid Hormones and Gamma Interferon Specifically Increase K15 Keratin Gene Transcription, Mol Cell Biol:, 24(8): 3168-3179 (2004).
Ramot et al., "A novel control of human keratin expression: cannabinoid receptor 1-mediated signaling down-regulates the expression of keratins K6 and K16 in human keratinocytes in vitro and in situ", Peer J. 19;1:e40 (2013).
Rawal et al., "Effect of cannabidiol on human gingival fibroblast extracellular matrix metabolism: MMP production and activity, and production of fibronectin and transforming growth factor b", J Periodontal Res., 47(3):320-9 (2012).
Richardson et al., "Cannabinoids reduce hyperalgesia and inflammation via interaction with peripheral CB1 receptors", Pain, 75(1):111-9 (1998).
Roth et al., "Cytokines as genetic modifiers in K5−/− mice and in human epidermolysis bullosa simplex", Hum Mutat, 30(5):832-41 (2009).
Rotty and Coulombe, "A wound-induced keratin inhibits Src activity during keratinocyte migration and tissue repair", Journal of Cell Biology, 197:381-389 (2012).
Rueda et al., "The CB1 Cannabinoid Receptor Is Coupled to the Activation of c-Jun N-Terminal Kinase", Mol Pharmacol., 58(4):814-20 (2000).
Ständer et al., "Topical cannabinoid agonists. An effective new possibility for treating chronic pruritus", Hautarzt., 57(9):801-7 (2006).
Teixeira-Clerc et al., "CB1 cannabinoid receptor antagonism: a new strategy for the treatment of liver fibrosis", Nat Med., 12(6):671-6 (2006).
Toth et al., "Endocannabinoids modulate human epidermal keratinocyte proliferation and survival via the sequential engagement of cannabinoid receptor-1 and transient receptor potential vanilloid-1", Journal of Investigational Dermatology, 131: 1095-1104 (2011).
Turner CE and Elsohly MA, "Biological activity of cannabichromene, its homologs and isomers", J Clin Pharmacol., 21(8-9 Suppl):283S-291S (1981).
Uitto et al., "Progress toward Treatment and Cure of Epidermolysis Bullosa: Summary of the DEBRA International Research Symposium EB2015", Journal of Investigative Dermatology, vol. 136, No. 2, pp. 352-358 (2016).
Wagner et al., "Gene expression analysis of an epidermolysis bullosa simplex Dowling-Meara cell line by subtractive hybridization: recapitulation of cellular differentiation, migration and wound healing", Exp Dermatol., 21(2):111-7 (2011).
Wagner et al., "Imbalance of intermediate filament component keratin 14 contributes to increased stress signalling in epidermolysis bullosa simplex", Exp Dermatol., 22(4):292-4 (2013).
Waseem et al., "Keratin 15 Expression in Stratified Epithelia: Downregulation in Activated Keratinocytes", J Invest Dermatol., 112, 362-369 (1999).
Werner S and Munz B, "Suppression of keratin 15 expression by transforming growth factor beta in vitro and by cutaneous injury in vivo", Exp Cell Res., 254(1):80-90 (2000).
Wong and Coulombe, "Loss of keratin 6 (K6) proteins reveals a function for intermediate filaments during wound repair", J Cell Biol., 163(2): 327-337 (2003).
Yang et al., "Effect of chronic CB1 cannabinoid receptor antagonism on livers of rats with biliary cirrhosis", Clin Sci (Lond)., 112(10):533-42 (2007).
Yoshimura et al., "Non-Myeloid Cells are Major Contributors to Innate Immune Responses via Production of Monocyte Chemoattractant Protein-1/CCL2", Front Immunol., 4(482):1-6 (2014).
Zhang et al., "FSP1+ fibroblasts promote skin carcinogenesis by maintaining MCP-1-mediated macrophage infiltration and chronic inflammation", Am J. Pathol., 178(1):382-90 (2011).
Howlett et al., "International Union of Pharmacalogy. XXVII. Classification of Cannabinoid Receptors", Pharmacolgical Reviews, vol. 54, pp. 161-202 (2002).

(56) References Cited

OTHER PUBLICATIONS

Khilnani, G. and Khilnani, A. K., "Inverse Agonism and its therapeutic significance", Indian J. Pharmacol., vol. 43(5), pp. 492-501 (2011).
Perinatology, vol. 44, No. 2, p. 243-245 (2014).
Paudel et al, "Cannabidiol bioavailability after nasal and transdermal application: effect of permeation enhancers", Drug Development and Industrial Pharmacy, vol. 36, No. 9, pp. 1088-1097 (2010).

* cited by examiner

| Major EB Type | Layer of Blistering | Major EB Subtypes | Protein Dysfunction |
|---|---|---|---|
| EB Simplex (EBS) | Epidermis | Basal EBS | - K5, K14<br>- Plectin,<br>α6β4 integrin |
| | | Suprabasal EBS | -desmoplakin |
| Junctional EB (JEB) | Lamina lucida | JEB Herlitz | - Laminin-332 |
| | | JEB, other | - Laminin-332,<br>Type XVII collagen,<br>α6β4 integrin |
| Dystrophic EB (DEB) | Beneath the lamina densa | Dominant DEB (DDEB) | - Type IV collagen |
| | | Recessive (RDEB) | -Type IV collagen |
| Kindler EB (KEB) | Throughout the skin | - | - Kindlin-1 |
| EB Acquisita | Beneath the lamina densa | - | - Type IV collagen |

FIG. 1

| EBS Disease Hallmarks | Phyto-Cannabinoids | Minor Terpenoid Entourage |
|---|---|---|
| Anti-inflammation | CBD, CBG, CBN | Borneol, Caryophyllene, 1,8-Cineole, p-Cymene, Fenchone, α-Humulene, Kaempherol, Limonene, Linoleic acid, α-Linolenic acid, Luteolin, β-Myrcene, Oleic acid, Orientin, α-Pinene, Phytol, Quercetin, Selinene, Sitosterol, Terpinenol-4, N-Trans-Caffeoyltyramine, N-trans-Coumaroyltyramine, N-trans-Feruloyltyramine, Vitexin |
| Anti-Microbes | CBC, CBD, CBG, CBN | Caryophyllene oxide, Camphene, 1,8-Cineole, p-Cymene, Kaempherol, Limonene, Linalool, Nerolidol, α-Pinene, β-Pinene, Phytol, β-Sitosterol, N-Trans-Caffeoyltyramine |
| Anti-Itching | CBD, Δ8-THC | Apigenin, Caryophyllene, Linoleic acid, Luteolin, Quercetin, Phytol |
| Pain-Killing | CBC, CBD, CBG, CBN, Δ9-THC | Borneol, Caryophyllene, p-Cymene, Linalool, β-Sitosterol, Vitexin |
| Wound Healing | CBD, CBG, CBN, Δ8-THC, Δ9-THC | Borneol, Linalool, Kaempherol |

FIG. 3

| Keratins | | INM-509 (μM) | | | INM-505 (μM) | | | INM-506 C (μM) | | | INM-513 (μM) | | |
|---|---|---|---|---|---|---|---|---|---|---|---|---|---|
| | | 0.1 | 1.0 | 10 | 0.1 | 1.0 | 10 | 0.1 | 1.0 | 1.0 | 0.1 | 1.0 | 10 |
| K5 | P | ↓ | - | - | - | - | ↓ | ↓ | - | - | ↓ | - | - |
| K5 | D | - | - | - | - | - | - | - | - | ↓ | ↓ | ↓ | ↓ |
| K14 | P | ↓ | - | - | - | - | ↓ | ↓ | - | - | ↓ | - | ↓ |
| K14 | D | - | - | - | - | - | ↓ | ↓ | - | - | - | - | ↓ |
| K15 | P | ↓ | ↑ | ↑ | ↑ | - | ↑ | ↑ | ↑ | - | ↑ | ↑ | ↑ |
| K15 | D | - | - | ↑ | ↓ | - | - | ↓ | ↓ | ↓ | - | - | - |
| K16 | P | - | - | - | - | - | ↓ | - | - | ↓ | ↑ | - | - |
| K16 | D | - | - | - | - | ↓ | ↓ | - | ↓ | - | - | - | - |

FIG. 4

|  |  | INM-750 | | | | | | | | |
|---|---|---|---|---|---|---|---|---|---|---|
|  |  | 0.1-0.1 µM | | | 0.1-1 µM | | | 1-0.1 µM | | |
|  |  | series 1 | series 2 | series 3 | series 1 | series 2 | series 3 | series 1 | series 2 | series 3 |
| K1 | pre | - | 3.15 | 24.81 | - | 6.06 | 16.11 | - | 4.19 | 16.29 |
| K1 | post | 1.33 | 12.73 | 15.18 | 2.73 | 27.31 | 17.95 | 2.63 | 35.85 | 13.85 |
| K5 | pre | 0.93 | 1.38 | 1.23 | 0.73 | 1.14 | 1.04 | 0.80 | 1.54 | 1.36 |
| K5 | post | 1.21 | 1.36 | 1.81 | 1.43 | 2.10 | 2.09 | 1.60 | 1.76 | 1.60 |
| K6 | pre | 1.43 | 1.04 | 0.81 | 1.59 | 0.88 | 0.70 | 1.40 | 1.53 | 1.13 |
| K6 | post | 1.13 | 0.60 | 0.30 | 1.34 | 1.03 | 0.39 | 1.39 | 0.55 | 0.29 |
| K10 | pre | 2.61 | 0.76 | 8.41 | - | 0.93 | 5.85 | 0.56 | 1.03 | 7.65 |
| K10 | post | 0.50 | 23.36 | 1.07 | 1.35 | 26.67 | 1.38 | 1.73 | 43.74 | 0.92 |
| K14 | pre | 1.24 | 0.35 | 0.48 | 1.08 | 0.27 | 0.28 | 0.88 | 0.52 | 0.49 |
| K14 | post | 0.86 | 0.50 | 0.80 | 0.86 | 0.96 | 0.84 | 0.91 | 0.82 | 0.54 |
| K15 | pre | 1.71 | 3.06 | 4.26 | 0.76 | 4.71 | 3.62 | 0.69 | 3.93 | 2.94 |
| K15 | post | 1.21 | 14.78 | 5.05 | 2.04 | 10.90 | 7.39 | 2.78 | 18.59 | 6.94 |
| K16 | pre | 0.99 | 0.67 | 1.15 | 0.92 | 0.82 | 0.94 | 0.93 | 1.01 | 1.20 |
| K16 | post | 0.82 | 1.48 | 0.26 | 0.76 | 2.44 | 0.43 | 0.72 | 2.03 | 0.40 |
| K17 | pre | 1.02 | 0.38 | 0.52 | 1.16 | 0.31 | 0.34 | 0.92 | 0.41 | 0.50 |
| K17 | post | 1.18 | 1.42 | 1.89 | 1.07 | 2.03 | 2.12 | 1.04 | 2.74 | 1.68 |

Key results:
INM-750- ↓ K14 (pre, post)
INM-750- ↑ K15 (pre, post)
INM-750- ↑ K17 (post)

Potentially desired effect on EBS (-): no expression
grey<1  white =1  1<red

FIG. 5A

| Relative expression of the different keratins in HaCaT keratinocytes- qPCR (internal control: PPIA) ||| INM-750 (1-0.1 µM) ||| INM-751 (0.1-0.1 µM) ||| INM-752 (0.1-1 µM) |||
|---|---|---|---|---|---|---|---|---|---|
| | | series 1 | series 2 | series 3 | series 1 | series 2 | series 3 | series 1 | series 2 | series 3 |
| K1 | pre | - | 4.19 | 16.29 | - | 3.15 | 24.81 | - | 6.06 | 16.11 |
| | post | 2.63 | 35.85 | 13.82 | 1.33 | 12.73 | 15.18 | 2.73 | 27.31 | 17.95 |
| K5 | pre | 0.80 | 1.54 | 1.36 | 0.93 | 1.38 | 1.23 | 0.73 | 1.14 | 1.04 |
| | post | 1.60 | 1.76 | 1.60 | 1.21 | 1.36 | 1.81 | 1.43 | 2.10 | 2.09 |
| K6 | pre | 1.40 | 1.53 | 1.13 | 1.43 | 1.04 | 0.81 | 1.59 | 0.88 | 0.70 |
| | post | 1.39 | 0.55 | 0.29 | 1.13 | 0.60 | 0.30 | 1.34 | 1.03 | 0.39 |
| K10 | pre | 0.56 | 1.03 | 7.65 | 2.61 | 0.76 | 8.41 | - | 0.93 | 5.85 |
| | post | 1.73 | 43.74 | 0.92 | 0.50 | 23.36 | 1.07 | 1.35 | 26.67 | 1.38 |
| K14 | pre | 0.88 | 0.52 | 0.49 | 1.24 | 0.35 | 0.48 | 1.08 | 0.27 | 0.28 |
| | post | 0.91 | 0.82 | 0.54 | 0.86 | 0.50 | 0.80 | 0.86 | 0.96 | 0.84 |
| K15 | pre | 0.69 | 3.93 | 2.94 | 1.71 | 3.06 | 4.26 | 0.76 | 4.71 | 3.62 |
| | post | 2.78 | 18.59 | 6.94 | 1.21 | 14.78 | 5.05 | 2.04 | 10.90 | 7.39 |
| K16 | pre | 0.93 | 1.01 | 1.20 | 0.99 | 0.67 | 1.15 | 0.92 | 0.82 | 0.94 |
| | post | 0.72 | 2.03 | 0.40 | 0.82 | 1.48 | 0.26 | 0.76 | 2.44 | 0.43 |
| K17 | pre | 0.92 | 0.41 | 0.50 | 1.02 | 0.38 | 0.52 | 1.16 | 0.31 | 0.34 |
| | post | 1.04 | 2.74 | 1.68 | 1.18 | 1.42 | 1.89 | 1.07 | 2.03 | 2.12 |
| Potentially Desired effects in EBS ||||||||||| |

FIG. 5B

| Overview of the effects of INM-750 on the keratin expression profile (internal control: β-actin) | | | | | | | | | | |
|---|---|---|---|---|---|---|---|---|---|---|
| | | INM-750 (0.1µM) | | | INM-750 (1µM) | | | INM-750 (10µM) | | |
| | | series 1 | series 2 | series 3 | series 1 | series 2 | series 3 | series 1 | series 2 | series 3 |
| K5 | Pre | 0.41 | 0.35 | 0.94 | 0.37 | 0.32 | 0.45 | 0.43 | 0.38 | 0.40 |
| | Post | 1.01 | 1.05 | 1.04 | 0.15 | 0.99 | 1.34 | 0.15 | 1.97 | 0.34 |
| K6 | Pre | 0.22 | 1.71 | 1.16 | 0.24 | 0.51 | 0.89 | 0.24 | 1.07 | 1.16 |
| | Post | 1.79 | 7.10 | 0.91 | 0.08 | 6.77 | 1.27 | 0.02 | 14.43 | 0.50 |
| K14 | Pre | 0.66 | 1.32 | 1.27 | 0.45 | 0.65 | 1.12 | 0.62 | 1.55 | 1.65 |
| | Post | 1.88 | 0.63 | 1.51 | 0.83 | 0.75 | 1.96 | 0.18 | 0.90 | 0.74 |
| K15 | Pre | 2.42 | 7.71 | 1.56 | 2.49 | 0.30 | 1.38 | 1.96 | 1.60 | 1.28 |
| | Post | 1.24 | 0.76 | 1.27 | 0.44 | 0.78 | 0.64 | 0.33 | 1.01 | 0.79 |
| K16 | Pre | 0.61 | 0.79 | 0.90 | 0.73 | 1.24 | 0.77 | 0.93 | 0.79 | 0.79 |
| | Post | 1.19 | 0.94 | 1.12 | 1.12 | 1.19 | 1.29 | 1.29 | 1.15 | 1.75 |
| K17 | Pre | 0.94 | 1.05 | 0.95 | 0.65 | 1.91 | 0.66 | 0.66 | 1.92 | 0.84 |
| | Post | 1.86 | 1.51 | 1.42 | 0.17 | 1.79 | 1.14 | 0.12 | 1.35 | 0.91 |
| Potentially Desired effect on EBS | | | | | | | | | | |

FIG. 5C

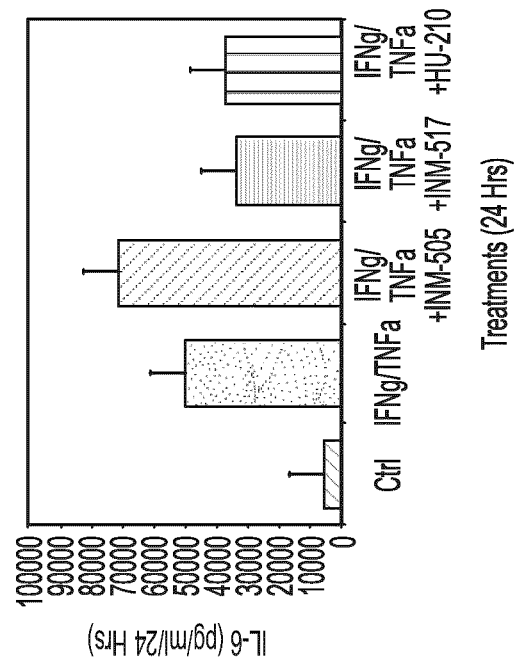
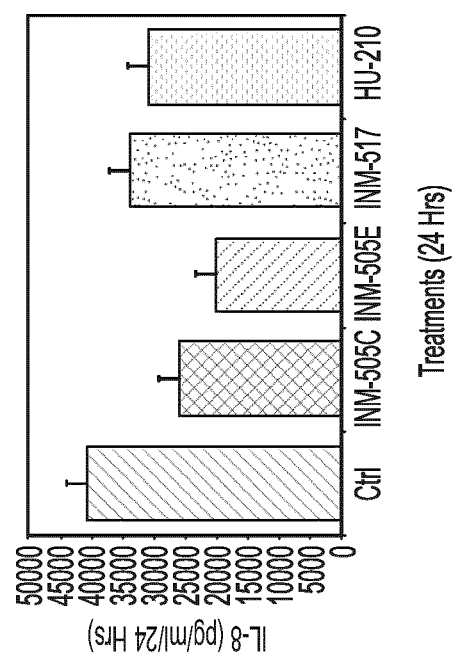
FIG. 13

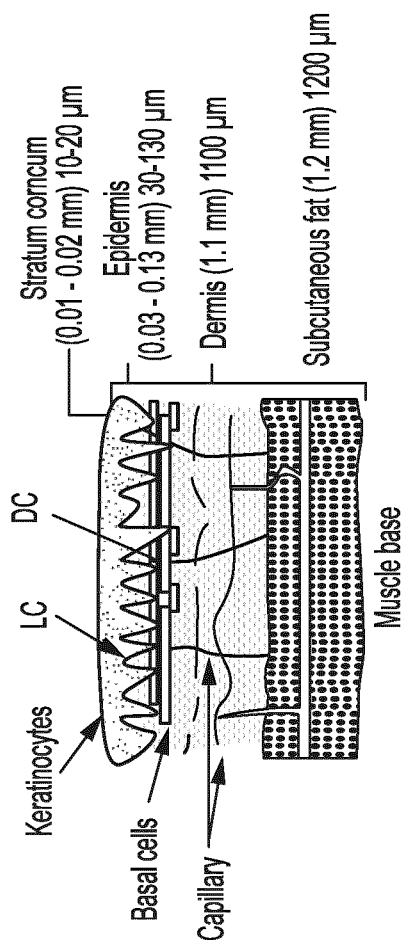
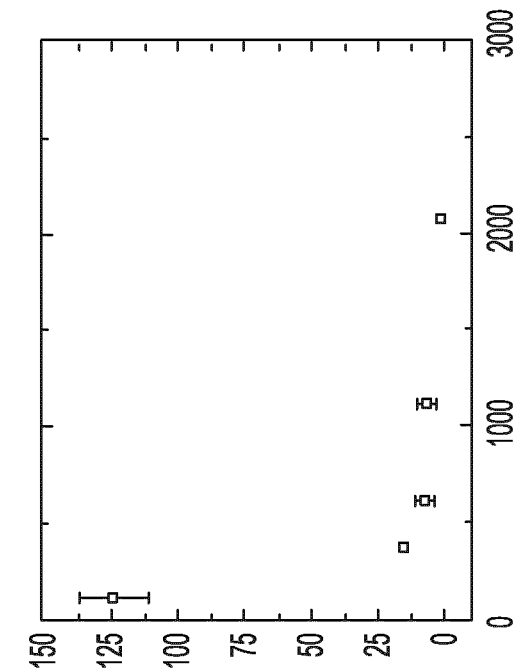
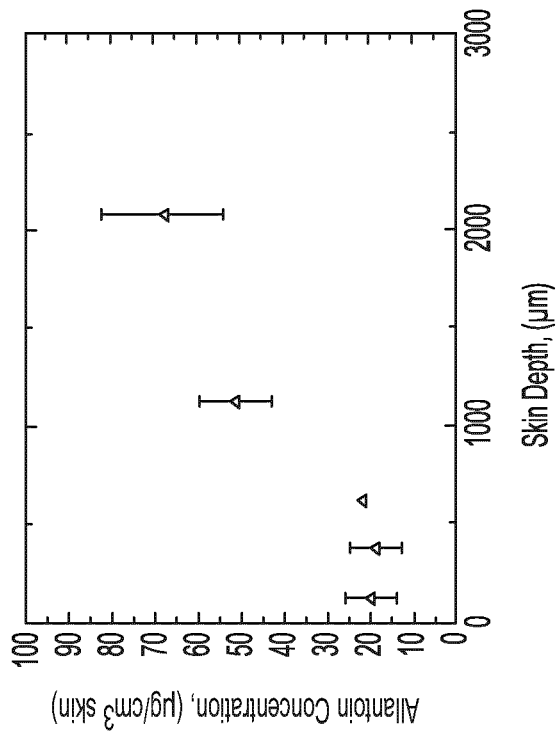
FIG. 18

USE OF TOPICAL FORMULATIONS OF CANNABINOIDS IN THE TREATMENT OF EPIDERMOLYSIS BULLOSA AND RELATED CONNECTIVE TISSUE DISORDERS

CROSS-REFERENCE

This application is a National Phase entry under 371 of International Patent Application PCT/CA2017/050546, filed on 4 May 2017, which claims the benefit of U.S. Provisional Application No. 62/331,633, filed May 4, 2016, the contents of which are hereby incorporated reference in the entirety and for all purposes.

BACKGROUND OF THE INVENTION

This application is directed to methods and compositions for the treatment of diseases and conditions that are associated with intermediate filament dysfunction, particularly employing topical application of cannabinoids. Intermediate filaments are a large group of structurally resilient polymeric proteins that impart mechanical strength to cells. Intermediate filaments are composed of a variety of proteins that are expressed in different cell types. Keratins are a primary structural component of the intermediate filaments in epithelial cells, including epithelial cells of the skin. The human skin consists of two major layers: an outermost layer called the epidermis, and a layer underneath called the dermis. In individuals with healthy skin, there are protein anchors between these two layers that prevent them from moving independently from one another (shearing). Intermediate filaments, and the keratins that form them play an integral role in forming, stabilizing, and maintaining these protein anchors.

Mutations in keratin genes and/or dysregulation of keratin expression can lead to a variety of diseases and conditions of the skin and other epithelial tissues, including but not limited to Epidermolysis Bullosa (EB). Other diseases and conditions related to intermediate filament dysfunction and/or keratin dysfunction include epidermolytic hyperkeratosis, ichthyosis bullosa of Siemens, palmoplantar keratoderma, pachyonychia congenital, white sponge nevus, steatocystoma complex, monilethrix, and Meesman juvenile epithelial corneal dystrophy.

EB is group of inherited connective tissue diseases that share a common manifestation of faulty protein anchors in the skin that result in extremely fragile skin that blisters or tears from friction or trauma. Each type and subtype of the disease is classified based on phenotype, mode of inheritance, and genotype. Over 300 mutations have been identified in EB in the 18 genes that have been found to cause the disorder. Currently, EB is separated into four major subtypes based on where the blisters arise in the skin: (1) epidermolysis bullosa simplex (EBS) (blisters arise within the epidermis); (2) junctional epidermolysis bullosa (JB) (blisters arise within the lamina lucida); (3) dystrophic epidermolysis bullosa (DB) (blisters arise beneath the lamina densa); and (4) Kindler epidermolysis bullosa (KEB) (blisters arise at various levels within the skin. In addition to the inherited forms of the disease there is also an autoimmune form of the disease called epidermolysis bullosa acquisita.

In people born with EB, the two skin layers lack the protein anchors that hold them together, resulting in extremely fragile skin. EB is caused by mutations involving at least 18 genes encoding structural proteins within keratin intermediate filaments, focal adhesions, desmosome cell junctions, and hemidesmosome attachment complexes, which form the intraepidermal adhesion and dermoepidermal anchoring complex within the basement membrane zone (BMZ) of the skin and mucosa. The different categories of EB are characterized by dysfunction in different structural proteins, as shown in FIG. 1. As a result of the protein dysfunction, even minor mechanical friction (like rubbing or pressure) or trauma will separate the layers of the skin and form blisters and painful sores. Sufferers of EB have compared the sores with third-degree burns. Furthermore, as a complication of the chronic skin damage, people suffering from EB have an increased risk of malignancies (cancers) of the skin. A diagram of the structural layers and proteins of the skin showing the components and blistering levels associated with various types of EB is shown in FIG. 2.

The hallmark of EB is mechanical fragility. This is invariably associated with the development of blisters. In most forms of EB, the blisters (or erosions) are filled with clear colorless exudate, or they may be hemorrhagic. The blistering and sores can be painful. In many cases, they leave scars when they heal. The wounds heal slowly and can become infected. Although the blisters often form on the hands and feet, it is not uncommon for them to develop on other parts of the body as well, such as the buttocks or inner thighs, after they have been subjected to friction during activities. Excessive sweating can make the blisters worse. In severe cases, a child can develop up to 200 blisters in a single day. Other primary findings include: milia present as tiny white papules; nails becoming thickened and yellowish, and sometimes with abnormal convex curvature; exuberant granulation tissue, defined as moist, red friable plaques; alopecia of the scalp; congenital absence of the skin (CLAS); albopapuloid lesions; or keratodermas. Secondary lesions include: atrophy; scarring; pigmentary abnormalities; webbing; or contractures.

Epidermolysis bullosa simplex, one of the forms described above, (EBS) is a rare genetic disorder in which the epidermis loses its integrity following trivial mechanical trauma. In EBS, blister formation occurs at the dermoepidermal junction. EBS is caused, in most cases, by a mutation in the gene encoding keratin 5 or keratin 14; typically these mutations are missense mutations.

EBS may be divided into a number of types. Epidermolysis bullosa simplex with migratory circinate erythema is associated with a mutation in KRT5 at 12q13. Epidermolysis bullosa simplex with mottled pigmentation is associated with a mutation in KRT5 at 12q13 and is also associated with a recurrent mutation in KRT14. Epidermolysis bullosa simplex, autosomal recessive, is associated with a mutation in KRT14 at 17q12-q21. Generalized epidermolysis bullosa simplex, also known as "Koebner variant of epidermolysis bullosa simplex," presents at birth to early infancy with a predilection for the hands, feet, and extremities, and palmarplantar hyperkeratosis and erosions may be present; it is associated with a mutation in KRT5 at 17q12-q21 and in KRT14 at 12q13. Localized epidermolysis bullosa simplex, also known as "Weber-Cockayne syndrome" and "Weber-Cockayne variant of generalized epidermolysis bullosa simplex," is characterized by onset in childhood or later in life, and is the most common variant of epidermolysis bullosa simplex, and is associated with a mutation in KRT5 at 17q12-q21 and in KRT14 at 17q11-qter, 12q13. Epidermolysis bullosa simplex herpetiformis, also known as "Dowling-Meara epidermolysis bullosa simplex," presents at birth with a generalized distribution, often with oral mucosa involvement and variable lesions in infancy, and is associated with a mutation in KRT5 at 17q12-q21 and a mutation in KRT14 at 12q13. Epidermolysis bullosa simplex with muscular dystrophy is a rare clinical entity and is one of only a few variants of epidermolysis bullosa simplex not associated with a mutation in a keratin gene; it presents as a generalized intraepidermal blistering similar to the Koebner variant of epidermolysis bullosa simplex but is also associated with adult onset muscular dystrophy, and is associated with a mutation in PLEC1 at 8q24. Also associated with a mutation in PLEC1 at 8q24 are epidermolysis bullosa simplex with pyloric atresia and epidermolysis bullosa simplex of Ogna, which has its onset in infancy and presents with seasonal blistering on acral areas during the summer months.

Epidermolysis bullosa simplex is characterized by extreme fragility of the keratinocytes and skin blistering. In the variants characterized by a mutation in either or both of KRT5 or KRT14, the disease results from results from missense mutations in the gene that encodes keratin 5 (K5) or keratin 14 (K14). K5 and K14, which are abundant cellular proteins, normally co-polymerize to form an intricate network of 10-12 nm-wide, "intermediate-sized" filaments in basal keratinocytes of the epidermis and related epithelia. EBS may manifest itself as a relatively mild blistering condition involving the hands and feet, or as a generalized blistering condition, sometimes associated with mucosal blistering that involves the oropharynx, the esophagus and ocular mucosa. The more severe forms of EBS may lead to scarring, disfigurement, disability and early death, usually before the age of 30.

Management of EBS generally consists of supportive care to protect the skin from blistering and prevention and treatment of secondary infection. Typically, such treatment is similar to that given to burn victims, and may include application of non-adherent bandages, dressings, and antiseptic washes for the blisters, various medications for pain, itching, and inflammation, and oral antibiotics for infections. Preventative treatments such as aluminum chloride and botulinum toxin A to prevent sweating can be used. Care options available to EBS patients are wound care, pain management, and preventive bandaging. These care options for EBS patients are palliative and have limited success. Other treatment methods, such as the administration of sulforaphane or the use of bone marrow transplants, have been proposed, but have limited application; in particular, bone marrow transplants not only require a genetically compatible donor but also require the administration of strong immunosuppressants that drastically increase the risk of serious infections in patients with large-scale blistering and skin erosions. Therefore, it is desirable to develop and provide compositions and methods for treating EBS. There is a particular need to modify the course of the disease by restoring the anchoring functions that have been lost due to dysfunctional proteins, especially keratin 5 and keratin 14. Additionally, there is a particular need to treat the symptoms of the disease, with a specific focus on healing the blisters that form as a result of mechanical friction in the course of the disease.

SUMMARY OF THE INVENTION

The present invention provides improved methods and compositions for the treatment of diseases and conditions associated with intermediate filament dysfunction. In particular, the present invention provides improved methods and compositions for topical treatment of such diseases and conditions. Such diseases and conditions include, but are not limited to those associated with, or caused or exacerbated by, a dysfunction in one or more keratins. For example, the methods and compositions described herein can be used to treat one or more types of epidermolysis bullosa (EB), including but not limited to epidermolysis bullosa simplex (EBS).

Without wishing to be bound by theory, it is believed that the present invention provides beneficial treatment at least in part because, as described herein, topical application of one or more cannabinoids can regulate the synthesis of keratin. In some cases, the topical application of one or more cannabinoids can increase the transcription, protein synthesis, and/or activity of one or more keratins to a sufficient degree to at least partially compensate for a loss of function mutation in the same keratin gene, a different endogenous keratin gene, or a protein that associates with, binds to, or anchors keratin containing intermediate filaments. In some cases, the topical application of one or more cannabinoids can increase the transcription, protein synthesis, and/or activity of one or more keratins to a sufficient degree to at least partially compensate for a dominant negative mutation in a different endogenous keratin gene. In some cases, the topical application of one or more cannabinoids can decrease transcription, protein synthesis, and/or activity of one or more, e.g., dominant negative, keratin mutants, and/or increase the transcription, protein synthesis, and/or activity of one or more wild-type keratins to a sufficient degree to at least partially compensate for a, e.g., dominant negative, mutation in an endogenous keratin gene.

In some embodiments, the methods and compositions described herein can be used for topical treatment of diseases and conditions associated with intermediate filament dysfunction by upregulation of transcription, protein synthesis, and/or activity of certain sub-types of keratin associated with mitigation of the disease or condition and/or downregulation or inhibition of activity, transcription, or protein synthesis of other sub-types of keratin associated with the disease or condition. In some cases, additional agents, such as terpenoids can be employed.

One aspect of the present invention is a method for treating a disease or condition associated with intermediate filament dysfunction. In some embodiments, the disease or condition is a skin disease or condition. In some embodiments, the disease or condition is epidermolysis bullosa (EB). In some embodiments, the disease or condition is epidermolysis bullosa simplex (EBS). The method can comprises the step of administering a therapeutically effective quantity of a cannabinoid to a patient with a disease or condition selected from the group consisting of EB, EBS, epidermolytic hyperkeratosis, ichthyosis bullosa of Siemens, palmoplantar keratoderma, pachyonychia congenital, white sponge nevus, steatocystoma complex, monilethrix, and Meesman juvenile epithelial corneal dystrophy to thereby treat the disease or condition. Typically, the method accomplishes at least one of: reducing inflammation; promoting wound healing and skin or corneal regeneration; reducing pain and itching; reducing the occurrence of infection; and reducing corneal cysts.

Typically, the therapeutically effective quantity of a cannabinoid is a mixture of cannabidiols and cannabinol selected from the group consisting of cannabidiols:cannabinol (1:0.1 µM), cannabidiols:cannabinol (0.1:1 µM), and cannabidiols:cannabinol (1:1 µM). Preferably, the therapeutically effective quantity of a cannabinoid is cannabidiols:cannabinol (1:0.1 µM). In the alternative, other ratios can be used.

Alternatively, other cannabinoids, including synthetic cannabinoids, endocannabinoids, and analogs and derivatives of such cannabinoids, can be used. In one alternative, the cannabinoid is selected from the group consisting of classical cannabinoids, non-classical cannabinoids, aminoalkylindoles and eicosanoids. The classical cannabinoid, non-classical cannabinoid, aminoalkylindole, or eicosanoid can be selective for the CB1 receptor. Alternatively, the classical cannabinoid, non-classical cannabinoid, aminoalkylindole, or eicosanoid can be non-selective for CB1 and CB2 cannabinoid receptors.

The cannabinoid can be administered in a pharmaceutical composition including at least one pharmaceutically acceptable carrier for topical administration of the composition. In one preferred alternative, the pharmaceutically acceptable carrier is at least one pharmaceutically acceptable carrier selected from the group consisting of LABRASOL® (caprylocaproyl polyoxyl-8 glycerides), poloxamer 407, lecithin, and isopropyl palmitate. In a more highly preferred alternative, the pharmaceutically acceptable carrier is LABRASOL®, poloxamer 407, lecithin, and isopropyl palmitate.

The pharmaceutical composition can include at least one excipient. Typically, the excipient is selected from the group consisting of: preservatives; thickening agents; buffers; liquid carriers; isotonic agents; wetting, solubilizing, and emulsifying agents; acidifying agents; antioxidants; alkalinizing agents; carrying agents; chelating agents; complexing agents; solvents; suspending or viscosity-increasing agents; oils; penetration enhancers; polymers; stiffening agents; proteins; carbohydrates; and bulking agents.

The composition can further comprise: a topical anti-inflammatory agent; a topical anti-bacterial agent; a topical anti-fungal agent; a topical steroid; or a topical antioxidant.

In some embodiments, the method can further comprise the step of topically administering an additional therapeutically active agent to treat the disease or condition. The additional therapeutically active agent can be selected from the group consisting of a topical anti-inflammatory agent, a topical anti-bacterial agent, a topical anti-fungal agent, a topical steroid, and a topical antioxidant.

In some embodiments, the method can further comprise the step of topically administering a therapeutically effective quantity of a terpenoid. At least one classical cannabinoid, non-classical cannabinoid, aminoalkylindole, or eicosanoid and at least one terpenoid can be administered in a single pharmaceutical composition; alternatively, the cannabinoid and the terpenoid can be administered separately. Various combinations of terpenoids that can be used in combination with a classical cannabinoid, non-classical cannabinoid, aminoalkylindole, or eicosanoid are described to achieve specific therapeutic effects.

Another aspect of the invention is a topical pharmaceutical composition for treating a disease or condition associated with intermediate filament dysfunction (e.g., epidermolysis bullosa simplex (EBS)) comprising:

(1) a therapeutically effective quantity of a cannabinoid; and
(2) at least one pharmaceutically acceptable carrier for topical administration of the composition to treat the disease or condition (e.g., EBS).

Typically, administration of the composition accomplishes at least one of: reducing inflammation; promoting wound healing and skin or corneal regeneration; reducing pain and itching; reducing the occurrence of infection; and reducing corneal cysts.

Preferred cannabinoids include a mixture of one or more cannabidiols and cannabinol selected from the group consisting of cannabidiols:cannabinol (1:0.1 µM), cannabidiols:cannabinol (0.1:1 µM), and cannabidiols:cannabinol (1:1 µM). A particularly preferred combination of cannabinoids in a composition according to the present invention is cannabidiols:cannabinol (1:0.1 µM). Other ratios of cannabidiols and cannabinol can be employed. Other cannabinoids, including synthetic cannabinoids, endocannabinoids, and derivatives and analogs of cannabinoids as described above with respect to methods according to the present invention.

Suitable pharmaceutically acceptable carriers for topical administration of the composition include those described above with respect to methods according to the present invention. As stated above, a particularly preferred pharmaceutically acceptable carrier is LABRASOL® (caprylocaproyl polyoxyl-8 glycerides), poloxamer 407, lecithin, and isopropyl palmitate.

Pharmaceutical compositions according to the present invention can further comprise at least one excipient such as one of the excipients described above with respect to methods according to the present invention. Typically, the excipient is selected from the group consisting of preservatives; thickening agents; buffers; liquid carriers; isotonic agents; wetting, solubilizing, and emulsifying agents; acidifying agents; antioxidants; alkalinizing agents; carrying agents; chelating agents; complexing agents; solvents; suspending or viscosity-increasing agents; oils; penetration enhancers; polymers; stiffening agents; proteins; carbohydrates; and bulking agents as described above.

In some embodiments, pharmaceutical compositions according to the present invention can further comprise a topical emollient, a topical anti-inflammatory agent, a topical anti-bacterial agent, a topical anti-fungal agent, a topical steroid, or a topical antioxidant as described above with respect to methods according to the present invention.

In some embodiments, pharmaceutical compositions according to the present invention can comprise a combination of a cannabinoid and a terpenoid as described herein with respect to methods according to the present invention.

In some embodiments, particularly preferred combinations of cannabinoids and terpenoids are described herein with reference to the therapeutic activity of the composition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

FIG. 1 is a diagram showing the different categories of epidermolysis bullosa (EB) and their association with specific dysfunctional proteins.

FIG. 3 is a table illustrating EBS disease hallmarks, and corresponding exemplary compositions containing the indicated phytocannabinoids and terpenoids suitable for treatment of said hallmarks in a method described herein or suitable in a pharmaceutical composition described herein.

FIG. 4 is a table showing the effects of individual cannabinoids on the expression of K5, K14, K15 and K16 in HaCaT keratinocytes.

FIG. 5A is a table showing the effect of different concentrations of CBD:CBN at a 10:1 ratio on keratin expression profile.

FIG. 5B is a table showing the relative expression of different keratins in HaCaT keratinocytes with different concentrations of CBD:CBN as determined by qPCR (the internal control is PPIA).

FIG. 5C is a table showing the effect of different concentrations of CBD:CBN at a 10:1 ratio on keratin expression profile (the internal control is β-actin).

FIG. 13 illustrates strong inhibitory effects of cannabinoids on inflammation. (Left) a graph showing that cannabinoids display strong inhibitory effects on IL-6 production induced by pro-inflammatory agents in human keratinocytes. (Right) a graph showing that cannabinoids also inhibit basal IL-8 production, a biomarker of inflammation.

FIG. 18 illustrates skin and skin penetraton profiles. (top panel) a schematic diagram of the skin (LC: Langerhans cells; DC: dendritic cells; capillary networks). (bottom left panel) the allantoin skin penetration profile (x-axis, skin depth, μm; y-axis, allantoin concentration, μg/cm$^3$ skin). (bottom right panel) the cannabidiol skin penetration profile (x-axis, skin depth, μm; y-axis, cannabidiol concentration, μg/cm$^3$ skin).

DETAILED DESCRIPTION OF THE INVENTION

Figure 2:
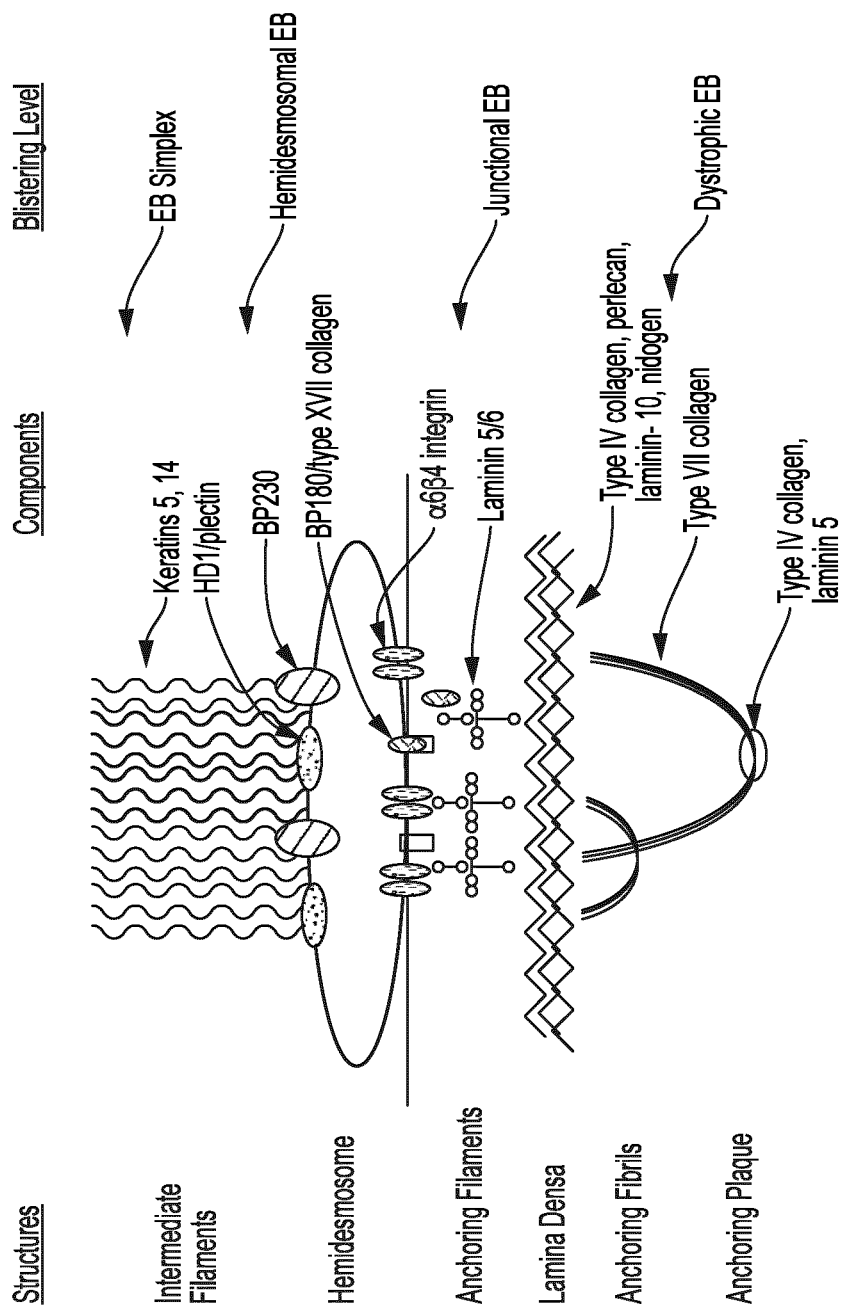
FIG. 2 is a diagram of the structural layers and proteins of the skin showing the components and blistering levels associated with various types of EB.

The present invention provides compositions and methods for the treatment of diseases and conditions associated with dysfunction of intermediate filaments, particularly intermediate filaments of epithelial cells or tissues containing such epithelial cells. Such diseases and conditions include those caused by dysregulated transcription, protein synthesis, and/or activity of certain keratins (e.g., due to autoimmune or genetic disorders). Such diseases and conditions include, but are not limited to, the sub-types of epidermolysis bullosa (EB) including epidermolysis bullosa simplex (EBS), epidermolytic hyperkeratosis, ichthyosis bullosa of Siemens, palmoplantar keratoderma, pachyonychia congenital, white sponge nevus, steatocystoma complex, monilethrix, and Meesman juvenile epithelial corneal dystrophy. The present invention is based at least in part on the surprising discovery that cannabinoids can modulate the expression of keratin genes, including the genes coding for K5, K14, and K15 to a therapeutically relevant degree.

Definitions

As used herein, the term "modulate an amount or activity of one or more keratins" refers to a change (e.g., increase or decrease) in mRNA amount, protein amount, or intermediate filament formation activity, of one or more keratin genes or gene products.

The following terminology is used herein for cannabinoids and mixtures thereof: "INM-750" is a 10:1 ratio of cannabidiols and cannabinol at a ratio of 1:0.1 µM. "INM-751" is a 1:10 mixture of cannabidiols and cannabinol at a ratio of 0.1:1 µM. "INM-752" is a 1:1 mixture of cannabidiols and cannabinol at a ratio of 1:1 µM. "INM-505" is cannabidiols (INM-505C is the synthetic version of cannabidiols (CBD) from Cyman Pharmaceuticals and "INM-505E" is extracted from natural cannabinoid extract from Eacho Pharmaceuticals). "INM-506" is cannabidiolic acid. "INM-509" is cannabichromene (CBC). "INM-513" is cannabigerol (CBG). "INM-517" is cannabinol. Each of the foregoing INM compositions are free of, or substantially (>99.9%) free of delta-9-tetrahydrocannabinol. In a preferred embodiment, all cannabinoids, and mixtures thereof are free of, or substantially (>99.9%) free of psychoactive cannabinoids. In another embodiment, all cannabinoids, and mixtures thereof contain an amount of psychoactive cannabinoids that is below an amount that provides a discernable psychoactive effect when administered to a subject, or when administered to a subject at a therapeutic dose, or when topically administered to a subject (e.g., at a therapeutic dose).

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

As used herein, the term "lower alkyl" or equivalent terminology, without further limitation, refers to $C_1$-$C_6$ groups and, e.g., includes methyl. The term "lower alkyl" can be further limited, such as "$C_2$-$C_6$ lower alkyl," which excludes methyl. The term "lower alkyl", unless further limited, refers to both straight-chain and branched alkyl groups. These lower alkyl groups can be unsubstituted or substituted, as described below.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene. Alkenylen groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene. Alkynylene groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted. The term "lower alkoxy" refers to an alkoxy group in which the alkyl portion of the alkoxy group is $C_1$-$C_6$.

"Alkylhydroxy" refers to an alkyl group, as defined above, where at least one of the hydrogen atoms is replaced with a hydroxy group. As for the alkyl group, alkylhydroxy groups can have any suitable number of carbon atoms, such as $C_{1-6}$. Exemplary alkylhydroxy groups include, but are not limited to, hydroxy-methyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), hydroxypentyl (where the hydroxy is in the 1-, 2-, 3-, 4- or 5-position), hydroxyhexyl (where the hydroxy is in the 1-, 2-, 3-, 4-, 5- or 6-position), 1,2-dihydroxyethyl, and the like.

"Heteroalkyl" refers to an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroatom portion can be the connecting atom, or be inserted between two carbon atoms.

"Heteroalkylene" refers to a heteroalkyl group, as defined above, linking at least two other groups. The two moieties linked to the heteroalkylene can be linked to the same atom or different atoms of the heteroalkylene.

"Halogen," "halo group," and the like refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-9}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Cycloalkylene" refers to a cycloalkyl group having the number of carbon atoms indicated, and linking at least two other groups, i.e., a divalent radical. The two moieties linked to the cycloalkylene can be linked to the same atom or different atoms of the cycloalkylene group. Examples of cycloalkylene rings include cyclopropylene, cyclobutylene, cyclopentylene and cyclohexylene, among others. Cycloalkylene groups can be linked 1,1, 1,2, 1,3, or 1,4. The cyclohexylene ring, for example, can adopt a number of conformations, including the boat and chair conformations. The chair conformation of cyclohexylene can have substituents in an axial or equatorial orientation. The divalent nature of the cycloalkylenes results in cis and trans formations where cis refers to both substituents being on the same side (top or bottom) of the cycloalkylene ring, and where trans refers to the substituents being on on opposite sides of the cycloalkylene ring. For example, cis-1,2- and cis-1,4-cyclohexylene can have one substituent in the axial orientation and the other substituent in the equatorial orientation, while trans-1,2- and trans-1,4-cyclohexylene have both substituents in the axial or equatorial orientation. cis-1,3-cyclohexylene have both substituents in the axial or equatorial orientation, and trans-1,3-cyclohexylene can have one substituent in the axial orientation and the other substituent in the equatorial orientation. Cycloalkylene groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Heterocyclalkylene" refers to a heterocyclalkyl group, as defined above, linking at least two other groups. The two moieties linked to the heterocyclalkylene can be linked to the same atom or different atoms of the heterocyclalkylene. Heterocycloalkylene groups can be substituted or unsubstituted.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroarylene" refers to a heteroaryl group, as defined above, linking at least two other groups. The two moieties linked to the heteroaryl are linked to different atoms of the heteroaryl. Heteroarylene groups can be substituted or unsubstituted.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

"Amine" or "amino" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Alkyl amine" refers to an alkyl group as defined within, having one or more amino groups. The amino groups can be primary, secondary or tertiary. The alkyl amine can be further substituted with a hydroxy group to form an aminohydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Carboxy" refers to a carboxylic acid group of the formula —C(O)OH or —CO$_2$H. "Carboxyalkyl" refers to a carboxy group linked to an alkyl, as described above, and generally having the formula —C$_{1-8}$ alkyl-C(O)OH. Any suitable alkyl chain is useful.

As used herein, the term "sulfo" refers to a sulfonic acid (—SO$_3$H) substituent. As used herein, the term "sulfamoyl" refers to a substituent with the structure —S(O$_2$)NH$_2$, wherein the nitrogen of the NH$_2$ portion of the group can be optionally substituted as described herein. As used herein, the term "carbamyl" refers to a group of the structure —C(O$_2$)NH$_2$, wherein the nitrogen of the NH$_2$ portion of the group can be optionally substituted as described herein. As used herein, the terms "monoalkylaminoalkyl" and "dialkylaminoalkyl" refer to groups of the structure -Alk$_1$-NH-Alk$_2$ and -Alk$_1$-N(Alk$_2$)(Alk$_3$), wherein Alk$_1$, Alk$_2$, and Alk$_3$ refer to alkyl groups as described herein.

As used herein, the term "alkylsulfonyl" refers to a group of the structure —S(O)$_2$-Alk wherein Alk refers to an alkyl group as described herein. The terms "alkenylsulfonyl" and "alkynylsulfonyl" refer analogously to sulfonyl groups covalently bound to alkenyl and alkynyl groups, respectively. The term "arylsulfonyl" refers to a group of the structure —S(O)$_2$—Ar wherein Ar refers to an aryl group as described herein. The term "aryloxyalkylsulfonyl" refers to a group of the structure —S(O)$_2$-Alk-O—Ar, where Alk is an alkyl group as described herein and Ar is an aryl group as described herein. The term "arylalkylsulfonyl" refers to a group of the structure —S(O)$_2$-AlkAr, where Alk is an alkyl group as described herein and Ar is an aryl group as described herein.

As used herein, the term "alkyloxycarbonyl" refers to an ester substituent including an alkyl group wherein the carbonyl carbon is the point of attachment to the molecule. An example is ethoxycarbonyl, which is CH$_3$CH$_2$OC(O)—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

The groups defined above, such as those present in the cannabinoid and/or terpenoid compounds described below, can optionally be substituted by any suitable number and type of substituents. Representative substituents include, but are not limited to, halogen, haloalkyl, haloalkoxy, —OR', =O, —OC(O)R', —(O)R', —O$_2$R', —ONR'R'', —OC(O)NR'R'', =NR', =N—OR', —NR'R'', —NR''C(O)R', —NR'—(O)NR''R''', —NR''C(O)OR', —NH—(NH$_2$)=NH, —NR'C(NH$_2$)=NH, —NH—(NH$_2$)=NR', —SR', —S(O)R', —S(O)$_2$R', —S(O)$_2$NR'R'', —NR'S(O)$_2$R'', —N$_3$ and —NO$_2$. R', R'' and R''' each independently refer to hydrogen, unsubstituted alkyl, such as unsubstituted C$_{1-6}$ alkyl. Alternatively, R' and R'', or R'' and R''', when attached to the same nitrogen, are combined with the nitrogen to which they are attached to form a heterocycloalkyl or heteroaryl ring, as defined above. This cannot be taken to limit the possibility of further optional substituents. Further descriptions of potential additional optional substituents are provided below. Optional substituents typically do not substantially decrease the activity of the compound or the stability of the compound in which they are present, particularly the activity or stability of the compound when present in a pharmaceutical composition as described herein. In some cases, optional substituents increase activity, stability, solubility, and/or bioavailability of the compound when present in a pharmaceutical composition as described herein The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other alternatives for stereoisomers) as well as mixtures of stereoisomers in varying degrees of chiral purity or percentage of E and Z, including racemic mixtures, mixtures of diastereomers, and mixtures of E and Z isomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted isomer. When the chemical name does not specify the isomeric form of the compound, it denotes any one of the possible isomeric forms or mixtures of those isomeric forms of the compound. The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium; the equilibrium may strongly favor one of the tautomers, depending on stability considerations. For example, ketone and enol are two tautomeric forms of one compound.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention. In general, all physical forms are intended to be within the scope of the present invention.

Thus, when a therapeutically active agent used in a method according to the present invention or included in a composition according to the present invention, such as, but not limited to, a cannabinoid or a terpenoid, possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, p-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such asp-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

"Composition" as used herein is intended to encompass a product comprising the specified ingredients in the specified amounts, as well as any product that results from combination of the specified ingredients in the specified amounts. By "pharmaceutically acceptable" it is meant the carrier, diluent or excipient must be compatible with the other ingredients of the formulation and deleterious to the recipient thereof.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

In some cases, protecting groups can be included in compounds used in methods according to the present invention or in compositions according to the present invention. The use of such a protecting group is to prevent subsequent hydrolysis or other reactions that can occur in vivo and can degrade the compound. Groups that can be protected include alcohols, amines, carbonyls, carboxylic acids, phosphates, and terminal alkynes. Protecting groups useful for protecting alcohols include, but are not limited to, acetyl, benzoyl, benzyl, β-methoxyethoxyethyl ether, dimethoxytrityl, methoxymethyl ether, methoxytrityl, p-methoxybenzyl ether, methylthiomethyl ether, pivaloyl, tetrahydropyranyl, tetrahydrofuran, trityl, silyl ether, methyl ether, and ethoxyethyl ether. Protecting groups useful for protecting amines include carbobenzyloxy, p-methoxybenzylcarbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, trichloroethyl chloroformate, and sulfonamide. Protecting groups useful for protecting carbonyls include acetals, ketals, acylals, and dithianes. Protecting groups useful for protecting carboxylic acids include methyl esters, benzyl esters, t-butyl esters, esters of 2,6-disubstituted phenols, silyl esters, orthoesters, and oxazoline. Protecting groups useful for protecting phosphate groups include 2-cyanoethyl and methyl. Protecting groups useful for protecting terminal alkynes include propargyl alcohols and silyl groups. Other protecting groups are known in the art.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity. Thus, the term "prodrug" refers to a precursor of a biologically active compound that is pharmaceutically acceptable. n certain cases, a prodrug has improved physical and/or delivery properties over a parent compound from which the prodrug has been derived. The prodrug often offers advantages of solubility, tissue compatibility, or delayed release in a mammalian organism (H. Bundgard, *Design of Prodrugs* (Elsevier, Amsterdam, 1988), pp. 7-9, 21-24). A discussion of prodrugs is provided in T. Higuchi et al., "Pro-Drugs as Novel Delivery Systems," *ACS Symposium Series*, Vol. 14 and in E. B. Roche, ed., *Bioreversible Carriers in Drug Design* (American Pharmaceutical Association & Pergamon Press, 1987). Exemplary advantages of a prodrug can include, but are not limited to, its physical properties, such as enhanced drug stability for long-term storage.

The term "prodrug" is also meant to include any covalently bonded carriers which release the active compound in vivo when the prodrug is administered to a subject. Prodrugs of a therapeutically active compound, as described herein, can be prepared by modifying one or more functional groups present in the therapeutically active compound, including cannabinoids, terpenoids, and other therapeutically active compounds used in methods according to the present invention or included in compositions according to the present invention, in such a way that the modifications are cleaved, either in routine manipulation or in vivo, to yield the parent therapeutically active compound. Prodrugs include compounds wherein a hydroxy, amino, or mercapto group is covalently bonded to any group that, when the prodrug of the active compound is administered to a subject, cleaves to form a free hydroxy, free amino, or free mercapto group, respectively. Examples of prodrugs include, but are not limited to, formate or benzoate derivatives of an alcohol or acetamide, formamide or benzamide derivatives of a therapeutically active agent possessing an amine functional group available for reaction, and the like.

For example, if a therapeutically active agent or a pharmaceutically acceptable form of a therapeutically active agent contains a carboxylic acid functional group, a prodrug can comprise an ester formed by the replacement of the hydrogen atom of the carboxylic acid group with a group such as $C_{1-8}$ alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N($C_1$-$C_2$)alkylamino($C_2$-$C_3$)alkyl (such as (3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino-, or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$))alkanoyloxy) ethyl, 1-methyl-1-(($C_1$-$C_6$)alkanoyloxy)ethyl ($C_1$-$C_6$) alkoxycarbonyloxymethyl, N($C_1$-$C_6$)alkoxycarbonylaminomethyl, succinoyl, ($C_1$-$C_6$)alkanoyl, α-amino($C_1$-$C_4$) alkanoyl, arylacyl and α-aminoacyl, or α-aminoacyl-α-aminoacyl, where each α-aminoacyl group is independently selected from the naturally occurring L-amino acids, P(O) (OH)$_2$, P(O)(O($C_1$-$C_6$)alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, C(OH)C(O)OY$^1$ wherein Y$^1$ is H, ($C_1$-$C_6$)alkyl or benzyl, C(OY$^2$)Y$^3$ wherein Y$^2$ is ($C_1$-$C_4$) alkyl and Y$^3$ is ($C_1$-$C_6$)alkyl, carboxy($C_1$-$C_6$) alkyl, amino($C_1$-$C_4$)alkyl or mono-N or di-N,N($C_1$-$C_6$)alkylaminoalkyl, C(Y$^4$)Y$^5$ wherein Y$^4$ is H or methyl and Y$^5$ is mono-N or di-N,N($C_1$-$C_6$)alkylamino, morpholino, piperidin-1-yl or pyrrolidin-1-yl.

The use of prodrug systems is described in T. Järvinen et al., "Design and Pharmaceutical Applications of Prodrugs" in *Drug Discovery Handbook* (S. C. Gad, ed., Wiley-Interscience, Hoboken, N J, 2005), ch. 17, pp. 733-796. Other alternatives for prodrug construction and use are known in the art. When a method or pharmaceutical composition according to the present invention, uses or includes a prodrug of a cannabinoid, terpenoid, or other therapeutically active agent, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

As used herein, the terms "treating," "treatment," and similar terminology refer to any detectable improvement, whether subjective or objective, in the pathology caused by or associated with a disease or condition associated with an intermediate filament dysfunction (e.g., EBS) for a subject to whom a composition according to the present invention was administered. For example, the terms "treating," "treatment," and similar terminology can refer to a decrease in pain, a decrease in blistering, a decrease in scarring, a decrease in frequency or severity of secondary infection, a decrease in systemic complications such as mucosal blistering that involves the oropharynx, the esophagus and ocular mucosa, an improvement in wound healing, a decrease in itching, a decrease in corneal cysts, an increase in perceived well-being or psychological feelings of wellness, or other subjective or objective criteria. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. The results of treatment can be determined by methods known in the art. The terms "treating," "treatment," and similar terminology do not imply a cure for the disease or condition to be treated. For the purposes of the present application, treatment can be monitored by observing one or more of the improving symptoms associated with the disease, disorder, or condition being treated, or by observing one or more of the improving clinical parameters associated with the disease, disorder, or condition being treated, as described above.

As used herein, the terms "therapeutically effective quantity" or "therapeutically effective dose" dose refer to a dose of one or more compositions described herein that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the terms "cannabidiol," "CBD," or "cannabidiols" refer to one or more of the following compounds, and, unless a particular other stereoisomer or stereoisomers are specified, includes the compound "$\Delta^2$-cannabidiol." These compounds are: (1) $\Delta^5$-cannabidiol (2-(6-isopropenyl-3-methyl-5-cyclohexen-1-yl)-5-pentyl-1,3-benzenediol); (2) $\Delta^4$-cannabidiol (2-(6-isopropenyl-3-methyl-4-cyclohexen-1-yl)-5-pentyl-1,3-benzenediol); (3) $\Delta^3$-cannabidiol (2-(6-isopropenyl-3-methyl-3-cyclohexen-1-yl)-5-pentyl-1,3-benzenediol); (4) $\Delta^{3,7}$-cannabidiol (2-(6-isopropenyl-3-methylenecyclohex-1-yl)-5-pentyl-1,3-benzenediol); (5) $\Delta^2$-cannabidiol (2-(6-isopropenyl-3-methyl-2-cyclohexen-1-yl)-5-pentyl-1,3-benzenediol); (6) $\Delta^1$-cannabidiol (2-(6-isopropenyl-3-methyl-1-cyclohexen-1-yl)-5-pentyl-1,3-benzenediol); and (7) $\Delta^6$-cannabidiol (2-(6-isopropenyl-3-methyl-6-cyclohexen-1-yl)-5-pentyl-1,3-benzenediol).

These compounds have one or more chiral centers and two or more stereoisomers as stated below: (1) (1) $\Delta^5$-cannabidiol has 2 chiral centers and 4 stereoisomers; (2) $\Delta^4$-cannabidiol has 3 chiral centers and 8 stereoisomers; (3) $\Delta^3$-cannabidiol has 2 chiral centers and 4 stereoisomers; (4) $\Delta^{3,7}$-cannabidiol has 2 chiral centers and 4 isomers; (5) $\Delta^2$-cannabidiol has 2 chiral centers and 4 stereoisomers; (6) $\Delta^1$-cannabidiol has 2 chiral centers and 4 stereoisomers; and (7) $\Delta^6$-cannabidiol has 1 chiral center and 2 stereoisomers. In a preferred embodiment, canabidiol is specifically $\Delta^2$-cannabidiol. Unless specifically stated, a reference to "cannabidiol," "CBD," or "cannabidiols" or to any of specific cannabidiol compounds (1)-(7) as referred to above includes all possible stereoisomers of all compounds included by the reference. In one embodiment, "$\Delta^2$-cannabidiol" can be a mixture of the $\Delta^2$-cannabidiol stereoisomers that are present in a plant, or an extract thereof, such as *Cannabis sativa, Cannabis indica*, or another plant of the *Cannabis* genus. In another embodiment, "$\Delta^2$-cannabidiol" is a mixture of the $\Delta^2$-cannabidiol stereoisomers that are present in a plant, or an extract thereof, such as *Cannabis sativa, Cannabis indica*, or another plant of the *Cannabis* genus, wherein said mixture of stereoisomers is at, or at about, the naturally occurring ratio of isomers. In another embodiment, the "$\Delta^2$-cannabidiol" is a single stereoisomer.

As used herein, the term "cannabinol" or "CBN" refers to 6,6,9-trimethyl-3-pentylbenzo[c]chromen-1-ol. CBN has no double bond isomers nor stereoisomers.

Keratins

Keratins are a family of about 30 proteins; they are the most abundant structural proteins in the cytoplasm of epithelial cells, in which they form a network of 10-12 nm wide intermediate filaments (IFs). Keratin proteins are encoded by a large family of conserved genes, numbering ~54 in the human genome that partition to the type I and II subgroupings of IF-encoding genes. There are 28 type I (K9-K28; K31-K40) and 26 type II (K1-K8; K71-K86) genes, each coding for one polypeptide chain. Type I proteins tend to be smaller (40-64 kDa) and more acidic (pI ~4.7-6.1) than the larger (52-70 kDa) and basic-neutral (pI ~5.4-8.4) type II proteins. The type I keratins include K9-K20 and the type II include K1-K8.

It is known that most combinations of type I and type II keratins can copolymerize in vitro; however, keratins are often co-expressed as specific pairs in vivo that are unique to that differentiation pathway. Keratin polymerization obligatorily begins with formation of coiled-coil heterodimers involving one type I and one type II protein. This contributes to the structure and strength of the cytoskeleton. The regulation of keratin genes, individually or as pairs, depends upon the type of epithelia, stage of cellular differentiation, and context (such as disease). During filament assembly, two keratin polypeptides, one of each type, first form a parallel heterodimer, in which the rod domains assemble into a coiled coil structure, which then undergoes further associations with other dimers to produce tetramers. The association of tetramers produces protofilaments and finally mature filaments. Without wishing to be bound by theory, the present inventors have discovered that, in certain contexts, modulation of gene transcription, protein synthesis, and/or activity, of one or more keratins in a cell or tissue, including one or more keratins that are not normally expressed in said cell or tissue can treat a disease or condition associated with intermediate filament dysfunction.

The keratinocytes in the mitotically active basal layer always express K5, K14, and K15. Upon commitment to differentiation, they down-regulate K5/K14/K15 transcription and activate expression of a new set of keratin pairs that vary among stratified tissues. For example, in cornified epithelia, such as those covering skin and gingivae, the differentiating keratinocytes express K1/K10. K6, K16 and K17 are induced, generally at the expense of other keratins, in the post-mitotic layers of interfollicular epidermis under conditions of environmental challenges (e.g., tissue injury, UV exposure, viral infection).

FIG. 1 is a diagram showing the different categories of epidermolysis bullosa (EB) and their association with specific dysfunctional proteins. FIG. 2 is a diagram of the structural layers and proteins of the skin showing the components and blistering levels associated with various types of EB. As described herein, the use of an appropriate cannabinoid or combination of cannabinoids, optionally in combination with other pharmaceutically active compounds, transcription, protein synthesis, and/or activity of various keratins can be modulated for therapeutic effect. In particular, as described herein the use of a cannabinoid or combination of cannabinoids, in particular CB1 antagonists or partial agonists, can be used to downregulate transcription of K14 and/or upregulate transcription of K15.

Cannabinoids

Cannabinoids are a group of chemicals known to activate cannabinoid receptors in cells throughout the human body, including the skin. Phytocannabinoids are the cannabinoids derived from cannabis plants. They can be isolated from plants or produced synthetically. Endocannabinoids are endogenous cannabinoids found in the human body.

Cannabinoids exert their effects by interacting with cannabinoid receptors present on the surface of cells. To date, two types of cannabinoid receptor have been identified, the CB1 receptor and the CB2 receptor. These two receptors share about 48% amino acid sequence identity, and are distributed in different tissues and also have different signaling mechanisms. They also differ in their sensitivity to agonists and antagonists. As described herein, certain cannabinoids are antagonists of the CB1 endocannabinoid receptors and may modulate the pathways leading to overexpression of mutated K14 and K5 and impact the production of K15, leading to (re-)establishment of the epidermal-dermal junction. They also modulate the hallmarks of intermediate filament associated diseases such as EBS for better treatment options such as: anti-inflammation, wound healing and skin regeneration, pain and itch reduction and antimicrobial properties.

Accordingly, in vitro and in vivo methods are described herein for screening for and identifying drug combinations that meet the following criteria: (1) cannabinoids or cannabinoid derivatives or analogs including classical cannabinoids, non-classical cannabinoids, aminoalkylindoles or eicosanoids that restore the structural integrity of the skin for patients that have a disease or condition associated with intermediate filament dysfunction (e.g., EBS) by up-regulating a compensatory keratin, and/or down-regulating the production of a mutated keratin; (2) cannabinoids or cannabinoid derivatives or analogs including classical cannabinoids, non-classical cannabinoids, aminoalkylindoles or eicosanoids that stimulate wound healing and skin or corneal regeneration, with priority given to efficacy as seem in Electric Cell-Substrate Impedance Sensing (ECIS) Wound Healing Assay (chronic model); (3) cannabinoids or cannabinoid derivatives or analogs including classical cannabinoids, non-classical cannabinoids, aminoalkylindoles or eicosanoids that provide an anti-inflammatory effect; or (4) cannabinoids or cannabinoid derivatives or analogs including classical cannabinoids, non-classical cannabinoids, aminoalkylindoles or eicosanoids that provide pain reduction. In a preferred embodiment of (1), the drug combination restores the structural integrity of the skin for patients that have a disease or condition such as EB (e.g., EBS) by up-regulating the compensatory keratin K15 and/or down-regulating the production of the mutated keratin K14.

Typically, the method accomplishes one or more of these four objectives: reducing inflammation; promoting wound healing and skin regeneration; reducing pain and itching; and reducing the occurrence of infection. Also, typically, the method accomplishes or the composition can provide one or more of the following therapeutic activities: (a) restoring anchoring function of skin or other epithelial structure; (b) downregulating one or both of K5 and K14; (c) upregulating K15; (d) rescuing TGF-β-induced downregulation of E-cadherin; and (e) increasing MCP-1 production. Individual cannabinoids or combinations of cannabinoids that meet one or more of these criteria are described below.

Typically, the therapeutically effective composition of cannabinoids is a mixture of cannabidiols and cannabinol selected from the group consisting of cannabidiols:cannabinol (1:0.1 µM), cannabidiols:cannabinol (0.1:1 µM), and cannabidiols:cannabinol (1:1 µM), or any molar ratio of cannabidiols:cannabinol from 0.1:10 to 10:0.1, preferably from 1:10 to 10:1, or from 1:5 to 5:1, 1:4 to 4:1, 1:3 to 3:1, 1:2 to 2:1, or 1:1. Preferably, the therapeutically effective quantity of a cannabinoid is cannabidiols:cannabinol (1:0.1 µM). A particularly preferred cannabidiol is $\Delta^2$-cannabidiol as described herein; this is the naturally-occurring form of cannabidiol, but other positional isomers differing in the positions of the double bond in the non-aromatic six-membered ring can alternatively be used.

Alternatively, other cannabinoids can be used in methods according to the present invention. Such cannabinoids can be screened using the methods described herein to identify preferred cannabinoids and combinations thereof. These cannabinoids include, but are not limited to, $\Delta^9$-tetrahydrocannabinol ($\Delta^9$-THC), the synthetic cannabinoid HU-210 (6aR,10aR)-9-(hydroxymethyl)-6,6-dimethyl-3-(2-methyl-octan-2-yl)-6H,6aH,7H,10H,10aH-benzo[c]isochromen-1-ol), cannabidivarin (CBDV), cannabichromene (CBC), cannabichromevarin (CBCV), cannabigerol (CBG), cannabigerovarin (CBGV), cannabielsoin (CBE), cannabicyclol (CBL), cannabivarin (CBV), and cannabitriol (CBT). Still other cannabinoids can be used, including tetrahydrocannibivarin (THCV) and cannabigerol monomethyl ether (CBGM). Additional cannabinoids occur and can be used, including cannabichromenic acid (CBCA), $\Delta^1$-tetrahydrocannabinolic acid (THCA); and cannabidiolic acid (CBDA); these additional cannabinoids are characterized by the presence of a carboxylic acid group in their structure. Still other cannabinoids include nabilone, rimonabant, JWH-018 (naphthalen-1-yl-(1-pentylindol-3-yl)methanone), JWH-073 naphthalen-1-yl-(1-butylindol-3-yl)methanone, CP-55940 (2-[(1R,2R,5R)-5-hydroxy-2-(3-hydroxypropyl)cyclohexyl]-5-(2-methyloctan-2-yl)phenol), dimethylheptylpyran, HU-331 (3-hydroxy-2-[(1R)-6-isopropenyl-3-methyl-cyclohex-2-en-1-yl]-5-pentyl-1,4-benzoquinone), SR144528 (5-(4-chloro-3-methylphenyl)-1-[(4-methylphenyl)methyl]-N-[(1S,2S,4R)-1,3,3-trimethylbicyclo[2.2.1]heptan-2-yl]-1H-pyrazole-3-carboxamide), WIN 55, 212-2 ((11R)-2-methyl-11-[(morpholin-4-yl)methyl]-3-(naphthalene-1-carbonyl)-9-oxa-1-azatricyclo[6.3.1.0$^{4,12}$]dodeca-2,4(12),5,7-tetraene), JWH-133 ((6aR,10aR)-3-(1,1-dimethylbutyl)-6a,7,10,10a-tetrahydro-6,6,9-trimethyl-6H-dibenzo[b,d]pyran), levonatradol, and AM-2201 (1-[(5-fluoropentyl)-1H-indol-3-yl]-(naphthalen-1-yl)methanone). Other cannabinoids include $\Delta^8$-tetrahydrocannabinol ($\Delta^8$-THC), 11-hydroxy-$\Delta^9$-tetrahydrocannabinol, $\Delta^{11}$-tetrahydrocannabinol, and 11-hydroxy-tetracannabinol. In another alternative, analogs or derivatives of these cannabinoids can be used as described further below.

Synthetic cannabinoids are also disclosed in U.S. Pat. No. 9,394,267 to Attala et al.; U.S. Pat. No. 9,376,367 to Herkenroth et al.; U.S. Pat. No. 9,284,303 to Gijsen et al.; U.S. Pat. No. 9,173,867 to Travis; U.S. Pat. No. 9,133,128 to Fulp et al.; U.S. Pat. No. 8,778,950 to Jones et al.; U.S. Pat. No. 7,700,634 to Adam-Worrall et al.; U.S. Pat. No. 7,504,522 to Davidson et al.; U.S. Pat. No. 7,294,645 to Barth et al.; U.S. Pat. No. 7,109,216 to Kruse et al.; U.S. Pat. No. 6,825,209 to Thomas et al.; and U.S. Pat. No. 6,284,788 to Mittendorf et al.

U.S. Pat. No. 9,394,267 to Attala et al. discloses synthetic cannabinoids of Formula (C-I):

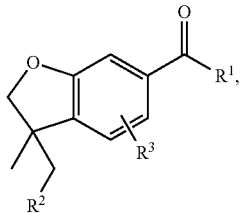

(C-I)

wherein:
(1) $R^1$ is selected from the group consisting of $NH_2$, $NHR^4$, and $NR^4R^5$, any carbon atom of which may be optionally substituted;
(2) $R^2$ is selected from the group consisting of hydrogen, aryl, alkyl, cycloalkyl, aralkyl, alkenyl, and alkynyl, any carbon atom of which may be optionally substituted;
(3) $R^3$ is selected from the group consisting of hydrogen, halogen, alkyl, cycloalkyl, heterocycloalkyl, aryl, and heteroaryl, any carbon atom of which may be optionally substituted; and
(4) $R^4$ and $R^5$ vary independently and are selected from the group consisting of aryl, alkyl, cycloalkyl, aralkyl, alkenyl, and alkynyl, any carbon atom of which may be optionally substituted.

U.S. Pat. No. 9,394,267 to Attala et al. also discloses synthetic cannabinoids of Formula (C-II):

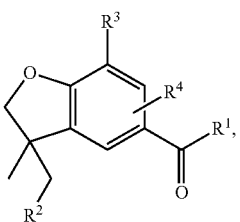

(C-II)

wherein:
(1) $R^1$ is selected from the group consisting of $NH_2$, $NHR^5$, and $NR^5R^6$, any carbon atom of which may be optionally substituted;
(2) $R^2$ is selected from the group consisting of hydrogen, aryl, alkyl, cycloalkyl, aralkyl, alkenyl, and alkynyl, any carbon atom of which may be optionally substituted; (3) $R^3$ and $R^4$ are independently selected from the group consisting of hydrogen, halogen, alkyl, cycloalkyl, heterocycloalkyl, aryl, and heteroaryl;
(4) $R^5$ and $R^6$ are independently selected from the group consisting of aryl, alkyl, cycloalkyl, aralkyl, alkenyl, and alkynyl; and
(5) when $R^2$ is hydrogen, $R^3$ is not t-butyl, bromo, methoxy, or a moiety of Subformula (C-II(a)):

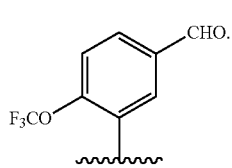

(C-II(a))

U.S. Pat. No. 9,376,367 to Herkenroth et al. discloses cannabinoid carboxylic acids and salts of cannabinoid carboxylic acids.

U.S. Pat. No. 9,284,303 to Gijsen et al. discloses benzimidazole cannabinoid agonists bearing a substituted heterocyclic group.

U.S. Pat. No. 9,173,867 to Travis discloses cannabinoid derivatives of Formula (C-III):

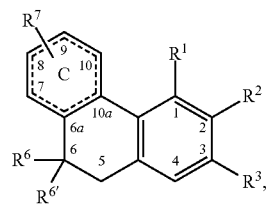

(C-III)

wherein:
(1) $R^1$ and $R^2$ are each hydrogen;
(2) $R^3$ is $(W)_m-Y-(Z)_n$, wherein: (a) W is a $C_5$-$C_{12}$ straight or branched-chain alkyl; (b) Y is a valence bond; (c) Z is a $C_5$-$C_{12}$ alkyl; and (d) m and n are different, and each is either 0 or 1;
(3) $R^6$ and $R^{6'}$ are each methyl;
(4) $R^7$ is methyl;
(5) Q is O; and
(6) the dashed line of Ring C represents a double bond at Δ8-9.

U.S. Pat. No. 9,133,128 to Fulp et al. discloses N-piperidine-containing cannabinoid analogs of Formula (C-IV):

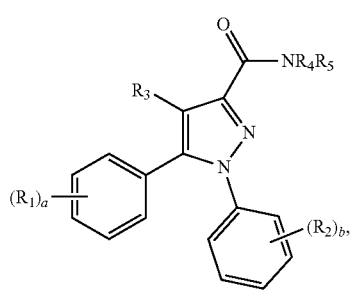

(C-IV)

wherein:
(1) $R_1$ and $R_2$ is a substituent independently selected from the group consisting of Cl, F, Br, OH, optionally substituted $C_1$-$C_{10}$ alkyl, optionally substituted $C_1$-$C_{10}$ alkoxy, optionally substituted $C_2$-$C_4$ alkenyl, optionally substituted $C_2$-$C_4$ alkynyl, $NR^{10}R^{11}$, $NHCOR^{10}$, $NHCO_2R^{10}$, $CH_2OR^{10}$, $CONR^{10}R^{11}$, $CO_2R^{10}$, CN, $CF_3$, $NO_2$, $N_3$, $C_1$-$C_3$ alkylthio, $R^{10}SO$, $R^{10}SO_2$, $CF_3S$, and $CF_3SO_2$;
(2) $R_3$ is H or $C_1$-$C_3$ alkyl;
(3) $R_4$ and $R_5$ taken together form a piperidine ring with the N to which they are attached, which is substituted at the 4 position with at least one substituent selected from the group consisting of $NR^{10}R^{11}$, $NR^{10}COR^{11}$, $NR^{10}SO_2R^{11}$, $NHCONR^{10}R^{11}$, $NR^{10}COOR^{11}$; and $CONR^{10}R^{11}$;
(4) $R^{10}$ and $R^{11}$ are independently selected from H and $C_1$-$C_{10}$ alkyl; and
(5) a and b are each independently integers from 0 to 5.

U.S. Pat. No. 8,778,950 to Jones et al. discloses pyrazine derivatives including (1aS,5aS)-2-pyrazin-2-yl-1a,2,5,5a-tetrahydro-1H-2,3-diaza-cyclopropa[a]pentalene-4-carboxylic acid ((S)-1-hydroxymethyl-2,2-dimethyl-propyl)-amide and (1aS,5aS)-2-(4-oxy-pyrazin-2-yl)-1a,2,5,5a-tetrahydro-1H-2,3-diaza-cyclopropa[a]pentalene-4-carboxylic acid ((S)-1-hydroxymethyl-2,2-dimethyl-propyl)-amide.

U.S. Pat. No. 7,700,634 to Adam-Worrall et al. discloses indolyl-3-yl cannabinoid analogs including 7-chloro-3-(5-{[N-ethyl-N-(2-methoxyethyl)amino]methyl}-[1,2,4]-thiadiazol-3-yl)-1-(tetrahydropyran-4-yl)methyl-1H-indole; 7-chloro-3-{5-[(pyrrolidin-1-yl)methyl]-[1,2,4]-thiadiazol-3-yl}-1-(tetrahydropyran-4-yl)methyl-1H-indole; 7-chloro-3-(5-{[N-ethyl-N-(2-hydroxyethyl)amino]methyl}-[1,2,4]-thiadiazol-3-yl)-1-(tetrahydropyran-4-yl)methyl-1H-indole; 7-chloro-3-(4-{[N-(2-hydroxyethyl)-N-isopropylamino]methyl}-[1,3]-thiazol-2-yl)-1-(tetrahydropyran-4-yl)methyl-1H-indole; 7-chloro-3-(4-{[N-ethyl-N-(2-hydroxyethyl)amino]methyl}-[1,3]-thiazol-2-yl)-1-(tetrahydropyran-4-yl)methyl-1H-indole; 7-chloro-3-(4-{[N-(2-methoxyethyl)-N-methylamino]methyl}-[1,3]-thiazol-2-yl)-1-(tetrahydropyran-4-yl)methyl-1H-indole; and 7-chloro-3-{5-[(2,2-dimethyl-pyrrolidin-1-yl)methyl]-[1,2,4]oxadiazol-3-yl}-1-(tetrahydropyran-4-yl)methyl-1H-indole.

U.S. Pat. No. 7,504,522 to Davidson et al. discloses azetidinecarboxamine cannabinoid derivatives of Formula (C-V):

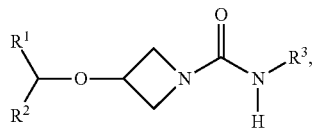

wherein:
(1) $R^1$ and $R^2$ are each independently selected from aryl; and
(2) $R^3$ is hydrogen or alkyl;
wherein at least one of $R^1$ and $R^2$ has a non-hydrogen substituent in the ortho position or positions relative to the point of attachment to the [—CH—O—] group.

U.S. Pat. No. 7,294,645 to Barth et al. discloses derivatives of N'-(1,5-diphenyl-1H-pyrazol-yl)sulfonamide as cannabinoid analogs of Formula (C-VI):

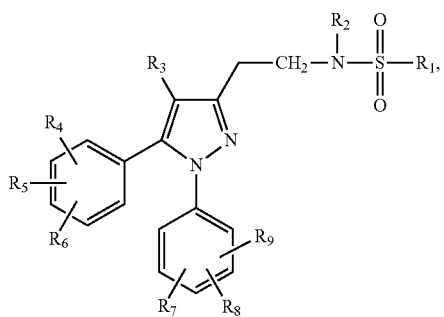

wherein:
(1) $R_1$ represents a $(C_1-C_6)$alkyl; a $(C_3-C_7)$cycloalkyl which is unsubstituted or substituted once or several times with a $(C_1-C_6)$alkyl group; a $(C_3-C_7)$cycloalkyl-methyl which is unsubstituted or substituted once or several times on the carbocycle with a $(C_1-C_3)$alkyl; a phenyl which is unsubstituted or mono-, di- or trisubstituted with a substituent independently chosen from a halogen atom, a $(C_1-C_4)$alkyl, a $(C_1-C_6)$alkoxy, a cyano, a trifluoromethyl radical, a trifluoromethoxy radical, an $S(O)_n$Alk group, a $(C_1-C_3)$alkylcarbonyl group, a phenyl; a benzyl which is unsubstituted or mono- or disubstituted with a substituent independently chosen from a halogen atom, a $(C_1-C_3)$alkyl, a $(C_1-C_3)$alkoxy; a trifluoromethyl radical; a thienyl which is unsubstituted or substituted with a halogen atom or with an isoxazolyl;
(2) $R_2$ represents a hydrogen atom or a $(C_1-C_3)$alkyl;
(3) $R_3$ represents a hydrogen atom or a $(C_1-C_5)$alkyl;
(4) $R_4$, $R_5$, $R_6$, $R_7$, $R_8$ and $R_9$ each independently represent a hydrogen atom, a halogen atom, a $(C_1-C_7)$alkyl, a $(C_1-C_5)$alkoxy, a trifluoromethyl radical or an $S(O)_n$Alk group;
(5) n represents 0, 1 or 2; and
(6) Alk represents a $(C_1-C_4)$alkyl.

U.S. Pat. No. 7,109,216 to Kruse et al. discloses cannabinoid analogs that are 1H-imidazole derivatives of Formula (C-VII):

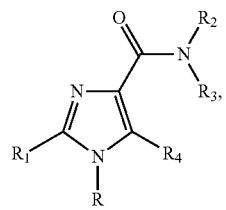

wherein:
(1) R represents phenyl, thienyl, 2-pyridinyl, 3-pyridinyl, 4-pyridinyl, pyrimidinyl, pyrazinyl, pyridazinyl or triazinyl, which groups may be substituted with 1, 2, 3 or 4 substituents Y, which can be the same or different, from the group $C_1-C_3$ alkyl or alkoxy, hydroxy, halogen, trifluoromethyl, trifluoromethylthio, trifluoromethoxy, nitro, amino, mono- or dialkyl $(C_1-C_2)$-amino, mono- or dialkyl $(C_1-C_2)$-amido, $(C_1-C_3)$-alkoxycarbonyl, carboxyl, cyano, carbamoyl and acetyl, or R represents naphthyl, with the proviso that when R is 4-pyridinyl, $R_4$ represents a halogen atom or a cyano, carbamoyl, formyl, acetyl, trifluoroacetyl, fluoroacetyl, propionyl, sulfamoyl, methanesulfonyl, methylsulfanyl or branched or unbranched $C_1-C_4$ alkyl group, which $C_1-C_4$ alkyl group may be substituted with 1 to 3 fluoro atoms or with a bromo, chloro, iodo, cyano or hydroxy group;
(2) $R_1$ represents phenyl or pyridinyl, which groups may be substituted with 1 to 4 substituents Y, which can be the same or different, wherein Y has the above mentioned meaning, or $R_1$ represents pyrimidinyl, pyrazinyl, pyridazinyl or triazinyl, which groups may be substituted with 1 or 2 substituents Y, which can be the same or different or $R_1$ represents a five-membered aromatic heterocyclic ring having one or two heteroatoms from the group (N, O, S), which heteroatoms can be the same or different, which five-membered aromatic heterocyclic ring may be substituted with 1 2 substituents Y, which can be the same or different or $R_1$ represents naphthyl;

(3) $R_2$ represents H, branched or unbranched $C_1$-$C_5$ alkyl, $C_3$-$C_8$ cycloalkyl, $C_3$-$C_8$ alkenyl, $C_5$-$C_8$ cycloalkenyl which groups may contain a sulfur, oxygen or nitrogen atom;

(4) $R_3$ represents branched or unbranched $C_2$-$C_5$ alkyl, $C_1$-$C_5$ alkoxy, $C_5$-$C_8$ cycloalkyloxy, $C_5$-$C_8$ cycloalkyl, $C_5$-$C_8$ bicycloalkyl, $C_6$-$C_{10}$ tricycloalkyl, $C_3$-$C_8$ alkenyl, $C_5$-$C_8$ cycloalkenyl, which groups may optionally contain one or more heteroatoms from the group (O, N, S) and which groups may be substituted with a hydroxy group or 1 or 2 $C_1$-$C_3$ alkyl groups or 1 to 3 fluoro atoms, or $R_3$ represents a benzyl or phenethyl group which aromatic rings may be substituted with 1 to 5 substituents Z, which can be the same or different, from the group $C_1$-$C_3$ alkyl or alkoxy, hydroxy, halogen, trifluoromethyl, trifluoromethylthio, trifluoromethoxy, nitro, amino, mono- or dialkyl ($C_1$-$C_2$)-amino, mono- or dialkyl ($C_1$-$C_2$)-amido, ($C_1$-$C_3$)-alkylsulfonyl, dimethyl-sulfamido, $C_1$-$C_3$-alkoxycarbonyl, carboxyl, trifluoromethylsulfonyl, cyano, carbamoyl, sulfamoyl and acetyl, or $R_3$ represents a phenyl or pyridinyl group, which groups are substituted with 1 to 4 substituents Z, wherein Z has the meaning as indicated above, or $R_3$ represents a pyridinyl group, or $R_3$ represents a phenyl group, with the proviso that $R_4$ represents a halogen atom or a cyano, carbamoyl, formyl, acetyl, trifluoroacetyl, fluoroacetyl, propionyl, sulfamoyl, methanesulfonyl, methylsulfanyl or $C_1$-$C_4$ alkyl group, which $C_1$-$C_4$ alkyl group may be substituted with 1 to 3 fluoro atoms or with a bromo, chloro, iodo, cyano or hydroxy group, or $R_3$ represents a group $NR_5R_6$, with the proviso that $R_2$ represents a hydrogen atom or a methyl group, wherein $R_5$ and $R_6$ are the same or different and represent branched or unbranched $C_1$-$C_4$ alkyl, or $R_5$ and $R_6$—together with the nitrogen atom to which they are bonded—form a saturated or unsaturated, monocyclic or bicyclic heterocyclic group having 4 to 10 ring atoms which heterocyclic group contains one or two heteroatoms from the group (N, O, S), which heteroatoms can be the same or different, which heterocyclic group may be substituted with a $C_1$-$C_3$ alkyl group or a hydroxy group, or $R_2$ and $R_3$—together with the nitrogen atom to which they are bonded—form a saturated or unsaturated heterocyclic group having 4 to 10 ring atoms which heterocyclic group contains one or two heteroatoms from the group (N, O, S), which heteroatoms can be the same or different, which heterocyclic group may be substituted with a $C_1$-$C_3$ alkyl group or a hydroxy group; and (5) $R_4$ represents a hydrogen or halogen atom or a cyano, carbamoyl, formyl, acetyl, trifluoroacetyl, fluoroacetyl, propionyl, sulfamoyl, methanesulfonyl, methylsulfanyl or branched or unbranched $C_1$-$C_4$ alkyl group, which $C_1$-$C_4$ alkyl group may be substituted with 1 to 3 fluoro atoms or with a bromo, chloro, iodo, cyano or a hydroxy group.

U.S. Pat. No. 6,825,209 to Thomas et al. discloses analogs of cannabinoids that are amide analogs and include compounds of Formula (C-VIII):

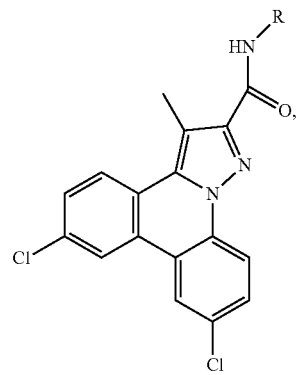

(C-VIII)

wherein R is a linear or branched hydrocarbon group of 7 to 12 carbons or N-piperidinyl.

U.S. Pat. No. 6,284,788 to Mittendorf et al. discloses a number of cannabinoid derivatives and analogs including classical cannabinoids, non-classical cannabinoids, aminoalkylindoles and eicosanoids.

In another alternative, the cannabinoid can be an endocannabinoid or a derivative or analog thereof. Endocannabinoids include but are not limited to anandamide, 2-arachidonoylglycerol, 2-arachidonyl glyceryl ether, N-arachidonoyl dopamine, and virodhamine. A number of analogs of endocannabinoids are known, including 7,10,13,16-docosatetraenoylethanolamide, oleamide, stearoylethanolamide, and homo-γ-linolenoylethanolamine, are also known.

In general, cannabinoids suitable for use in methods and compositions according to the present invention are either selective for the CB2 cannabinoid receptor or are non-selective for the two cannabinoid receptors, binding to either the CB1 cannabinoid receptor or the CB2 cannabinoid receptor. Preferably, cannabinoids suitable for use in methods and compositions according to the present invention are selective for the CB2 cannabinoid receptor. In some cases, the cannabinoids, or one of the cannabinoids in a mixture of cannabinoids is an antagonist (e.g., selective or non-selective antagonist) of CB2.

In some cases, the cannabinoids, or one of the cannabinoids in a mixture of cannabinoids is an antagonist (e.g., selective or non-selective antagonist) of CB2. In some cases, the cannabinoids, or one of the cannabinoids in a mixture of cannabinoids is an inverse agonist (e.g., selective or non-selective inverse agonist) of CB2. In some cases, the cannabinoids, or one of the cannabinoids in a mixture of cannabinoids is a neutral antagonist (e.g., selective or non-selective neutral antagonist) of CB2. In some cases, the cannabinoids, or one of the cannabinoids in a mixture of cannabinoids is a partial agonist (e.g., selective or non-selective neutral agonist) of CB2.

In some embodiments, cannabinoids suitable for use in methods and compositions according to the present invention are selective for the CB1 cannabinoid receptor. In some cases, the cannabinoids, or one of the cannabinoids in a mixture of cannabinoids is an antagonist (e.g., selective or non-selective antagonist) of CB1. In some cases, the cannabinoids, or one of the cannabinoids in a mixture of cannabinoids is an inverse agonist (e.g., selective or non-selective inverse agonist) of CB1. In some cases, the cannabinoids, or one of the cannabinoids in a mixture of cannabinoids is a neutral antagonist (e.g., selective or non-selective neutral antagonist) of CB1. In some cases, the cannabinoids, or one of the cannabinoids in a mixture of cannabinoids is a partial agonist (e.g., selective or non-selective neutral agonist) of CB1.

Typically, the cannabinoid or mixture of cannabinoids is administered in a pharmaceutical composition which optionally includes one or more terpenoids. The pharmaceutical composition includes: (1) a therapeutically effective quantity of the cannabinoid or the mixture of cannabinoids; and (2) at least one pharmaceutically acceptable carrier for topical administration of the composition. Suitable pharmaceutically acceptable carriers include LABRASOL® (caprylocaproyl polyoxyl-8 glycerides), poloxamer 407, lecithin, and isopropyl palmitate. A preferred pharmaceutical composition includes LABRASOL®, poloxamer 407, lecithin, and isopropyl palmitate as pharmaceutically acceptable carriers. Further alternatives for pharmaceutically acceptable carriers or combinations of pharmaceutically acceptable carriers are described herein.

Terpenoids

Terpenoids interact with and potentiate the activity of cannabinoids, although by themselves, they do not have cannabinoid activity and do not bind to cannabinoid receptors. In some embodiments, the method can further comprise simultaneous or sequential topical administration of a therapeutically effective quantity of a terpenoid in the same or a different pharmaceutical composition.

When the cannabinoid to be administered is CBD (cannabidiols), CBG (cannabigerol), or CBN (cannabinol), suitable terpenoids include but are not limited to borneol, carvophyllene, 1,8-cineol, p-cymene, fenchone, α-humulene, kaempferol, limonene, linoleic acid, α-linolenic acid, luteolin, β-myrcene, oleic acid, orientin, α-pinene, phytol, quercetin, selinene, sitosterol, terpinenol-4, N-trans-caffeoyltyramine, N-trans-coumaroyltyramine, N-trans-feruloyltyramine, and vitexin. This combination of cannabinoids and terpenoids is particularly effective in promoting anti-inflammatory activity.

When the cannabinoid to be administered is CBC (cannabichromene), CBD, CBG, or CBN, suitable terpenoids include but are not limited to caryophyllene oxide, camphene, 1,8-cineole, p-cymene, kaempferol, limonene, linalool, nerolidol, α-pinene, β-pinene, phytol, β-sitosterol, and N-trans-caffeoyltyramine. This combination of cannabinoids and terpenoids is particularly effective in promoting anti-microbial activity.

When the cannabinoid to be administered is CBD or $\Delta^8$-THC ($\Delta^8$-tetrahydrocannabinol), suitable terpenoids include but are not limited to apigenin, caryophyllene, linoleic acid, luteolin, quercetin, and phytol. This combination of cannabinoids and terpenoids is particularly effective in promoting anti-itch activity.

When the cannabinoid is CBC, CBD, CBG, CBN, or $\Delta^9$-THC ($\Delta^9$-tetrahydrocannabinol), suitable terpenoids include but are not limited to borneol, caryophyllene, p-cymene, linalool, β-sitosterol, and vitexin. This combination of cannabinoids and terpenoids is particularly effective in promoting anti-pain activity.

When the cannabinoid is CBD, CBG, CBN, $\Delta^8$-THC, or $\Delta^9$-THC, suitable terpenoids include but are not limited to borneol, linalool, and kaempferol. This combination of cannabinoids and terpenoids is particularly effective in promoting wound healing activity.

Pharmaceutical Compositions

Pharmaceutical compositions according to the present invention can include one or more excipients. Such excipients that are suitable for use in topical compositions intended for application to the skin include, but are not limited to: preservatives; thickening agents; buffers; liquid carriers; isotonic agents; wetting, solubilizing, and emulsifying agents; acidifying agents; antioxidants; alkalinizing agents; carrying agents; chelating agents; complexing agents; solvents; suspending or viscosity-increasing agents; oils; penetration enhancers; polymers; stiffening agents; proteins; carbohydrates; and bulking agents.

As is generally known in the art of pharmaceutical formulation, a particular excipient can fulfill one or more of these functions in a particular pharmaceutical composition, depending on the concentration of the excipient, the other excipients in the composition, the physical form of the composition, the concentration of active agent in the composition, the intended route of administration of the composition, and other factors. The recitation of a particular excipient in a category below is not intended to exclude the possible use of the excipient in another category or categories.

The liquid carrier can be, but is not limited to, a liquid carrier selected from the group consisting of saline, phosphate buffered saline, glycerol, and ethanol.

A thickening agent can be, but is not limited to, a thickening agent selected from the group consisting of glycerol and propylene glycol.

An isotonic agent can be, but is not limited to: a polyalcohol selected from the group consisting of mannitol and sorbitol; sodium chloride; and potassium chloride.

The wetting, solubilizing, or emulsifying agent is generally a surfactant. Typically, the surfactant is selected from the group consisting of benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol, acacia, cholesterol, diethanolamine, glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, triethanolamine, emulsifying wax, cetomacrogol, and cetyl alcohol.

The pharmaceutical composition for topical application can include an emollient. As used herein, the term "emollient" refers to a hydrophobic agent that softens, smoothens and improves lipid content of the skin or other mucous membranes. Examples of suitable emollients for use include isostearic acid derivatives, isopropyl palmitate, lanolin oil, diisopropyl dimerate, diisopropyl adipate, dimethyl isosorbide, maleated soybean oil, octyl palmitat, isopropyl isostearate, cetyl alcohol, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristyl myristate, triisocetyl citrate, octyl dodecanol, octyl hydroxystearate, grape seed oil, one or more ceramides, cyclomethicone, and mixtures thereof. Other examples of other suitable emollients can also be found in the Cosmetic Bench Reference, pp. 1.19-1.22 (1996). One of skill in the art will appreciate that other emollients are useful in the present invention.

The preservative can be selected from the group consisting of benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, diazolidinyl urea, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol.

The composition can include a buffer selected from the group consisting of acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, sodium bicarbonate, Tris (Tris(hydroxymethyl)aminomethane), MOPS (3-(N-morpholino)propanesulfonic acid), HEPES (N-(2-hydroxyethyl)piperazine-N'-(2-ethanesulfonic acid), ACES (2-[(2-amino-2-oxoethyl)amino]ethanesulfonic acid), ADA (N-(2-acetamido)2-iminodiacetic acid), AMPSO (3-[(1,1-dimethyl-2-hydroxyethylamino]-2-propanesulfonic acid), BES (N,N-bis(2-hydroxyethyl)-2-aminoethanesulfonic acid, Bicine (N,N-bis(2-hydroxyethylglycine), Bis-Tris (bis-(2-hydroxyethyl)imino-tris(hydroxymethyl)methane, CAPS (3-(cyclohexylamino)-1-propanesulfonic acid), CAPSO (3-(cyclohexylamino)-2-hydroxy-1-propanesulfonic acid), CHES (2-(N-cyclohexylamino)ethanesulfonic acid), DIPSO (3-[N,N-bis(2-hydroxyethylamino]-2-hydroxy-propanesulfonic acid), HEPPS (N-(2-hydroxyethylpiperazine)-N'-(3-propanesulfonic acid), HEPPSO (N-(2-hydroxyethyl) piperazine-N'-(2-hydroxypropanesulfonic acid), MES (2-(N-morpholino)ethanesulfonic acid), triethanolamine, imidazole, glycine, ethanolamine, phosphate, MOPSO (3-(N-morpholino)-2-hydroxypropanesulfonic acid), PIPES (piperazine-N,N'-bis(2-ethanesulfonic acid), POPSO (piperazine-N,N'-bis(2-hydroxypropaneulfonic acid), TAPS (N-tris[hydroxymethyl)methyl-3-aminopropanesulfonic acid), TAPSO (3-[N-tris(hydroxymethyl)methylamino]-2-hydroxy-propanesulfonic acid), TES (N-tris(hydroxymethyl)methyl-2-aminoethanesulfonic acid), tricine (N-tris(hydroxymethyl)methylglycine), 2-amino-2-methyl-1,3-propanediol, and 2-amino-2-methyl-1-propanol.

Typically, the acidifying agent is selected from the group consisting of acetic acid, citric acid, fumaric acid, hydrochloric acid, diluted hydrochloric acid, malic acid, nitric acid, phosphoric acid, diluted phosphoric acid, sulfuric acid, and tartaric acid.

Typically, the antioxidant is selected from the group consisting of ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, sodium thiosulfate, sulfur dioxide, and tocopherol.

Typically, the alkalinizing agent is selected from the group consisting of strong ammonia solution, ammonium carbonate, diethanolamine, diisopropanolamine, potassium hydroxide, sodium bicarbonate, sodium borate, sodium carbonate, sodium hydroxide, and trolamine.

The carrying agent can be selected from the group consisting of corn oil, mineral oil, peanut oil, sesame oil, bacteriostatic sodium chloride and bacteriostatic water.

The chelating agent can be selected from the group consisting of edetate disodium, ethylenediaminetetraacetic acid, citric acid, and salicylates.

The complexing agent can be selected from the group consisting of ethylenediaminetetraacetic acid, salts of ethylenediaminetetraacetic acid, gentisic acid ethanolamide, and oxyquinoline sulfate.

The solvent can be selected from the group consisting of acetone, ethanol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl isobutyl ketone, mineral oil, oleic acid, peanut oil, polyethylene glycol, propylene carbonate, propylene glycol, sesame oil, water, sterile water, and purified water.

Typically, the suspending and/or viscosity-increasing agent is selected from the group consisting of acacia, agar, alginic acid, aluminum monostearate, bentonite, purified bentonite, magma bentonite, carbomers, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, Veegum, and xanthan gum.

Typically, the oil is selected from the group consisting of arachis oil, mineral oil, olive oil, sesame oil, cottonseed oil, safflower oil, corn oil, and soybean oil.

Typically, the penetration enhancer is selected from the group consisting of monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones, and ureas.

Typically, the polymer is selected from the group consisting of cellulose acetate, alkyl celluloses, hydroxyalkyl-celluloses, acrylic polymers and copolymers, polyesters, polycarbonates, and polyanhydrides.

Typically, the stiffening agent is selected from the group consisting of hydrogenated castor oil, cetostearyl alcohol, cetyl alcohol, cetyl esters wax, hard fat, paraffin, polyethylene excipient, stearyl alcohol, emulsifying wax, white wax, and yellow wax.

Typically, the protein is selected from the group consisting of bovine serum albumin, human serum albumin (HSA), recombinant human albumin (rHA), gelatin, and casein.

Typically, the carbohydrate is selected from the group consisting of fructose, maltose, galactose, glucose, D-mannose, sorbose, lactose, sucrose, trehalose, cellobiose, raffinose, melezitose, maltodextrins, dextrans, starches, mannitol, maltitol, lactitol, xylitol, sorbitol, and myoinositol.

Typically, the bulking agent is selected from the group consisting of polypeptides and amino acids.

The composition can further comprise a a topical soothing agent for the skin, a topical anti-inflammatory agent, a topical anti-bacterial agent, a topical anti-fungal agent, a topical steroid, and a topical antioxidant.

Topical soothing agents for the skin typically include chamomile and aloe; other topical soothing agents are known in the art and can be used.

Topical anti-inflammatory agents typically include diclofenac, ketoprofen, ibuprofen, piroxicam, and indomethacin; other topical anti-inflammatory agents are known in the art and can be used.

Topical anti-bacterial agents typically include bacitracin, polymyxin B, erythromycin, sodium sulfacetamide, silver sulfadiazine, retapamulin, mupirocin, neomycin, and pramoxine; other topical anti-bacterial agents are known in the art and can be used.

Topical anti-fungal agents typically include benzoic acid, salicylic acid, undecylenic acid, ketoconazole, nystatin, naftifine, tolnaftate, miconazole, econazole, ciclopirox, oxiconazole, sertaconazole, efinaconazole, terbinafine, tavaborole, clotrimazole, sulconazole, and butenafine; other topical anti-fungal agents are known in the art and can be used.

Topical steroids typically include hydrocortisone, triamcinolone, fluocinolone, prednicarbate, desonide, betamethasone, halcinonide, diflorasone, fluocinolone, clobetasol, desoxymetasone, mometasone, clocortolone, fluticasone, fluocinonide, flurandrenolide, alclometasone, and halobetasol; other topical steroids are known in the art and can be used.

Topical antioxidants typically include vitamin C, vitamin E, and L-selenomethionine; other topical antioxidants are known in the art and can be used.

Other active agents can be included.

In an alternative, a number of these additional agents, such as a topical anti-inflammatory agent, a topical anti-bacterial agent, a topical anti-fungal agent, a topical steroid, and a topical anti-oxidant, can be administered separately, such as in one or more additional pharmaceutical compositions including one or more excipients as described above.

In some alternatives, including the use of prodrugs as described above, therapeutically active compounds used in methods and compositions according to the present invention, including but not limited to cannabinoids and terpenoids, are formed by covalently cross-linking one or more conjugation partners to the therapeutically active compound. Suitable reagents for cross-linking many combinations of functional groups are known in the art.

For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150.

The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146.

Additionally, electrophilic reagents are known that will react with carboxylate side chains such as those of aspartate and glutamate, such as diazoalkanes and diazoacetyl compounds, carbonyldimidazole, and carbodiimides. These are described in G. T. Hermanson, "Bioconjugate Techniques" (Academic Press, San Diego, 1996), pp. 152-154. Furthermore, electrophilic reagents are known that will react with hydroxyl groups such as those in the side chains of serine and threonine, including reactive haloalkane derivatives. These are described in G. T. Hermanson, "Bioconjugate Techniques" (Academic Press, San Diego, 1996), pp. 154-158. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996).

The amount of a given therapeutically active agent, such as, but not limited to, a cannabinoid or terpenoid as described above, that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject.

It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. Optimal dosages for a given set of conditions can be ascertained by those skilled in the art using conventional dosage-determination tests in view of the experimental data for an agent.

The compositions of the invention or compositions employed according to the present invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic.

In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

U.S. Pat. No. 6,573,292 to Nardella, U.S. Pat. No. 6,921,722 to Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

REFERENCES

The following publications are incorporated herein by this reference. These publications are referred to herein by the numbers provided below. The inclusion of any publication in this list of publications is not to be taken as an admission that any publication referred to herein is prior art.

(1) Nada Radoja et al., Thyroid Hormones and Gamma Interferon Specifically Increase K15 Keratin Gene Transcription, Mol Cell Biol. April 2004; 24(8): 3168-3179.

(2) Ahmad Waseem et al., Keratin 15 Expression in Stratified Epithelia: Downregulation in Activated Keratinocytes, J Invest Dermatol. March 1999; 112, 362-369.

(3) Amrita Bose et al., Two Mechanisms Regulate Keratin K15 Expression In Keratinocytes: Role of PKC/AP-1 and FOXM1 Mediated Signalling, PLoS One 2012; 7(6): e38599.

(4) Hatzfeld, M & Franke, WW: Pair formation and promiscuity of cytokeratins: formation in vitro of heterotypic complexes and intermediate-sized filaments by homologous and heterologous recombinations of purified polypeptides. J Cell Biol, 1985 101, 1826-1841.

(5) Gardner B et al, Autocrine and paracrine regulation of lymphocyte CB2 receptor expression by TGF-beta, Biochem Biophys Res Commun. 2002 Jan. 11; 290(1): 91-6.

(6) Martin Wagner et al, Imbalance of intermediate filament component keratin 14 contributes to increased stress signalling in epidermolysis bullosa simplex, Exp Dermatol. 2013 April; 22(4):292-4.

(7) Daniel Rueda et al, The CB1 Cannabinoid Receptor Is Coupled to the Activation of c-Jun N-Terminal Kinase, Mol Pharmacol. 2000 October; 58(4):814-20.

(8) Martin Wagner et al, Gene expression analysis of an epidermolysis bullosa simplex Dowling-Meara cell line by subtractive hybridization: recapitulation of cellular differentiation, migration and wound healing, Exp Dermatol. 2012 February; 21(2):111-7.

(9) Werner S and Munz B, Suppression of keratin 15 expression by transforming growth factor beta in vitro and by cutaneous injury in vivo, Exp Cell Res. 2000 Jan. 10; 254(1):80-90.

(10) Thomas Lettner et al, MMP-9 and CXCL8/IL-8 Are Potential Therapeutic Targets in Epidermolysis Bullosa Simplex, PLoS One. 2013 Jul. 19; 8(7):e703.

(11) Ramot Y et al, A novel control of human keratin expression: cannabinoid receptor 1-mediated signaling down-regulates the expression of keratins K6 and K16 in human keratinocytes in vitro and in situ. Peer J. 2013 Feb. 19; 1:e40.

(12) Dvorak M et al, Histamine induced responses are attenuated by cannabinoid receptor agonist in human skin. Inflamm Res 2003; 52:238-45.

(13) Stander S et al, Topical cannabinoid agonists. An effective new possibility for treating chronic pruritus. Hautarzt. 2006 September; 57(9):801-7.

(14) Pini A et al, The role of cannabinoids in inflammatory modulation of allergic respiratory disorders, inflammatory pain and ischemic stroke. Curr Drug Targets. 2012 June; 13(7):984-93.

(15) Gaffal E et al, Anti-inflammatory activity of topical THC in DNFB-mediated mouse allergic contact dermatitis independent of CB1 and CB2 receptors. Allergy. 2013 August; 68(8):994-1000.

(16) Richardson J D et al, Cannabinoids reduce hyperalgesia and inflammation via interaction with peripheral CB1 receptors. Pain. 1998 March; 75(1):111-9.

(17) Amaya F et al, Induction of CB1 cannabinoid receptor by inflammation in primary afferent neurons facilitates antihyperalgesic effect of peripheral CB1 agonist. Pain. 2006 September; 124(1-2):175-83.

(18) Kozela E et al, Cannabinoids decrease the th17 inflammatory autoimmune phenotype. J Neuroimmune Pharmacol. 2013 December; 8(5):1265-76.

(19) Feng R et al, Antagonism of cannabinoid receptor 2 pathway suppresses IL-6-induced immunoglobulin IgM secretion. BMC Pharmacol Toxicol. 2014 Jun. 9; 15:30.

(20) Appendino G et al. Antibacterial cannabinoids from *Cannabis sativa*: a structure-activity study. J Nat Prod. 2008; 71:1427-1430.
(21) Turner C E and Elsohly M A. Biological activity of cannabichromene, its homologs and isomers. J Clin Pharmacol. 1981 August-September; 21(8-9 Suppl): 283S-291S.
(22) Booker L et al. Evaluation of prevalent phytocannabinoids in the acetic acid model of visceral nociception. Drug Alcohol Depend. 2009 Nov. 1; 105(1-2):42-7.
(23) Yang Y Y et al. Effect of chronic CB1 cannabinoid receptor antagonism on livers of rats with biliary cirrhosis. Clin Sci (Lond). 2007 May; 112(10):533-42.
(24) Teixeira-Clerc F et al. CB1 cannabinoid receptor antagonism: a new strategy for the treatment of liver fibrosis. Nat Med. 2006 June; 12(6):671-6. Epub 2006 May 21.
(25) Rawal S Y et al. Effect of cannabidiol on human gingival fibroblast extracellular matrix metabolism: MMP production and activity, and production of fibronectin and transforming growth factor β. J Periodontal Res. 2012 June; 47(3):320-9.
(26) Pauline Wong and Pierre A. Coulombe. Loss of keratin 6 (K6) proteins reveals a function for intermediate filaments during wound repair. J Cell Biol. 2003 Oct. 27; 163(2): 327-337.
(27) Paladini R D, Takahashi K, Bravo N S and Coulombe P A. 1996. Onset of re-epithelialization after skin injury correlates with a reorganization of keratin filaments in wound edge keratinocytes: defining a potential role for keratin 16. Journal of cell biology 132:381-397.
(28) Rotty J D and Coulombe P A 2012. A wound-induced keratin inhibits Src activity during keratinocyte migration and tissue repair. Journal of Cell Biology. 197:381-389.
(29) Zhang J, Chen L, Xiao M, Wang C, Qin Z. FSP1+ fibroblasts promote skin carcinogenesis by maintaining MCP-1-mediated macrophage infiltration and chronic inflammation. Am J. Pathol. 2011 January; 178(1):382-90.
(30) Yoshimura T, Galligan C, Takahashi M, Chen K, Liu M, Tessarollo L, Wang J M. Non-Myeloid Cells are Major Contributors to Innate Immune Responses via Production of Monocyte Chemoattractant Protein-1/CCL2. Front Immunol. 2014 Jan. 7; 4:482.
(31) Chen C C, Wang L, Plikus M V, Jiang T X, Murray P J, Ramos R, Guerrero-Juarez C F, Hughes M W, Lee O K, Shi S, Widelitz R B, Lander A D, Chuong C M. Organ-level quorum sensing directs regeneration in hair stem cell populations. Cell. 2015 Apr. 9; 161(2):277-90. doi: 10.1016/j.cell.2015.02.016.
(32) Roth W, Reuter U, Wohlenberg C, Bruckner-Tuderman L, Magin T M. Cytokines as genetic modifiers in K5−/− mice and in human epidermolysis bullosa simplex. Hum Mutat. 2009 May; 30(5):832-41. doi: 10.1002/humu.20981.
(33) Boukamp P, Petrussevska R T, Breitkreutz, Hornung J, Markham A and Fuseing N E. 1988. Normal keratinization in a spontaneously immortalized aneuploidy human keratinocyte cell line. J. of Cell Biology. 106:761-771.
(34) Toth B I, Dobrosi N, Dajnoki A, Czifra G, Olha A, Szollosi A G, Juhasz I, Sugawara K, Paus R and Biro T. 2011. Endocannabinoids modulate human epidermal keratinocyte proliferation and survival via the sequential engagement of cannbinoid receptor-1 and transient receptor potential vanilloid-1. Journal of Investigational Dermatology. 131: 1095-1104.
(35) Lloyd C et al. The Basal Keratin Network of Stratified Squamous Epithelia: Defining K15 Function in the Absence of K14. 1995. J Cell Biol. 129: 1329-1344.
(36) Mazzalupo S. et al. Role for Keratins 6 and 17 During Wound Closure in Embryonic Mouse Skin. 2003. Dev Dyn. 226(2): 356-65.

EXAMPLES

Example 1: Keratin Expression in HaCat Cells is Modulated by Cannabinoids

Materials to be tested were Phyto-Cannabinoids cannabidiols (CBD), cannabidiolic acid (CBDA), cannabinol, (CBN), cannabidiols:cannabinol (1:0.1 µM), cannabidiols:cannabinol (0.1:1 µM), and cannabidiols:cannabinol (1:1 µM).

Cell culturing was performed as follows: HaCaT, human immortalized keratinocyte cell line was cultured in Dulbecco's Modified Eagle Medium (DMEM; Life Technologies Hungary Ltd.) supplemented with 10 (V/V) % fetal bovine serum (FBS; Life Technologies Hungary Ltd.) and antibiotics mixture (penicillin and streptomycin in 1:100; PAA Laboratories GmbH, Pasching, Austria) and Fungizone® Antimicotic (in 1:200; Life Technologies Hungary Ltd.) respectively.

Cells were cultured at 37° C. in humidified, 5% $CO_2$-containing atmosphere, the medium was changed every other day, and cells were sub-cultured at 70-80% confluence in all cases. For the drug treatment, the medium was changed every day.

Quantitative real-time polymerase chain reaction (qPCR) was performed as described previously previously on a Roche Light Cycler 480 QPCR System (Roche Applied Sciences) using the 5' nuclease assay. qPCR is described in S. A. Bustin et al., "The MIQE Guidelines: Minimum Information for Publication of Quantitative Real-Time PCR Experiments," *Clin. Chem.* 55: 611-622 (2008). Total RNA was isolated using TRIzol (LifeTechnologies), DNase treatment was performed according to the manufacturer's protocol, and then 1 kg of total RNA were reverse-transcribed into cDNA by using High Capacity cDNA Kit from Life Technologies Corporation. PCR amplification was performed by using the TaqMan primers and probes (assay IDs: Hs00361185_m1 for Keratin 5, Hs00265033_m1 for Keratin 14, Hs00267035_m1 for Keratin 15).

As internal control, expression of peptidyl-prolyl isomerase A (PPIA), glyceraldehyde-3-phosphate dehydrogenase (GAPDH) and actin beta (ACTB) was determined (assay IDs: Hs99999904_m1 for PPIA, Hs99999905_m1 for GAPDH and Hs99999903_m1 for ACTB). The amount of the transcripts was normalized to those of the housekeeping gene using the ΔCT method. When indicated, the results were then normalized to the expression of the vehicle control or the LTA-treated culture (ΔΔCT method), and were plotted as mean±SD of 3 technical replicates.

Western blotting was used to determine the expression of keratins in HaCaT cells. The initial cell count was $2 \times 10^5$ cells/per Petri dish in "small" (d=35 mm) Petri dishes in 1.5 mL culture medium (DMEM supplemented with FBS (10%), antibiotics and antimycotics). Cells were harvested at the following stages: preconfluent (proliferating) and post-confluent (differentiating). The combinations employed for Western blotting were cannabidiols:cannabinol (1:0.1 µM), cannabidiols:cannabinol (0.1:1 µM), and cannabidiols:cannabinol (1:1 µM). The genes whose expression was investigated by Western blotting were GAPDH or β-actin as internal controls and (K1), K5, K6, (K10), K14, K15, K16, and K17. Protein samples were used at 5 µl/well. The standards used were PageRuler Plus Prestained (Pierce). Electrophoresis was at 100 volts.

Transfer was performed using the Trans-Blot® Turbo™ Transfer System (1.3 A, 25 V, 7 min). The primary antibody was used at 1:100 in 5% milk containing PBS; overnight at 4° C.; the primary antibody was guinea pig anti-human keratins: anti human Keratin 1, Keratin 5, Keratin 6, Keratin 14, Keratin 15, Keratin 16, Keratin 17 (from Lutz Langbein; predicted band: ~67 kDa, ~58 kDa, ~56 kDa, ~56.5 kDa, 50 kDa, 45 kDa, 48 kDa, 46 kDa). The secondary antibody was used at 1:1000 in 5% milk containing PBS; 1 hr at RT; the secondary antibody was HRP-conjugated goat anti-Guinea Pig IgG (Santa Cruz). The loading controls were Rabbit anti-human GAPDH (Novus Biologicals; Cat. No.: NB300-322; predicted band: ~37 kDa) or anti-human β-actin (Sigma-Aldrich; Cat. No.: A2668; predicted band: ~42 kDa) 1:1000 in 5% milk containing PBS. HRP-conjugated goat anti-rabbit IgG Fc-segment (BioRad 170-6515; 1:1000) was used.

For statistical analysis, data were analyzed and graphs were plotted by using Origin Pro Plus 6.0 software (Microcal, Northampton, MA, USA), using Student's two-tailed two samples t-test and P<0.05 values were regarded as significant differences.

For western blotting in the wound healing analysis, epithelial-mesenchymal transition (EMT) is a critical element of epithelial biology, cancer development, and fibrosis. Chronic activation of TGF-β-signaling in the skin ultimately leads to fibrosis (keloid). EMT of keratinocytes is adaptive response in the normal wound healing process. It is characterized by decrease of E-cadherin (important element of keratinocyte integrity and tight junction formation) expression and upregulation of cellular fibronectin (Fibronectin-EDA) production. The latter is a very important protective element of epithelial cells during mucosal tissue repairs. Chronic EMT of keratinocytes in psoriasis has been shown to be a key element of disease pathogenesis.

Total protein extracts were prepared from synchronized HaCaT cells at different times. Mouse monoclonal antibodies directed against the extracellular domain of human E-cadherin (1 µg/ml; clone SHE78-7, Zymed, San Francisco, CA) and mouse monoclonal antibody specific for human extra domain (EDA sequence) of cellular fibronectin at 1:200 dilution (ICN Biochemicals) were used in this assay. β-tubulin was used as positive control.

Figure 21:
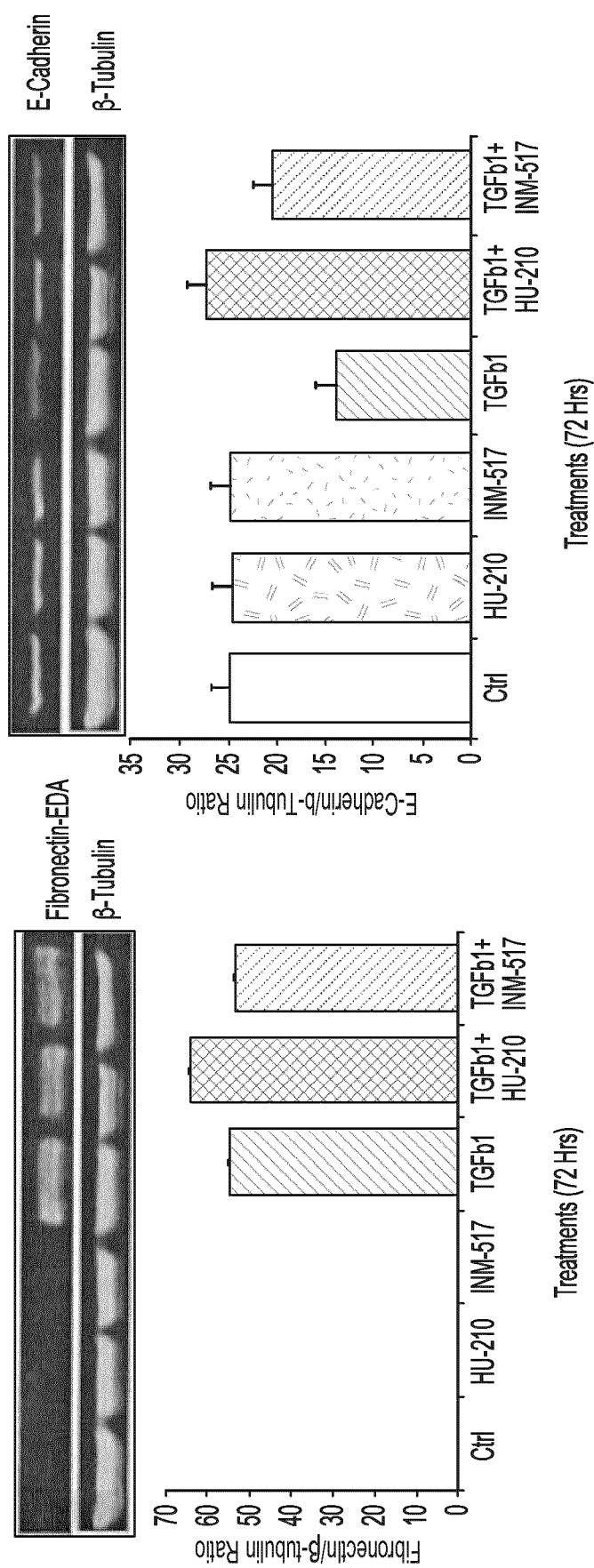
FIG. 21 shows the activity of cannabinoids in would healing by upregulating extra domain A (EDA)-fibronectin (left panel). TGF-β-induced inhibition of E-cadherin is rescued by cannabinoids (right panel).

Results are shown in FIG. 21. According to the results shown in FIG. 21, fibronectin-EDA is induced by TGF-β during wound healing and important for cell migration (wound closure) and adherence. INM-750 does not change TGF-β-induced fibronectin expression in human keratinocytes. E-cadherin is a major component in preserving epithelial integrity. During wound healing through TGF-β E-cadherin is depressed. INM-750 rescues TGF-β-induced downregulation of E-cadherin by human keratinocytes and thus contributes to epidermal integrity.

The effects of a mixture of 10:1 ratio of cannabidiols (CBD) (particularly Δ²-cannabidiol) and cannabinol (CBN) on the expression of K5, K14 and K15 using quantitative real-time polymerase chain reaction (qPCR) using human epidermal keratinocyte (HaCaT) cell line were analyzed. Cell culture and qRT-PCR were performed according to the protocol described by References (33) and (34). Evaluation of the cellular response was made using RT-qPCR (mRNA level). To obtain high-confidence results, three different housekeeping proteins (PPIA, GAPDH, ACTB) of keratinocytes were used as internal controls. Two active components of the mixture with different concentration were used in this study (0.1:0.1 µM, 0.1:1 µM and 1:0.1 µM).

The results (FIG. 4) indicate that the mixture of 10:1 ratio of cannabidiols and cannabinol downregulates K14 and in the same time upregulates the expression of K15 in the cells harvested preconfluent (proliferating) and postconfluent (differentiating) keratinocytes whereas the mixture upregulates the K17 during postconfluent (differentiating) phase. Both active components of INM-750 promote the expression of K15 and K17 at 0.1:0.1 µM ratio, while suppressing the expression of K14.

FIG. 5A is a table showing the relative expression of different keratins in HaCaT keratinocytes with different concentrations of INM-750 as determined by qPCR. FIG. 5B is a table showing the relative expression of different keratins in HaCaT keratinocytes with different concentrations of CBD:CBN as determined by qPCR (the internal control is PPIA). FIG. 5C is a table showing the effect of different concentrations of CBD:CBN at a 10:1 ratio on keratin expression profile (the internal control is β-actin). Two active components of the mixture of 10:1 ratio of cannabidiols and cannabinol at a ratio of 1:0.1 µM promote the expression of K6 and K17 during postconfluent (differentiating) phase while upregulating K15 expression at preconfluent (proliferating) phase.

Figure 6:
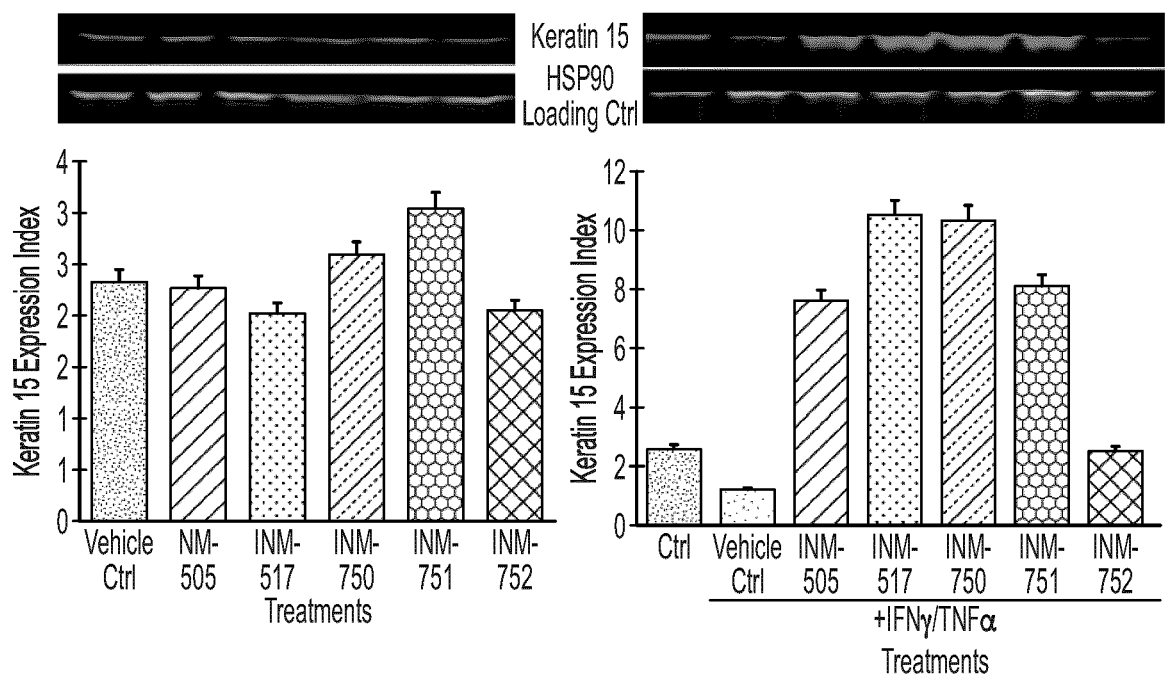
FIG. 6 shows the effects of the mixture of 10:1 ratio of cannabidiols and cannabinol on the expression of keratins in human epidermal (HaCaT) keratinocytes by quantitative western blot analysis. The left panel shows the results without IFNγ/TNFα pretreatment; the right panel shows the results with IFNγ/TNFα pretreatment.

The effects of the two active components of the mixture of 10:1 ratio of cannabidiols and cannabinol or the two individual components of the mixture on the expression of K15 in HaCaT keratinocytes using Western blot analysis were determined; the results are shown in FIG. 6. FIG. 6 shows the effects of phytocannabinoids CBD and/or CBN on the expression of K15. In FIG. 6, "INM-505" is cannabidiols, "INM-517" is cannabinol; "INM-750" is a mixture of 10:1 ratio of cannabidiols and cannabinol (1:0.1 µM); "INM-751" is a 1:10 mixture of cannabidiols and cannabinol; and "INM-752" is a 1:1 mixture of cannabidiols and cannabinol each at 1 µM ("INM-752").

None of the cannabinoids tested show the influence on the expression of K15. However, if the cells were pretreated with pro-inflammatory agents (IFNγ/TNFα), CBD and CBN promote the expression of K15 either individually or in combination. The left panel shows the results without IFNγ/TNFα pretreatment; the right panel shows the results with IFNγ/TNFα pretreatment. None of the cannabinoids tested show any influence on the expression of K15. However, when the HaCaT keratinocyte cells were pre-treated with pro-inflammatory agents (IFN/TNFα), both components of INM-750 either individually or in combination promote the expression of K15 except INM-752 where 1:10 ratio of two active components of INM-750 was used. Densitometry data of three independent immunoblots (FIG. 7) also showed that INM-750 strongly upregulates keratin 15 but not keratin 5 and 14 proteins in in vitro cultures of human keratinocyte cell line (HaCaT cells).

Figure 7:
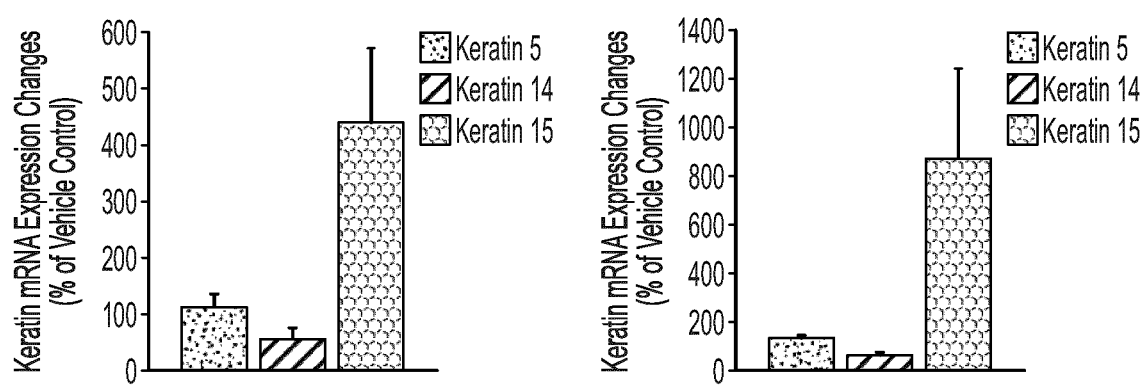
FIG. 7 shows the effects of the mixture of 10:1 ratio of cannabidiols and cannabinol on the expression of keratins K5, K14, and K15 in human epidermal (HaCaT) keratinocytes. The mixture significantly increases the expression of K15 without significantly increasing the expression of the other keratins (left panel, cells at proliferation stage; right panel, cells at differentiation stage).

FIG. 7 shows the effects of the mixture of 10:1 ratio of cannabidiols and cannabinol on the expression of keratins K5, K14, and K15 in human epidermal (HaCaT) keratinocytes. The mixture significantly increases the expression of K15 without significantly increasing the expression of the other keratins (left panel, cells at proliferation stage; right panel, cells at differentiation stage).

Figure 8:
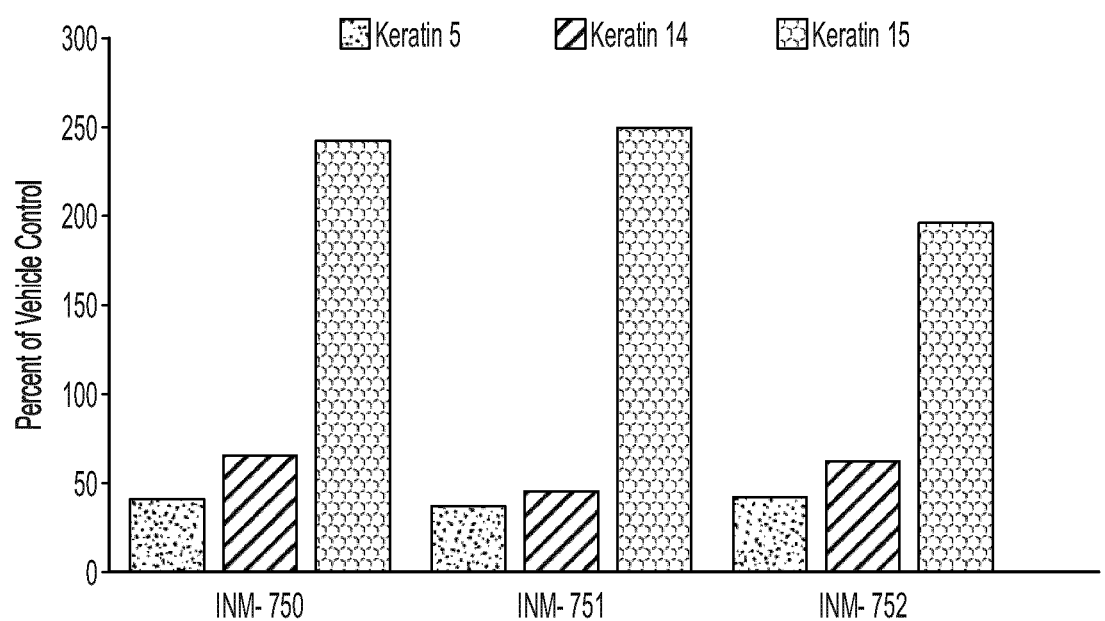
FIG. 8 shows that different ratios of cannabidiols and cannabinoids (INM-750 is a 10:1 ratio of cannabidiols and cannabinol at a ratio of 1:0.1 μM; INM-751 is a 1:10 mixture of cannabidiols and cannabinol at a ratio of 0.1:1 μM; INM-752 is a 1:1 mixture of cannabidiols and cannabinol each at 1 μM) upregulate the synthesis of K15 but not K5 and K14 in HaCaT cells.

FIG. 8 illustrates that different combinations of cannabinoids had different effects. A 10:1 ratio of cannabidiols and cannabinol ("INM-750") strongly upregulates keratin 15 but not keratin 5 and 14 proteins in in vitro cultures of human keratinocyte cell line (HaCaT cells). Densitometry data from one representative of three independent immunoblots are shown in FIG. 8. Results are also shown in FIG. 8 for a 1:10 mixture of cannabidiols and cannabinol (0.1:1 µM) ("INM-751") and a 1:1 mixture of cannabidiols and cannabinol each at 1 µM ("INM-752").

Investigated keratinocyte genes include: K5, K6, K14, K15, K16 and K17. Modulation of these genes may have potential beneficial effects on EBS. The K14 gene was downregulated in the cells treated with 10 µM cannabinol and this is consistent with the results of quantitative real-time polymerase chain reaction (qPCR). When the combination of two active components of the mixture of cannabidiols and cannabinol (0.1-0.1 µM) treatment were applied the K6 and K17 genes were upregulated in post-confluent (differentiating) stages.

The latter is consistent with the finding reported herein of the results of the quantitative real-time polymerase chain reaction (qPCR). It is worth noting that the two active components of the mixture of cannabidiols and cannabinol at either 0.1-1 µM or 1-0.1 µM ratio levels downregulate the K5 expression (FIG. 4) in pre-confluent (proliferating) stage which may exert beneficial effect in EBS. Based on the results of qPCR and Western blot (FIGS. 5A-C, and 6), the combination of INM-750 (a 10:1 ratio of cannabidiols and cannabinol at a ratio of 1:0.1 µM) appears to be the most promising choice for EBS. The importance of modulation of different keratinocyte genes by cannabinoid compounds lies in the fact that during the wound healing process restoration of barrier function is essential, and major contribution to this process is skin re-epithelialization—the migration of keratinocytes into the wound site and subsequent establishment of a new stratified epidermis. The results reported herein show that the treatment of CBD:CBN not only upregulates K15 but also K6 and K17 and therefore it is believed that this upregulation of different keratinocyte genes has strong potential to beneficially impact one or more diseases or conditions associated with or caused by intermediate filament dysfunction such as EBS.

The mixture of cannabidiols and cannabinol at a 10:1 ratio of cannabidiols to cannabinol also accelerates the wound healing process. In terms of expedited wound healing, the present inventors hypothesized that CB1 agonists might be used to help keratinocyte migration and wound healing by decreasing KRT6B expression. Initial experimental results show that the mixture of cannabidiols and cannabinol at a 10:1 ratio of cannabidiols to cannabinol suppresses the activation of KRT6B genes and improves wound healing due to increased keratinocyte migration. The efficacy of the mixture of cannabidiols and cannabinol at a 10:1 ratio of cannabidiols to cannabinol was demonstrated in wound healing assays.

In analysis of the effect of cannabinoids on wound healing, the electric cell-substrate impedance-sensing (ECIS) wounding assay replaces the traditional "scratch" or "scrape" assays. Instead of disrupting the cell layer mechanically with a toothpick, needle or pipette tip and following the migration of cells to "heal" the wound with a microscope, ECIS employ electrical signals to both wound and monitor the healing process. ECIS electrical wounding is only directed at the small population of cells in contact with the active 250-µm diameter ECIS electrode, producing a well-defined 250-µm wound that can be verified both with the ECIS measurement and with vital staining.

Unlike the traditional scrape method, with the ECIS wound the protein coating is unaffected by the current and remains fully intact. Once ECIS electrically wounds the cells, it returns to its normal mode to immediately follow the healthy neighboring cells as they migrate inward to replace the killed cells. This assay was used to test the effect of individual cannabinoids on wound healing for both acute and chronic wound healing.

Figure 9:
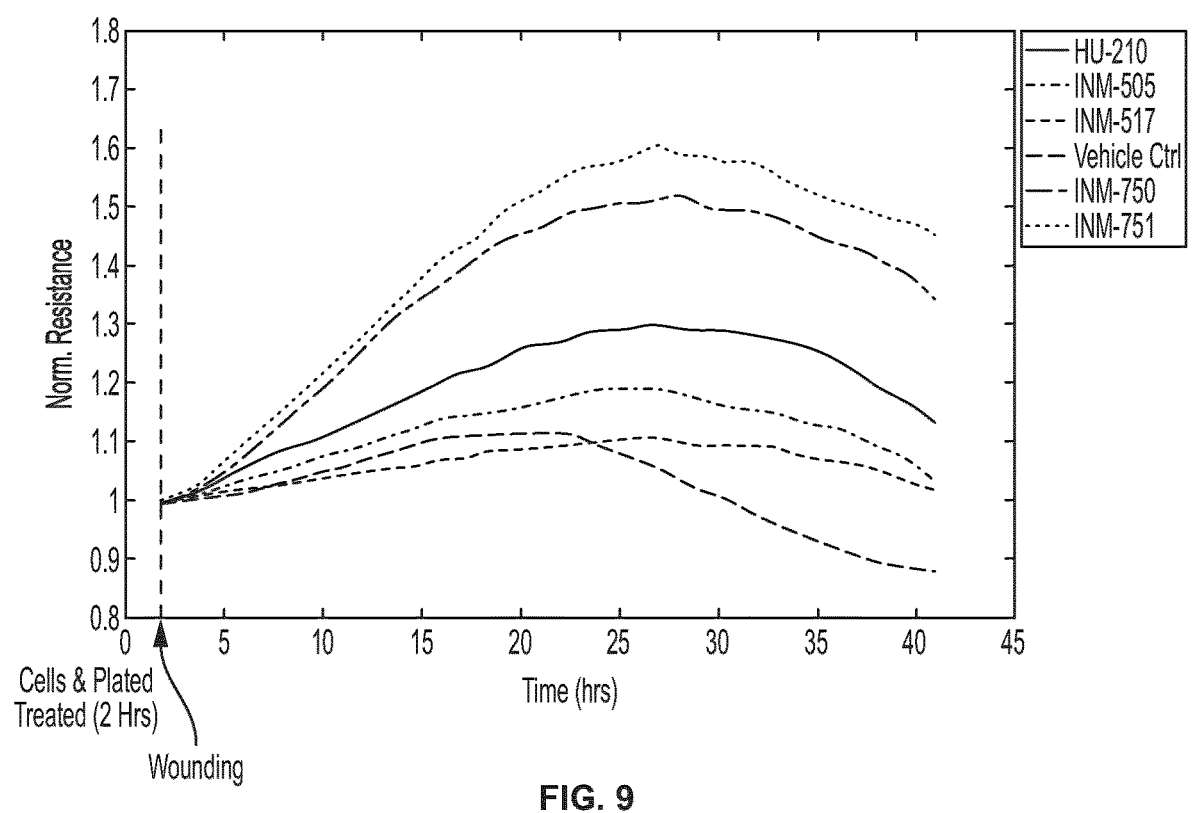
FIG. 9 shows in vitro acute wound healing measurements where HaCaT cells are pretreated for 2 hr before introducing wounding by the Electric Cell-substrate Impedance Sensing (ECIS) system. The effect of different ratios of cannabidiols and cannabinol on the wound healing process was measured for 40 hours. "Norm. Resistance" is a measure of the percent coverage of the cells over the electrode after injury. "INM-750" is a 10:1 ratio of cannabidiols and cannabinol at a ratio of 1:0.1 μM and "INM-751" is a 1:10 mixture of cannabidiols and cannabinol at a ratio of 0.1:1 M.

In the acute wound model, the HaCaT cells were treated with various ratio of cannabidiols, cannabinol, and HU-210 (6aR,10aR)-9-(hydroxymethyl)-6,6-dimethyl-3-(2-methyloctan-2-yl)-6H,6aH,7H,10H,10aH-benzo[c]isochromen-1-ol) (at 1 µM; a synthetic THC analog) in suspension for 2 hr, and plated into array chip chambers. Repair (setup) and barrier function of cell monolayer was monitored for 40 hr by measuring of electrode resistance using an electric cell-substrate impedance sensing (ECIS) system (Applied Biophysics, Troy, NY) in the individual HaCaT cultures (FIG. 9). FIG. 9 shows in vitro acute wound healing measurements where HaCaT cells are pretreated for 2 hr before introducing wounding by the Electric Cell-substrate Impedance Sensing (ECIS) system. The effect of different ratios of cannabidiols and cannabinol on the wound healing process was measured for 40 hours. "Norm. Resistance" is a measure of the percent coverage of the cells over the electrode after injury. "INM-750" is a 10:1 ratio of cannabidiols and cannabinol at a ratio of 1:0.1 µM and "INM-751" is a 1:10 mixture of cannabidiols and cannabinol at a ratio of 0.1:1 µM.

Figure 10:
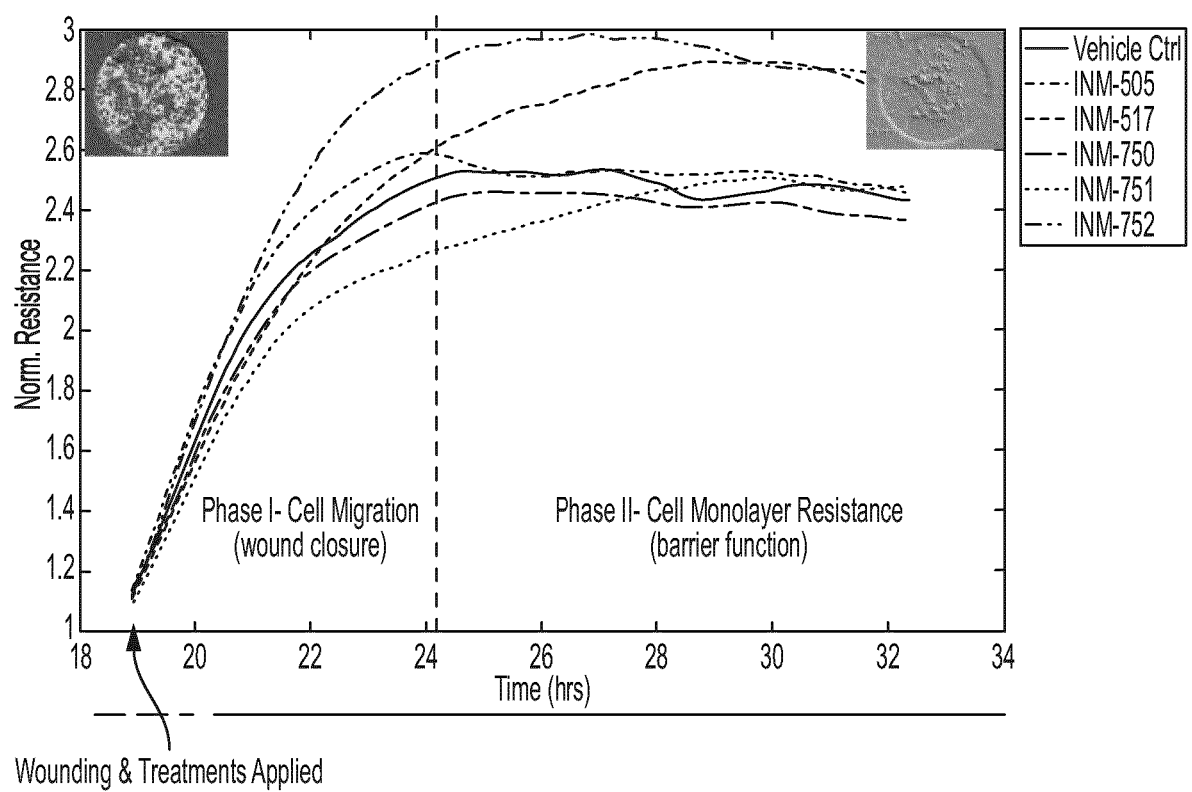
FIG. 10 shows in vitro chronic wound healing process measurements in HaCaT cells where cell wounding and treatment are applied simultaneously by the Electric Cell-Substrate Impedance Sensing (ECIS) Wounding Assay. The wound healing process is divided in two parts: wound closure and restoration of barrier functions. The following compositions were tested: a 10:1 ratio of cannabidiols and cannabinol at a ratio of 1:0.1 μM ("INM-750"), a 1:10 mixture of cannabidiols and cannabinol at a ratio of 0.1:1 μM ("INM-751"), and a 1:1 mixture of cannabidiols and cannabinol each at 1 μM ("INM-752").

Chronic wound healing is the most representative model for EBS treatment. In this model wounding and treatments are applied simultaneously after 18 h of incubation of HaCaT cells and efficacy of different combinations of the mixture of cannabidiols and cannabinol on cell migration and cell monolayer resistance mimicking wound closure and skin regeneration were measured (FIG. 10). The results indicate the need to find an optimum ratio of the two active components of cannabinoids for EBS treatment. Due to the pleiotropic nature and strong cell-type dependence of the cutaneous endocannabinoid system mediated functions, it requires careful judgment on selection optimum combination and ratio of cannabinoid compounds. As mentioned above, for optimum efficacy of the treatment of EBS, the section criteria are based on the efficacy in four hallmarks of the disease.

FIG. 10 shows in vitro chronic wound healing process measurements in HaCaT cells where cell wounding and treatment are applied simultaneously by the Electric Cell-substrate Impedance Sensing (ECIS) Wounding Assay. The wound healing process is divided in two parts: wound closure and restoration of barrier functions. The following compositions were tested: a 10:1 ratio of cannabidiols and cannabinol at a ratio of 1:0.1 µM ("INM-750"), a 1:10 mixture of cannabidiols and cannabinol ("INM-751"), and a 1:1 mixture of cannabidiols and cannabinol ("INM-752").

Figure 11:
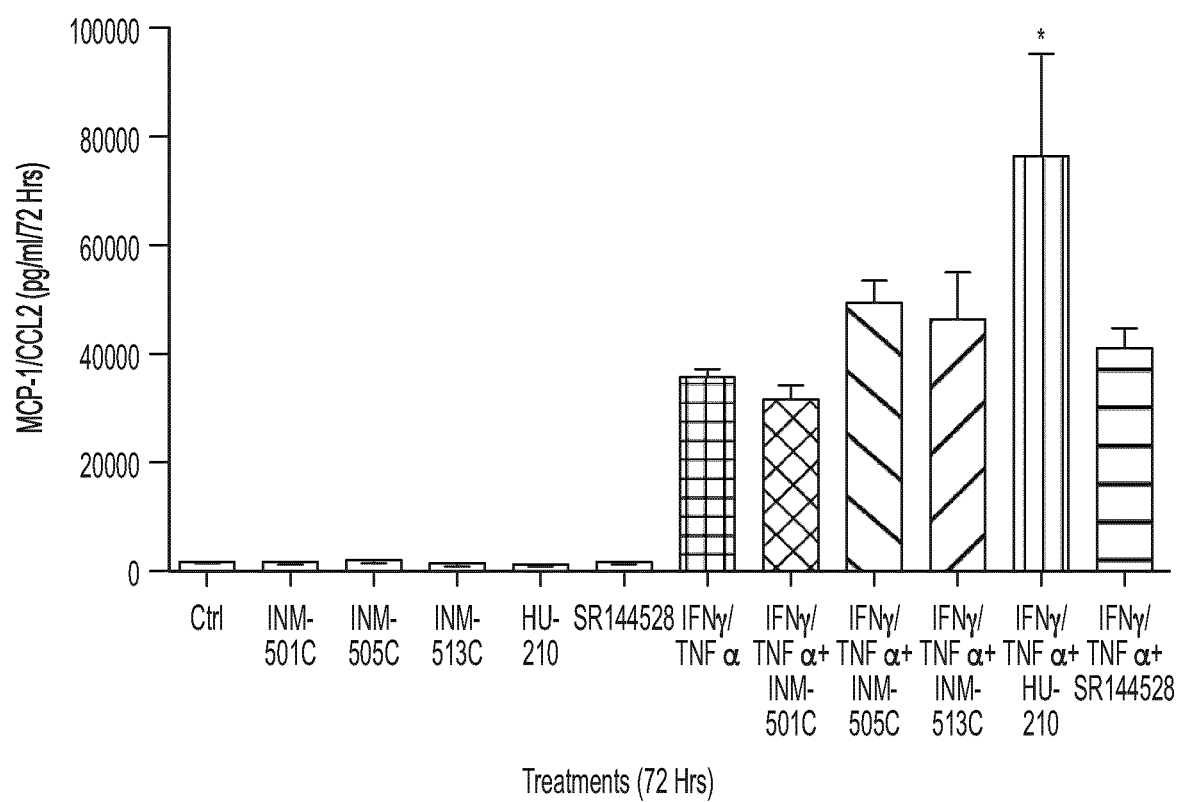
FIG. 11 is a graph showing the effect of various cannabinoids on the upregulation of IFNγ/TNFα-induced CCL2/MCP-1 production by human keratinocytes; the upregulation of IFNγ/TNFα-induced CCL2/MCP-1 production increases skin defense and regeneration.

Additionally, the mixture of cannabidiols and cannabinol modulates CCL2/MCP-1 production by human keratinocytes in vitro (FIG. 11). The chemokine (C—C motif) ligand 2 (CCL2) also known as Macrophage Chemotactic Protein 1 (MCP-1) is a chemokine playing critical role in skin inflammation and repair processes (Reference (29)). CCL2 attracts macrophages to the skin wound area, and regulates trafficking of skin stem cells and Langerhans cells during the regenerative phase of skin wound healing (Reference (30)). The most recent study has been shown a key role for CCL2 in the skin homeostasis and innate immunity (Reference (31)). CCL2 expression is strongly induced by pro-inflammatory cytokines, like IL-1β, TNF-α and IFN-γ, and it is abundantly produced by epidermis in EBS by an unknown pathomechanism (Reference (32)).

Cannabinoids are known for their potential anti-inflammatory action on human blood leukocytes. However, their effects on basal and inflammatory induced CCL2 production by human keratinocytes have not been studied. The effects of $\Delta^9$-tetrahydrocannabinol, cannabidiols, cannabigerol, HU-210, and SR144528 (5-(4-chloro-3-methylphenyl)-1-[(4-methylphenyl)methyl]-N-[(1S,2S,4R)-1,3,3-trimethyl-bicyclo[2.2.1]heptan-2-yl]-1H-pyrazole-3-carboxamide; a CB2 inverse agonist) were studied on basal and pro-inflammatory cytokine-induced CCL2 production by human keratinocytes (HaCaT) in in vitro cultures.

Immortalized human skin keratinocytes (HaCaT) were used as an in vitro model for the screening of CB1/CB2 agonists. HaCaT cells were seeded into 24-well plates ($1\times10^5$ cells/well/ml) in DMEM cell culture medium supplemented with 10% FBS and antibiotics/antimycotics, and allowed to form subconfluent cultures for 24 hr. Before experiments, cell culture medium was replaced by DMEM supplemented with 1% FBS and antibiotics/antimycotics, and the cannabinoid compounds referred to above (all at 1 mM concentration, Cayman Chemical, Ann Arbor, MI) were added alone or with human recombinant Interferon (IFN)$\gamma$ and Tumor Necrosis Factor (TNF)$\alpha$ (both at 10 ng/ml concentrations, PeproTech, Rocky Hill, NJ), and HaCaT cells were cultured for 72 hrs. DMSO was used as a vehicle control. After 72 hr cell culture supernatants were collected, cleared by centrifugation and stored at $-80°$ C. before assays.

CCL2/MCP-1 concentrations were measured by Sandwich-ELISA using recombinant human MCP-1 as a standard, and PBS with 1% Bovine Serum Albumin as diluent buffer, and NUNC MaxiSorb flat bottom 96-well microplates as a carrier. Two independent experiments performed in duplicates. One-way ANOVA with multiply comparisons was used for statistical analysis by GraphPad Prism 6.01 software. Probability values were considered significant if they were less than 0.05.

The results indicate that CCL2/MCP-1 production is strongly induced by pro-inflammatory cytokines IFN$\gamma$/TNF$\alpha$ in human keratinocytes (HaCaT) after 72 hrs of stimulation. Tested cannabinoid compounds have no significant effects on basal CCL2 production, however cannabidiols, cannabigerol, and the most potent HU-210, at the tested concentrations, upregulated an IFN$\gamma$/TNF$\alpha$-induced CCL2 production by HaCaT cells.

Figure 12:
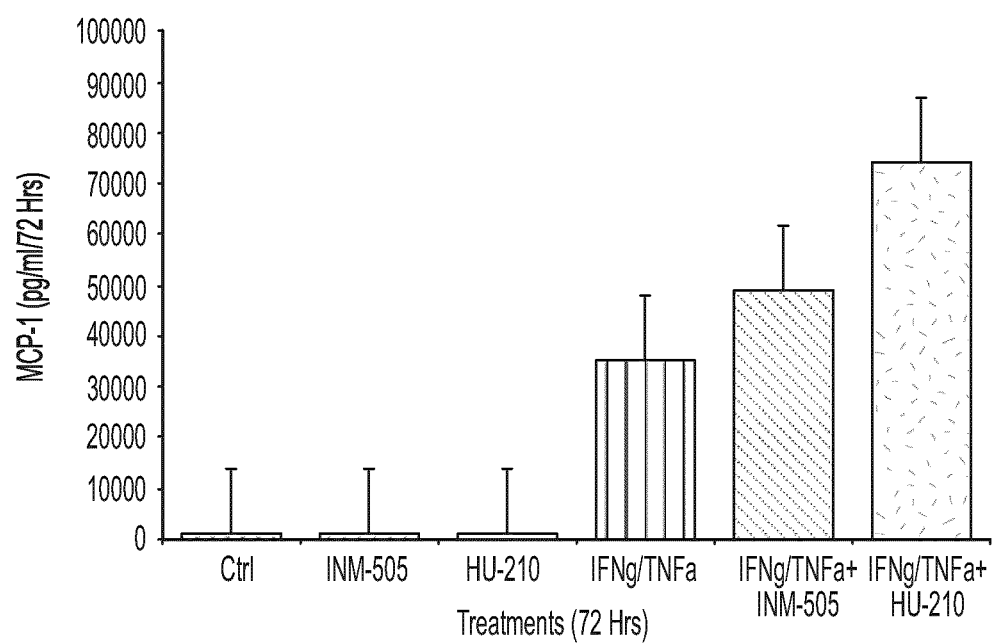
FIG. 12 is a summary graph showing that cannabinoids upregulate IFNγ/TNFα-induced CCL2/MCP-1 production by proliferating human keratinocytes in vitro.

$\Delta^9$-tetrahydrocannabinol has no significant effects on both basal and IFN$\gamma$/TNF$\alpha$-induced CCL2 production at 1 µM concentration compared with DMSO-treated controls (Ctrl). SR144528, the inverse CB2 agonist, did not significantly change both basal and IFN$\gamma$/TNF$\alpha$-induced CCL2 production by HaCaT cells (FIGS. 11 and 12). Cannabidiols, which are an active component of the mixture of cannabidiols and cannabinol described above, increases the skin defense and regeneration by upregulating IFN$\gamma$/TNF$\alpha$-induced CCL2/MCP-1 production by human keratinocytes.

The results are shown in FIG. 11 and FIG. 12. FIG. 11 is a graph showing the effect of various cannabinoids on the upregulation of IFN$\gamma$/TNF$\alpha$-induced CCL2/MCP-1 production by human keratinocytes; the upregulation of IFN$\gamma$/TNF$\alpha$-induced CCL2/MCP-1 production increases skin defense and regeneration. FIG. 12 is a summary graph showing that cannabinoids upregulate IFN$\gamma$/TNF$\alpha$-induced CCL2/MCP-1 production by proliferating human keratinocytes in vitro.

This result indicates that cannabinoid compounds are capable of modulating IFN$\gamma$/TNF$\alpha$-induced CCL2/MCP-1 expression by human keratinocytes in vitro. It seems both CB1 and CB2 receptors are involved in this action, since CB1/CB2 receptor agonist HU-210 produced the highest effect observed after 72 hrs exposure. Constitutive activation of CB2 receptor is not involved in these in vitro effects since SR144528 did not modulate both basal and IFN$\gamma$/TNF$\alpha$-induced CCL2 production of HaCaT keratinocytes. Both cannabidiols and cannabigerol increase the skin defense and regeneration by upregulating IFN$\gamma$/TNF$\alpha$-induced CCL2/MCP-1 production by human keratinocytes.

The anti-inflammatory properties of the mixture of cannabidiols and cannabinol described above were also demonstrated. The data presented herein shows that cannabidiols and HU-210 increase MCP-1 production by proliferating human skin epithelial cells (keratinocytes) and thus increases skin defense and regeneration by upregulating IFN$\gamma$/TNF$\alpha$-induced CCL2/MCP-1 production by human keratinocytes.

In terms of anti-inflammatory activity, cannabidiols activate CB2 receptors on mast cells, causing decreased release of pro-inflammatory mediators by these cells. IL-8 is the most potent chemoattractant for blood neutrophils and an important mediator of angiogenesis. Chronic IL-8 and neutrophil activation in the skin is an unfavorable element of skin pathology. Cannabidiols displayed highly selective inhibitory effect on IL-8 production by human keratinocytes. IL-6 is a pro-inflammatory cytokine and can be stimulated by IFN$\gamma$/TNF$\alpha$. The data presented herein indicate cannabidiols attenuate the production of IL-6 by IFN$\gamma$/TNF$\alpha$. The anti-inflammatory activity is shown in FIG. 13.

FIG. 13, left, is a graph showing that a 10:1 ratio of cannabidiols and cannabinol at a ratio of 1:0.1 µM inhibits IL-8 production. FIG. 13, right, is a graph showing that cannabinoids also inhibit basal IL-8 production. Both IL-8 production and IFN$\gamma$/TNF$\alpha$-induced IL-6 production are biomarkers of inflammation.

Example 2: Topical Cannabinoid Formulations and Skin Penetration

Figure 14:
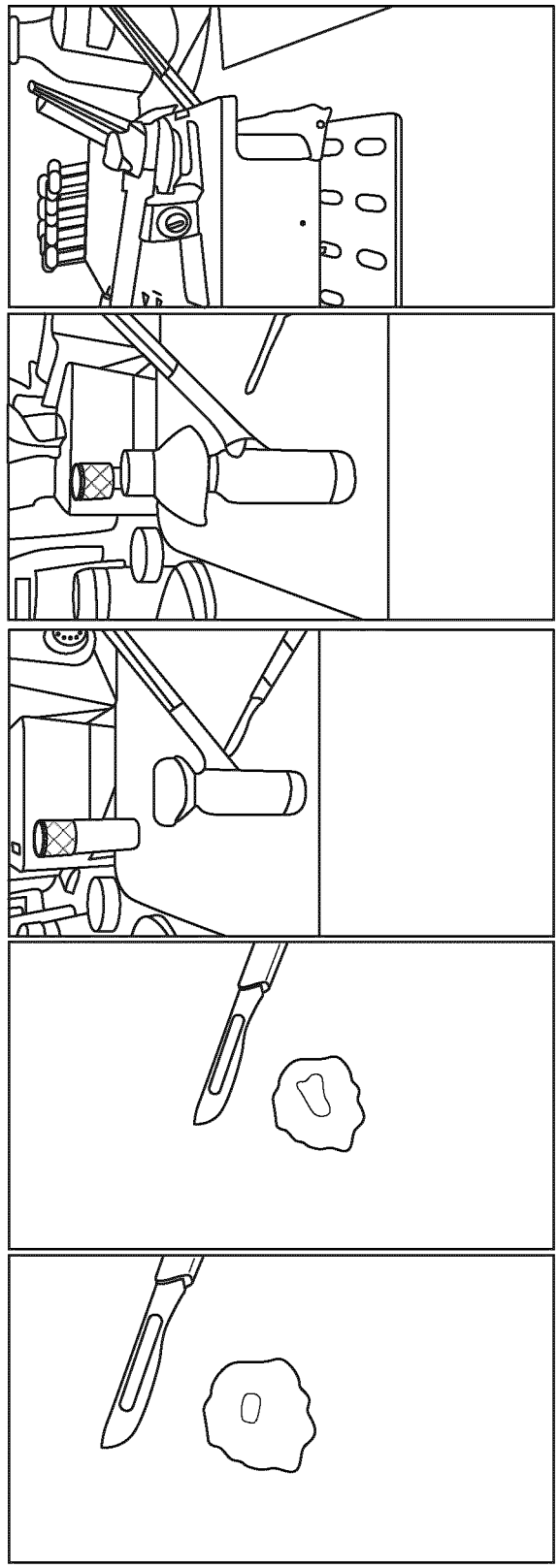
FIG. 14 shows the experimental setup for the determination of the efficacy of cannabinoid penetration through porcine skin using 0.6% cannabinoid in a formulation comprising LABRASOL® (caprylocaproyl polyoxyl-8 glycerides), poloxamer 407, lethicin, and isopropyl palmitate.
Figure 15:
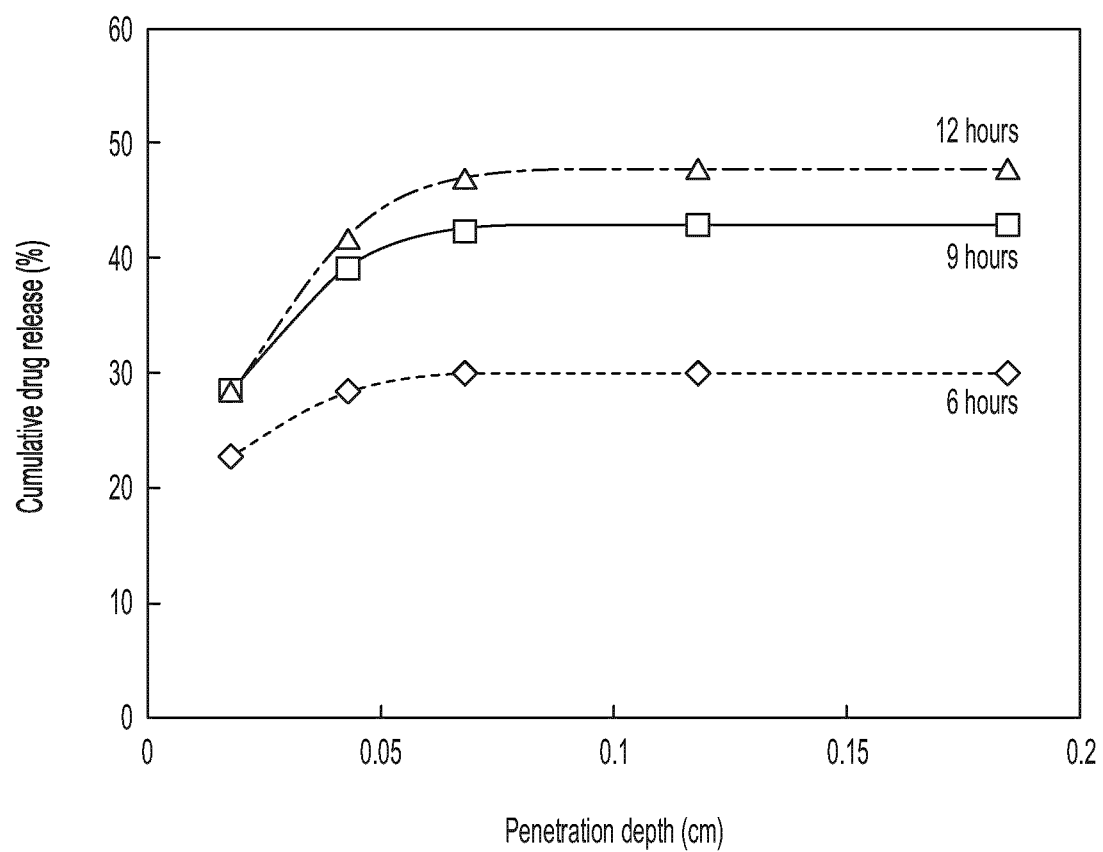
FIG. 15 is a graph showing the results from the penetration experiment of FIG. 14 (♦, 6 hours; ■, 9 hours; ▲, 12 hours).

Skin penetration of formulations described herein was measured according to the following procedure: the formulation was LABRASOL® (caprylocaproyl polyoxyl-8 glycerides), Plo-gel (Poloxomer 407, Lecithin, isopropyl palmitate). The formulation is applied to the center part of the circle and is rubbed to the skin using a scalpel. The sample is mounted to the top of a Franz diffusion cell with the outer layer of the skin facing upward. The receptor medium of the Franz cell is filled with phosphate buffer. The cap of the cell is mounted and clamped. This construct is placed inside the incubator/shaker for 18 hours at 32° C. (FIG. 14). FIG. 15 shows the results from the penetration experiment of FIG. 14 (•, 6 hours; ■, 9 hours; 1, 12 hours).

Figure 16:
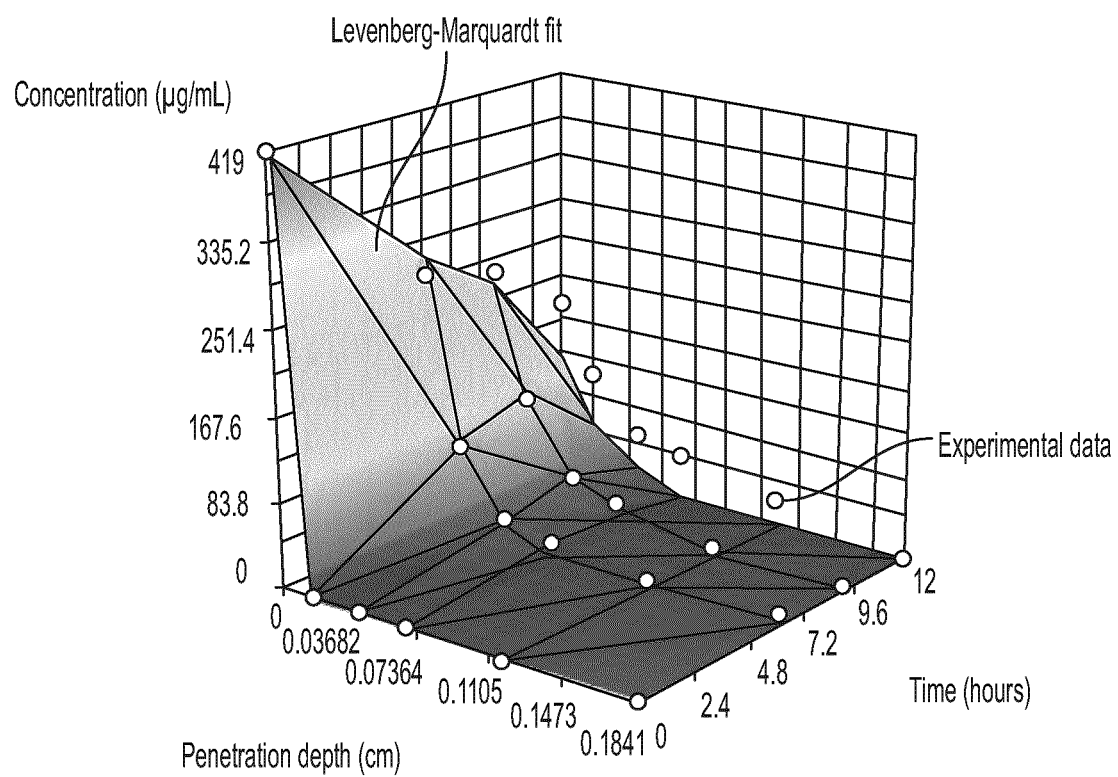
FIG. 16 shows a mathematical model of cannabinoid diffusion across skin based on the results of FIG. 15 using a Levenberg-Marquardt fit.
Figure 17:
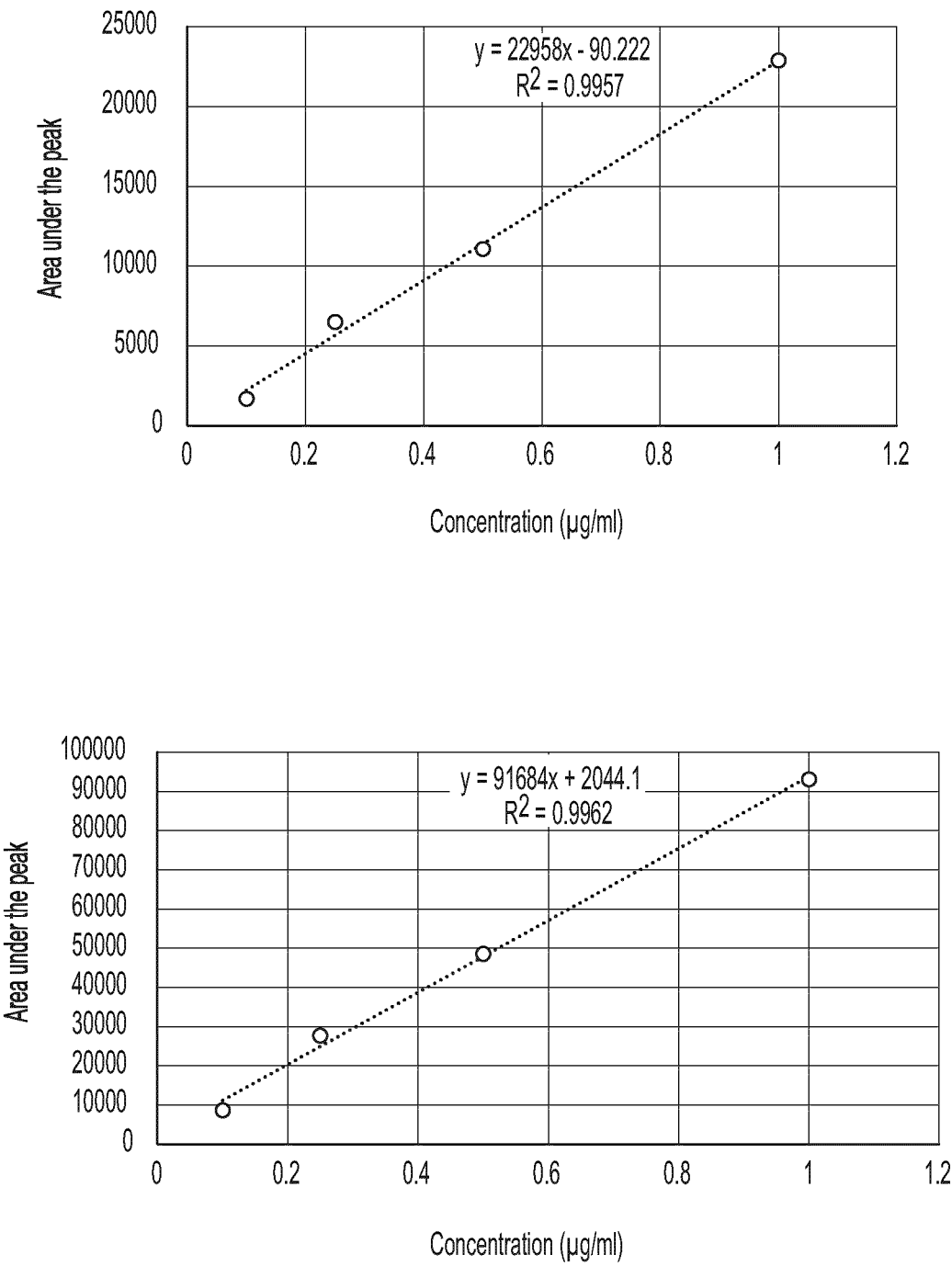
FIG. 17 is a graph showing the area under the curve for allantoin (top panel) and cannabidiol (bottom panel).

FIG. 16 shows a mathematical model of cannabinoid diffusion across skin based on the results of FIG. 15 using a Levenberg-Marquardt fit. FIG. 17 shows the area under the curve for allantoin (left panel) and cannabidiol (right panel). FIG. 18 shows that after 18 hours, most of the cannabinoid molecules are located in keratinocytes and basal cells. The total amount of the drug (cannabidiol) applied to the skin was 400 µg. Allantoin was used as a control.

Example 3: Cannabinoids and Wound Healing

Figure 19:
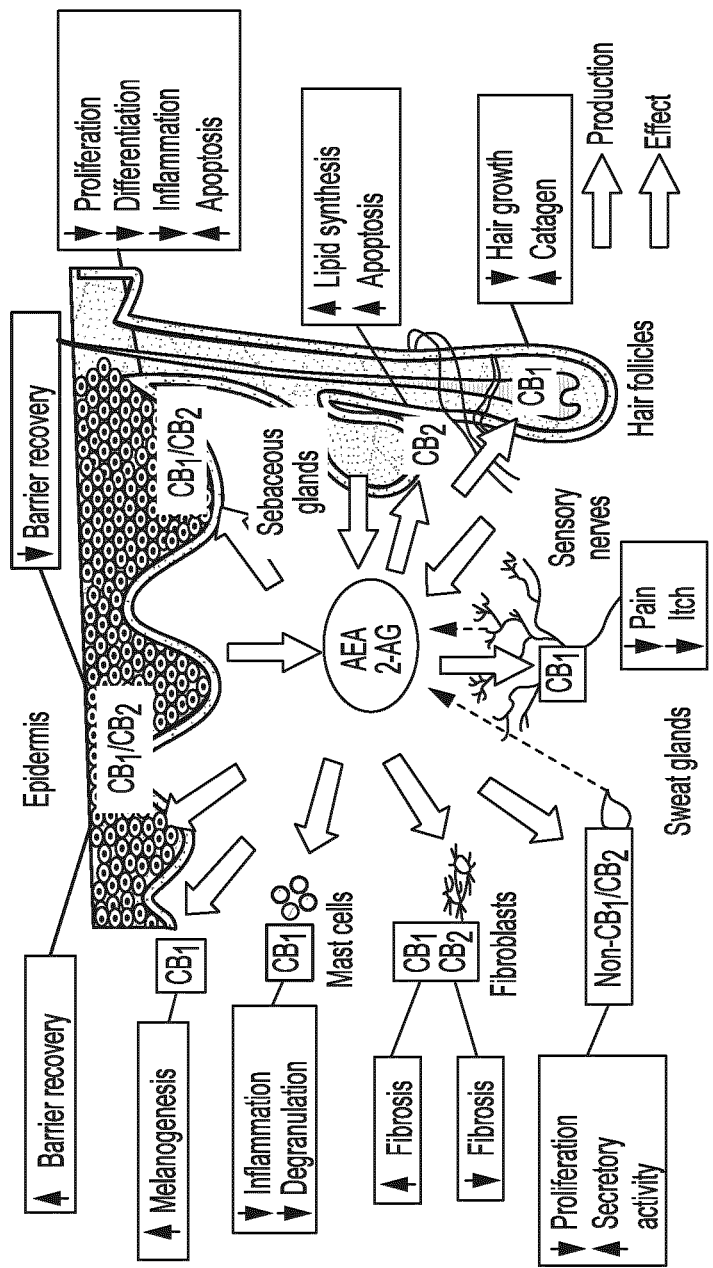
FIG. 19 is a diagram of a model developed in accordance with the experimental results described herein. The model illustrates the endocannabinoid system and the skin; endocannabinoids and cannabinoid receptors are implicated as described herein in multiple regulatory systems in the skin.

FIG. 19 is a diagram of a model developed in accordance with the experimental results described herein. The model illustrates endocannabinoids and cannabinoid receptors that are implicated in multiple regulatory systems in the skin.

Figure 20:
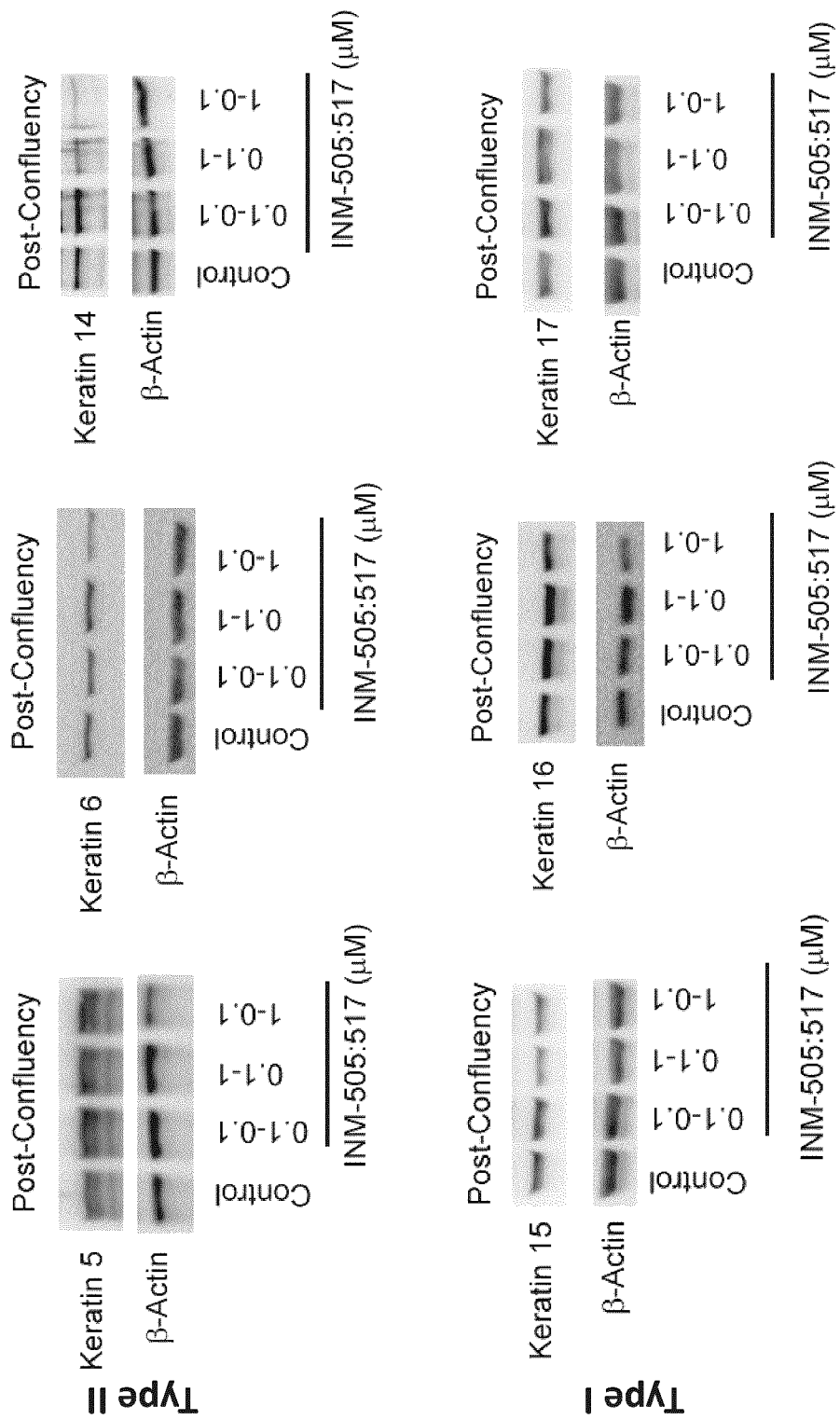
FIG. 20 is a graph showing the effects of different mixtures of INM-505 (cannabidiols) and INM-517 (cannabinol) on expression of Type II (K5, K6, and K14) and Type I (K15, K16, K17) keratins. INM-505 and INM-517 alone or in combination (INM-505:INM-517) generally increases K5, 14, 15, 16 and 17 protein expression in post-differentiating human keratinocyte cells (concentration dependent effect).

FIG. 20 is a graph showing the effects of different mixtures of INM-505 (cannabidiols) and INM-517 (cannabinol) on expression of Type II (K5, K6, and K14) and Type I (K15, K16, K17) keratins. INM-505 and INM-517 alone or in combination (INM-505:INM-517) generally increases K5, 14, 15, 16 and 17 protein expression in post-differentiating human keratinocyte cells (concentration dependent effect).

FIG. 21 shows the activity of cannabinoids in would healing by upregulating extra domain A (EDA)-fibronectin (left panel). TGF-β-induced inhibition of E-cadherin is rescued by cannabinoids (right panel).

Transforming Growth Factor (TGFβ1) beta is a master regulator of normal healing and pathological fibroproliferative processes of the skin. Excessive TGFβ pathway activation in skin fibroblasts lead to abnormal accumulation of ECM proteins including collagen and forming high dense fibrotic transformation of skin known as keloids. In addition, activated fibroblasts differentiate to myofibroblasts producing ample of mediators including TGFβ1. The latter is a key factor for Epithelial-Mesenchymal Transition (EMT), critical process of wound closure and regeneration by skin keratinocytes. Once EMT is exaggerated the process became pathologic and dramatically disturbs normal skin healing.

Cannabinoids (CBDs) are known for their potential anti-inflammatory action on human blood leukocytes. However, their effects on TGFβ-induced signaling in human keratinocytes and skin mesenchymal cells currently are unknown. The aim of the experiments whose results are reported below as FIGS. 22-25 is to determine effects of INM-501, INM-509, INM-505, INM-506, INM-513 (cannabigerol (CBG)), INM-517, and synthetic CBDs HU-210 and SR144528 (5-(4-chloro-3-methylphenyl)-1-[(4-methylphenyl)methyl]-N-[(1S,2S,4R)-1,3,3-trimethylbicyclo[2.2.1]heptan-2-yl]-1H-pyrazole-3-carboxamide), on basal and TGFβ1-induced Smooth Muscle Actin (αSMA) as marker of TGFβ signaling activation and myofibroblast differentiation of human fibroblasts and EMT in immortalized human keratinocytes line (HaCaT) in in vitro cultures.

Experimental Design: HaCaT and HFL-1 cells cultured in 24-well plates ($1\times10^5$ cells/well/mL) in DMEM supplemented with 1% FBS and antibiotics/antimycotics in the presence of INM-501, INM-509, INM-505, INM-506, INM-513 (cannabigerol (CBG)), INM-517, HU-210 ((6aR,10aR)-9-(hydroxymethyl)-6,6-dimethyl-3-(2-methyloctan-2-yl)-6H,6aH,7H,10H,10aH-benzo[c]isochromen-1-ol)), and SR144528 (all at 1 µM concentration, EchoPharmaceuticals, AT Nijmegen, The Netherlands, Cayman Chemical, Ann Arbor, MI) alone or with simultaneously added human recombinant TGFβ1 at 10 and 20 ng/ml concentrations for 72 hr. Cell culture supernatants were removed and cells were lyzed with Cell Protein Extraction Buffer supplemented with Proteinases/Phosphatases Inhibitors Cocktail. Cell Protein Extracts (CPE) were cleared by centrifugation and kept at −80° C. before assays.

Assay Procedures: EMT induced by TGFβ1 in keratinocytes was analyzed by expression of human E-Cadherin (E-CDH) and Cellular Fibronectin (FBN-EDA). Fibroblast activation and differentiation was determined by αSMA expression. E-CDH, FBN-EDA and αSMA proteins were determined by SDS-PAGE and Immunobloting using mouse anti-human E-CDH, FBN-EDA and αSMA monoclonal antibodies. HSP90 and β-Tubulin were used as loading controls. Detection was performed by LI-COR Infrared Imaging System and IR700/IR800 secondary antibodies (LI-COR Biosciences, Lincoln, NE). Density of the bands was quantified in two infrared channels independently using Odyssey software 2.1 (LI-COR Biosciences). The results are expressed as a protein/β-tubulin/HSP90 density ratio.

Figure 22:
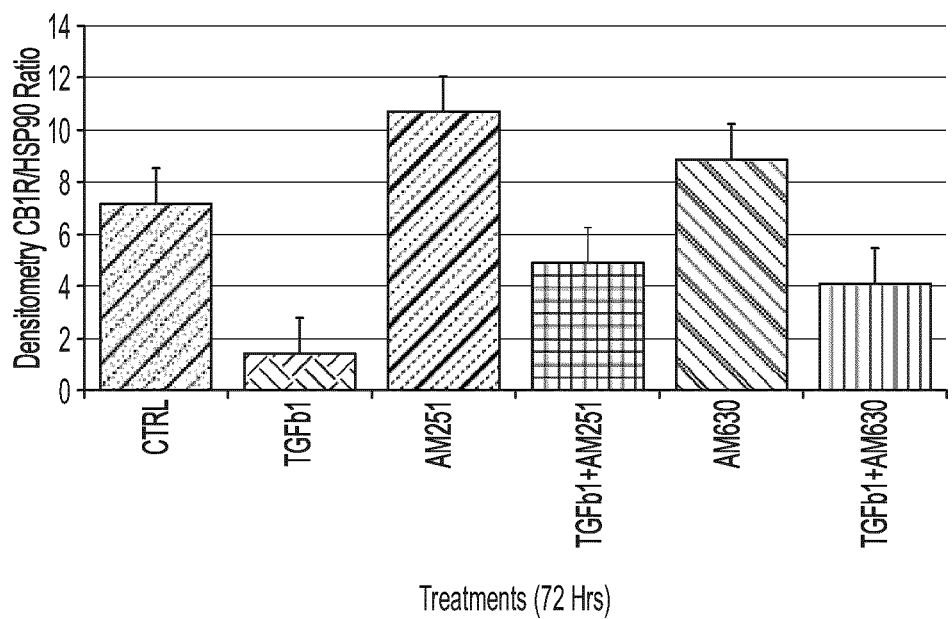
FIG. 22 shows that TGFβ1 dampens CB1 receptor expression by human fibroblasts, and CB1/CB2 synthetic antagonists AM251 (N-(piperidin-1-yl)-5-(4-iodophenyl)-1-(2,4-dichlorophenyl)-4-methyl-1H-pyrazole-3-carboxamide) and AM630 (6-iodopravadoline) modify cell responsiveness to TGFβ1. The top panel shows western blots showing CB1 receptor expression, and the bottom panel shows the CB1 receptor/HSP90 ratio, with HSP90 as a loading control.

Transforming growth factor (TGF)-β pathway activation is a key element of normal wound healing and pathologic fibroproliferative processes in the skin. TGFβ1 dampens CB1 receptor expression by human fibroblasts, and CB1/CB2 synthetic antagonists modify cell responsiveness to TGFβ1. FIG. 22 shows that TGFβ1 dampens CB1 receptor expression by human fibroblasts, and CB1/CB2 synthetic antagonists AM251 and AM630 modify cell responsiveness to TGFβ1. CB1 receptor expression is indicated as a CB1 receptor/HSP90 ratio, with HSP90 as a loading control. These data demonstrate there is a crosstalk between TGFb signaling and endocannabinoid system in the human mesenchyma. TGFβ1 downregulates CB1R expression and dampens an inhibitory feedback mechanism of CB1/CB2 activation in human fibroblast.

Figure 23:
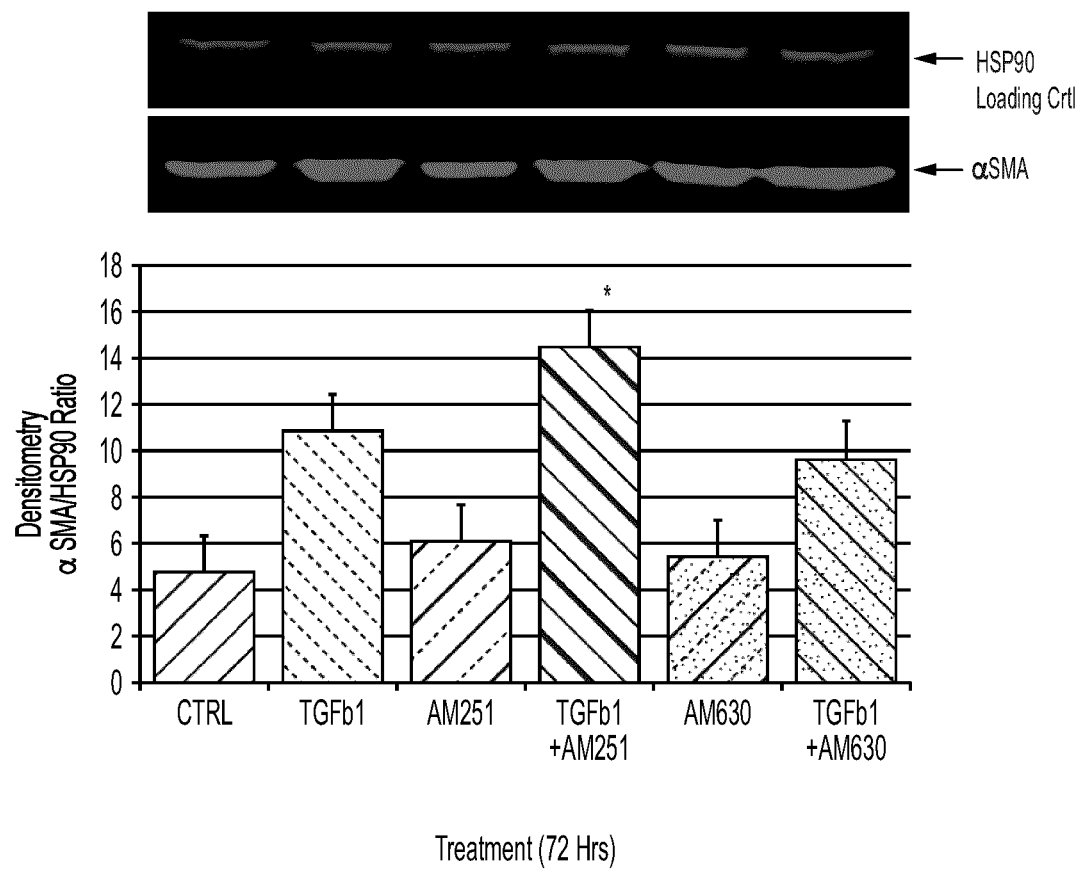
FIG. 23 shows that the CB1 receptor antagonist AM251 increases the TGFβ1-responsiveness of human fibroblasts by upregulating αSMA expression. The top panel shows western blots showing αSMA expression, and the bottom panel shows the αSMA/HSP90 ratio, with HSP90 as a loading control.

The CB1 receptor antagonist AM210 increases the TGFβ1-responsiveness of human fibroblasts by upregulating αSMA expression. FIG. 23 shows that the CB1 receptor antagonist AM251 increases the TGFβ1-responsiveness of human fibroblasts by upregulating αSMA expression. The top panel shows western blots showing αSMA expression, and the bottom panel shows the αSMA/HSP90 ratio, with HSP90 as a loading control. The CB1 receptor blocker AM210 promotes TGFβ1-induced αSMA expression—an important marker of myofibroblast differentiation, TGFβ signaling activation and fibrosis. These data suggest a potential role for the cannabinoid agonists or mixtures of cannabinoid agonists described above with CB1 receptor agonist activity as modulators of tissue remodeling and fibrosis.

Figure 24:
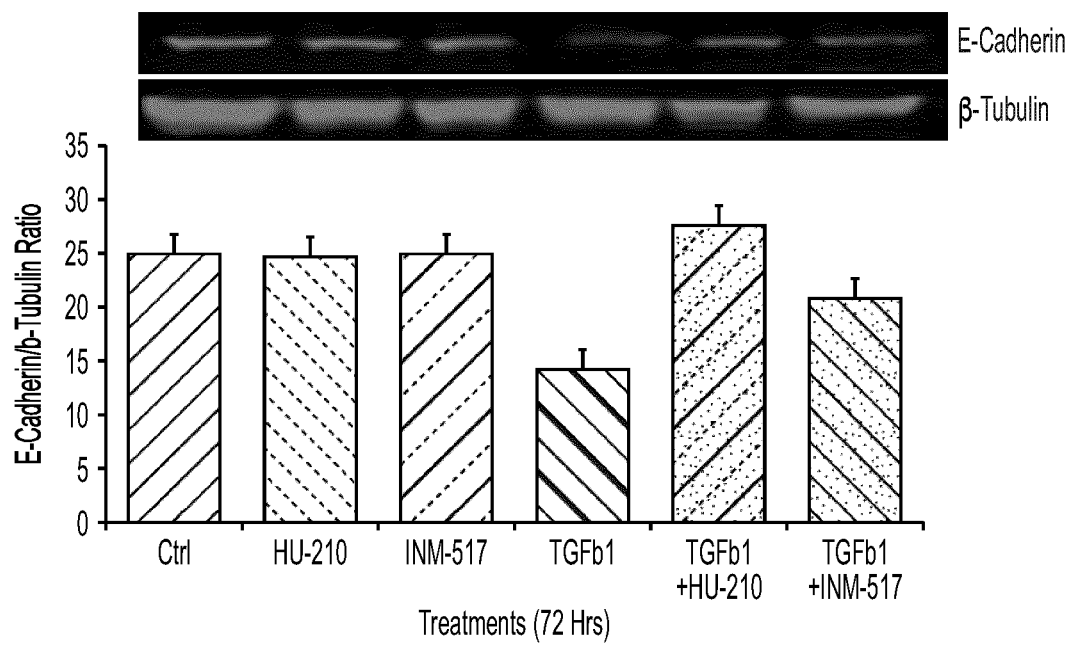
FIG. 24 shows that INM-750 enhances the physical integrity of skin via the rescue of TGFβ1-induced inhibition of E-cadherin by human keratinocytes. The top panel shows western plots for E-cadherin and β-tubulin as a loading control, and the bottom panel shows the E-cadherin/β-tubulin ratio.

The mixture of agonists referred to herein as "INM-750" potentiates the wound healing process by maintaining TGFβ1-induced expression of the cell protective fibronectin-EDA by human keratinocytes. FIG. 24 shows that INM-750 enhances the physical integrity of skin via the rescue of TGFβ1-induced inhibition of E-cadherin by human keratinocytes. The top panel shows western plots for E-cadherin and β-tubulin as a loading control, and the bottom panel shows the E-cadherin/β-tubulin ratio. Epithelial-Mesenchymal Transition (EMT) is a critical element of epithelial biology, cancer development, and fibrosis. Chronic activation of TGFβ-signaling in the skin ultimately leads to fibrosis (keloid). EMT of keratinocytes is an adaptive response in the normal wound healing process.

Figure 25:
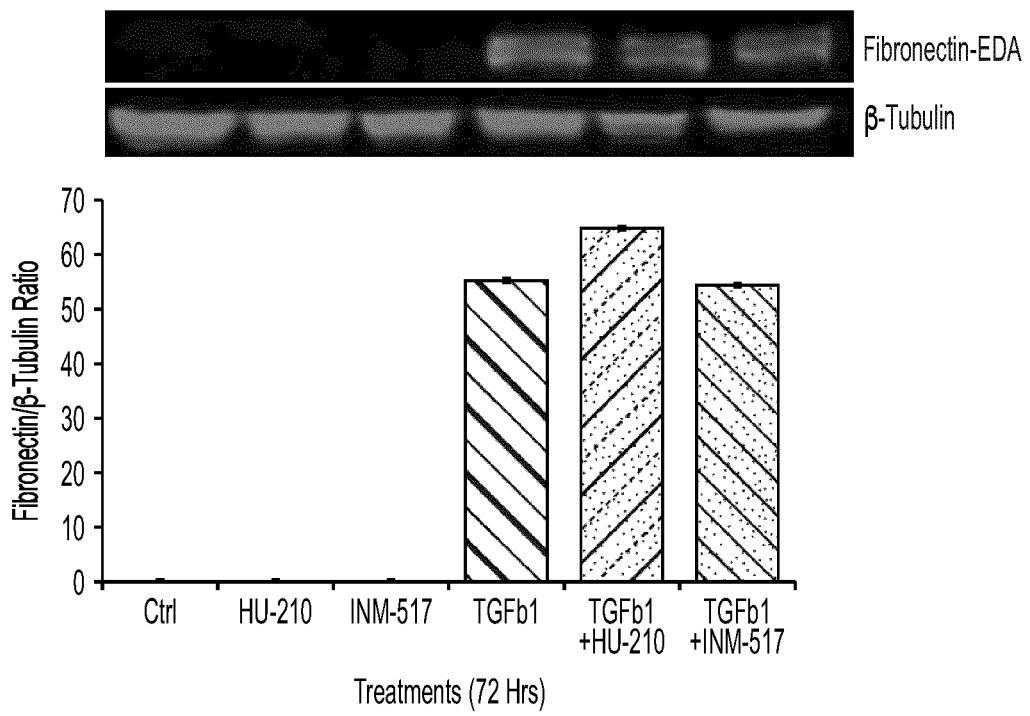
FIG. 25 shows that INM-750 potentiates the wound healing process by maintaining TGFβ1-induced expression of the cell protective fibronectin-EDA by human keratinocytes. The top panel shows western blots for fibronectin-EDA and β-tubulin as a loading control, and the bottom panel shows the fibronectin-EDA/β-tubulin ratio.

It is characterized by decrease of E-Cadherin (important element of keratinocyte integrity and tight junction formation) expression and upregulation of Cellular Fibronectin (Fibronectin-EDA) production. The latter is a very important protective element of epithelial cells during mucosal tissue repairs. Chronic EMT of keratinocytes in psoriasis has been shown a key element of disease pathogenesis. It is not yet known whether EMT is involved in EBS pathogenesis. It is predicted, however, that upregulation of TGFβ-signaling exists in chronic wounds associated with EBS. Therefore modulation of the excessive TGFβ impacts on skin keratinocytes and fibroblasts would be a beneficial option in an EBS treatment program. INM-517 displays a strong and potent effect on the E-Cadherin rescue after TGFβ exposure while preserving fibronectin-EDA production (both effects are beneficial for skin wound closure/healing). FIG. 25 shows that INM-750 potentiates the wound healing process by maintaining TGFβ1-induced expression of the cell protective fibronectin-EDA by human keratinocytes. The top panel shows western blots for fibronectin-EDA and β-tubulin as a loading control, and the bottom panel shows the fibronectin-EDA/β-tubulin ratio.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed.

Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

What is claimed is:

1. A method for treating epidermolysis bullosa (EB), the method comprising: topically administering to skin of a subject in need thereof a therapeutically effective quantity of cannabinol, wherein the therapeutically effective quantity is an amount sufficient to modulate an amount or activity of one or more keratins and stimulate wound healing when topically administered to the skin, and wherein the cannabinol is the only cannabinoid administered to the skin of the subject.

2. The method according to claim 1, wherein said epidermolysis bullosa (EB) is epidermolysis bullosa simplex (EBS).

3. The method according to claim 1, wherein said epidermolysis bullosa (EB) is selected from the group consisting of dystrophic epidermolysis bullosa (DB), and junctional epidermolysis bullosa (JB).

4. The method according to claim 1, wherein said therapeutically effective quantity is an amount sufficient to increase K15 mRNA or protein level or decrease K5 or K14 mRNA or protein level in a mitotically active basal layer of the topically administered skin.

5. The method according to claim 1, wherein said therapeutically effective quantity is an amount sufficient to increase K15 mRNA or protein level and decrease K5 or K14 mRNA or protein level in a mitotically active basal layer of the topically administered skin.

6. The method according to claim 1, wherein said therapeutically effective quantity is an amount sufficient to increase K15 mRNA or protein level and decrease K5 and K14 mRNA or protein level in a mitotically active basal layer of the topically administered skin.

7. The method of claim 1, wherein the therapeutically effective quantity is administered in a pharmaceutical composition, wherein the pharmaceutical composition comprises: (1) a therapeutically effective quantity of the cannabinol; and (2) at least one pharmaceutically acceptable carrier for topical administration of the composition.

8. The method of claim 7, wherein the pharmaceutically acceptable carrier is at least one pharmaceutically acceptable carrier selected from the group consisting of caprylocaproyl polyoxyl-8 glycerides, poloxamer 407, lecithin, and isopropyl palmitate.

9. The method of claim 8, wherein the pharmaceutically acceptable carrier comprises caprylocaproyl polyoxyl-8 glycerides, poloxamer 407, lecithin, and isopropyl palmitate.

10. The method of claim 7, wherein the pharmaceutical composition further comprises at least one pharmaceutically acceptable excipient selected from a binder, a filler, a disintegrant, a lubricant, a coating, a sweetener, a flavor, a color, and combinations thereof.

11. The method of claim 1, wherein the method further comprises a step of topically administering an additional therapeutically active agent selected from the group consisting of a topical anti-inflammatory agent, a topical anti-bacterial agent, a topical anti-fungal agent, a topical steroid, and a topical antioxidant to treat the EB.

12. The method of claim 1, wherein the method further comprises a step of topically administering a therapeutically effective quantity of a terpenoid.

13. The method of claim 12, wherein the cannabinol and the terpenoid are administered in a single pharmaceutical composition.

14. The method of claim 12, wherein the cannabinol and the terpenoid are administered separately.

15. The method of claim 12 wherein the terpenoid is selected from the group consisting of borneol, carvophyllene, 1,8-cineol, p-cymene, fenchone, α-humulene, kaempferol, limonene, linoleic acid, α-linolenic acid, luteolin, β-myrcene, oleic acid, orientin, α-pinene, phytol, quercetin, selinene, sitosterol, terpinenol-4, N-trans-caffeoyltyramine, N-trans-coumaroyltyramine, N-trans-ferruloyltyramine, and vitexin, wherein the method promotes anti-inflammatory activity.

16. The method of claim 12 wherein the terpenoid is selected from the group consisting of caryophyllene oxide, camphene, 1,8-cineole, p-cymene, kaempferol, limonene, linalool, nerolidol, α-pinene, β-pinene, phytol, β-sitosterol, and N-trans-caffeoyltyramine, wherein the method promotes anti-microbial activity.

17. The method of claim 12 wherein the terpenoid is selected from the group consisting of borneol, caryophyllene, p-cymene, linalool, β-sitosterol, and vitexin, wherein the method promotes anti-pain activity.

18. The method of claim 12 wherein the terpenoid is selected from the group consisting of borneol, linalool, and kaempferol, wherein the method promotes wound healing activity.

19. The method of claim 1, wherein the method accomplishes at least one of the following therapeutic activities:
   a. restoring anchoring function of skin;
   b. downregulating one or both of K5 and K14;
   c. upregulating K15;

d. rescuing TGF-β-induced downregulation of E-cadherin; or
e. increasing MCP-1 production.

* * * * *